(12) United States Patent
Scaria et al.

(10) Patent No.: US 12,241,078 B2
(45) Date of Patent: Mar. 4, 2025

(54) AAV VECTORS FOR RETINAL AND CNS GENE THERAPY

(71) Applicant: Genzyme Corporation, Cambridge, MA (US)

(72) Inventors: Abraham Scaria, Framingham, MA (US); Jennifer Sullivan, Cambridge, MA (US); Lisa M. Stanek, Natick, MA (US); Lamya S. Shihabuddin, West Newton, MA (US)

(73) Assignee: Genzyme Corporation, Cambridge, MA (US)

( * ) Notice: Subject to any disclaimer, the term of this patent is extended or adjusted under 35 U.S.C. 154(b) by 1007 days.

(21) Appl. No.: 17/194,009

(22) Filed: Mar. 5, 2021

(65) Prior Publication Data

US 2021/0189430 A1 Jun. 24, 2021

Related U.S. Application Data

(62) Division of application No. 15/308,335, filed as application No. PCT/US2015/028966 on May 2, 2015, now Pat. No. 10,982,228.

(60) Provisional application No. 61/988,131, filed on May 2, 2014, provisional application No. 62/114,575, filed on Feb. 10, 2015.

(51) Int. Cl.
| | |
|---|---|
| *C12N 15/86* | (2006.01) |
| *A61K 48/00* | (2006.01) |
| *C07K 14/015* | (2006.01) |
| *C07K 14/71* | (2006.01) |
| *C12N 7/00* | (2006.01) |
| *C12N 15/113* | (2010.01) |

(52) U.S. Cl.
CPC .......... *C12N 15/86* (2013.01); *A61K 48/0075* (2013.01); *C07K 14/015* (2013.01); *C07K 14/71* (2013.01); *C12N 7/00* (2013.01); *C12N 15/113* (2013.01); *C12N 2310/141* (2013.01); *C12N 2320/32* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

| | | |
|---|---|---|
| 4,692,147 A | 9/1987 | Duggan |
| 5,735,815 A | 4/1998 | Bair |
| 6,042,579 A | 3/2000 | Elsberry et al. |
| 6,225,291 B1 | 5/2001 | Lewin et al. |
| 6,566,118 B1 | 5/2003 | Atkinson et al. |
| 6,596,535 B1 | 7/2003 | Carter |
| 6,723,551 B2 | 4/2004 | Kotin et al. |
| 6,953,575 B2 | 10/2005 | Bankiewicz et al. |
| 6,989,264 B2 | 1/2006 | Atkinson et al. |
| 6,995,006 B2 | 2/2006 | Atkinson et al. |
| 7,125,717 B2 | 10/2006 | Carter et al. |
| 7,341,577 B2 | 3/2008 | Gill |
| 7,351,239 B2 | 4/2008 | Gill |
| 7,465,583 B2 | 12/2008 | Samulski et al. |
| 7,629,322 B2 | 12/2009 | Kleinschmidt et al. |
| 7,790,154 B2 | 9/2010 | Samulski et al. |
| 7,846,729 B2 | 12/2010 | Carter |
| 7,867,484 B2 | 1/2011 | Samulksi |
| 7,922,999 B2 | 4/2011 | Bankiewicz |
| 8,093,054 B2 | 1/2012 | Carter |
| 8,137,948 B2 | 3/2012 | Qu et al. |
| 8,361,457 B2 | 1/2013 | Samulski et al. |
| 10,982,228 B2 | 4/2021 | Scaria et al. |
| 2002/0141980 A1 | 10/2002 | Bankiewicz et al. |
| 2006/0051333 A1 | 3/2006 | Arbetman |
| 2006/0088936 A1 | 4/2006 | Warrington |
| 2006/0135945 A1 | 6/2006 | Bankiewicz et al. |
| 2007/0036757 A1 | 2/2007 | Kleinschmidt |
| 2007/0088295 A1 | 4/2007 | Bankiewicz et al. |

(Continued)

FOREIGN PATENT DOCUMENTS

| | | |
|---|---|---|
| CN | 101495624 A | 7/2009 |
| CN | 103561774 A | 2/2014 |

(Continued)

OTHER PUBLICATIONS

Vandenberghe et al. Naturally Occurring Singleton Residues in AAV Capsid Impact Vector Performance And Illustrate Structural Constraints. Gene Therapy, 2009. 16: 1416-1428.*
Arnett, A. L. H. et al. (May 2013, e-pub. Aug. 2, 2012). "Heparin-Binding Correlates With Increased Efficiency Of AAV1-And AAV6-Mediated Transduction Of Striated Muscle, But Negatively Impacts CNS Transduction," Gene Therapy 20(5):497-503.
Coune, P. G. et al. (Apr. 1, 2012). "Parkinson's Disease: Gene Therapies," Cold Spring Harbor Perspectives In Medicine 2(4):a009431.
Mastakov, M.Y. et al. (Apr. 1, 2002). "Recombinant Adeno-Associated Virus Serotypes 2-And 5-Mediated Gene Transfer In The Mammalian Brain: Quantitative Analysis Of Heparin Co-Infusion," Molecular Therapy 5(4):371-380.

(Continued)

*Primary Examiner* — Christopher M Babic
*Assistant Examiner* — Kimberly A Aron
(74) *Attorney, Agent, or Firm* — Morrison & Foerster LLP

(57) ABSTRACT

Provided herein are improved rAAV (e.g., rAAV2, rAAVrh8R, etc.) for enhanced gene therapy of ocular disorders or CNS disorders wherein the rAAV comprise one or more substitutions of amino acids that interact with heparan sulfate proteoglycan. The invention provides methods for improved transduction of retinal cells and methods for treating ocular diseases with improved compositions of rAAV particles. Further provided herein are improved recombinant adeno-associated virus (rAAV) (e.g., rAAV2, rAAVrh8R, etc.) for enhanced gene therapy of disorders of the CNS. The invention provides methods for delivering the rAAV to the CNS, methods for treating disorders of the CNS with improved compositions of rAAV particles, and kits for delivering the rAAV to the CNS and/or treating a CNS disorder.

37 Claims, 21 Drawing Sheets

Specification includes a Sequence Listing.

(56) References Cited

U.S. PATENT DOCUMENTS

| | | |
|---|---|---|
| 2007/0259031 A1 | 11/2007 | Bankiewicz et al. |
| 2009/0317417 A1 | 12/2009 | Vandenberghe et al. |
| 2012/0009268 A1 | 1/2012 | Asokan et al. |
| 2014/0335054 A1 | 11/2014 | Gao et al. |
| 2017/0096683 A1 | 4/2017 | Scaria et al. |

FOREIGN PATENT DOCUMENTS

| | | |
|---|---|---|
| EP | 1486567 A1 | 12/2004 |
| WO | WO-98/10088 A1 | 3/1998 |
| WO | WO-99/61066 A2 | 12/1999 |
| WO | WO-2004/027019 A2 | 4/2004 |
| WO | 2004099423 A1 | 11/2004 |
| WO | WO-2004/111248 A2 | 12/2004 |
| WO | WO-2006/042090 A1 | 4/2006 |
| WO | WO-2006/110689 A2 | 10/2006 |
| WO | WO-2008/144585 A1 | 11/2008 |
| WO | WO-2009/105690 A2 | 8/2009 |
| WO | WO-2010/088560 A1 | 8/2010 |
| WO | WO-2010/093784 A2 | 8/2010 |
| WO | WO-2010/148143 A1 | 12/2010 |
| WO | WO-2012/145601 A2 | 10/2012 |
| WO | WO-2013/173129 A2 | 11/2013 |
| WO | 2015012501 A1 | 1/2015 |

OTHER PUBLICATIONS

Mccurdy, J.V. et al. (Dec. 4, 2014). "Widespread Correction Of Central Nervous System Disease After Intracranial Gene Therapy In A Feline Model Of Sandhoff Disease," Gene Therapy 22(2):181-189.

Nguyen, J.B. et al. (Jul. 2001). "Convection-Enhanced Delivery of AAV-2 Combined with Heparin Increases TK Gene Transfer in the Rat Brain," NeuroReport 12(9):1961-1964.

Notice of European Opposition for European Patent No. 3137497, dated Jan. 13, 2022, Proprietor Genzyme Corporation, Opponent European Oppositions Limited, 8 pages.

Purves, D. (2001). "The Retina," Chapter 11 in Neuroscience, 2nd Edition, NCBI Bookshelf, A Service of the National Library of Medicine, National Institutes of Health, Sunderland, MA, 3 pages.

Samulski, R. J. et al. (Jun. 1989). "Helper-Free Stocks Of Recombinant Adeno-Associated Viruses: Normal Integration Does Not Require Viral Gene Expression," Journal Of Virology 63(9):3822-3828.

Samulski, R. J. et al. (Sep. 2014). "AAV-Mediated Gene Therapy For Research And Therapeutic Purposes," Annual Review Of Virology 1:427-451.

Sequence Alignment of SEQ ID No. 1 of EP3137497 and SEQ ID No. 2 of EP3137497 of the Patent, 2 pages.

Watanabe, S. et al. (Jan. 15, 2013). "Tropisms of AAV 1-20 for Subretinal Delivery to the Neonatal Mouse Retina and Its Application for In Vivo Rescue of Developmental Photoreceptor Disorders," PLOS One 8(1):e54146, 12 pages.

Weismann, C.M. (Aug. 5, 2014). "Approaches And Considerations Towards A Safe And Effective Adena-Associated Virus Mediated Therapeutic Intervention For GMI-Gangliosidosis (Dissertation)," GSBS Dissertations and Theses, FP-181, 198 pages.

Yang, B. et al. (Jul. 1, 2014). "Global CNS Transduction of Adult Mice by Intravenously Delivered rAAVrh.8 and rAAVrh.10 and Nonhuman Primates by rAAVrh.10," Molecular Therapy 22(7):1299-1309.

Allocca, M. et al. (Oct. 2007, e-pub Aug. 15, 2007). "Novel Adeno-Associated Virus Serotypes Efficiently Transduce Murine Photoreceptors," Journal of Virology 81(20):11372-11380.

Andersen, J.K. et al. (Oct. 13, 1993). "Herpesvirus-Mediated Gene Delivery Into the Rat Brain: Specificity And Efficiency of the Neuron-Specific Enolase Promoter," Cell. Mol. Neurobiol. 13(5):503-515.

Aslanidi, G.V. et al. (2012, e-pub. Apr. 10, 2012). "High-Efficiency Transduction of Human Monocyte-Derived Dendritic Cells by Capsid-Modified Recombinant AAV2 Vectors," Vaccine 30:3908-3917.

Bankiewicz, K.S. et al. (2000). "Convection-Enhanced Delivery of AAV Vector in Parkinsonian Monkeys; In Vivo Detection of Gene Expression and Restoration of Dopaminergic Function Using Prodrug Approach," Exp. Neurol. 164:2-14.

Boison, D. (Sep. 2010, e-pub Jul. 15, 2010). "Inhibitory RNA in Epilepsy: Research Tool And Therapeutic Perspectives," Epilepsia 51(9):1659-1668, 16 pages.

Boshart, M. et al. (Jun. 1985). "A Very Strong Enhancer Is Located Upstream of an Immediate Early Gene of Human Cytomegalovirus," Cell 41:521-530.

Bossis, I. et al. (Jun. 2003) "Cloning of an Avian Adeno-Associated Virus (AAAV) and Generation of Recombinant AAAV Particles," J. Virol. 77(12):6799-6810.

Boye et al. Impact of Heparan Sulfate Binding On Transduction of Retina By Recombinant Adena-Associated Virus Vectors. Journal of Virology, 2016. 90(8):4215-4231.

Christine, C.W. et al. (Nov. 17, 2009). "Safety and Tolerability of Putaminal AADC Gene Therapy for Parkinson Disease," Neurology 73:1662-1669.

Clark, D.P. (2009). "Understanding the Genetic Revolution," Molecular Biology ProQuest Ebook Central located at https://ebookcentral.proquest.com/lib/uspto-ebooks/detail.action?docID=269863.

Clark, K.R. et al. (Apr. 10, 1999). "Highly Purified Recombinant Adeno-Associated Virus Vectors are Biologically Active and Free of Detectable Helper and Wild-Type Viruses," Hum. Gene Ther. 10(6):1031-1039.

Conway, J.E. et al. (Nov. 1997). "Recombinant Adeno-Associated Virus Type 2 Replication and Packaging is Entirely Supported by a Herpes Simplex Virus Type 1 Amplicon Expressing Rep and Cap," J. Virology 71(11):8780-8789.

Costantini, L.C. et al. (2000). "Gene therapy in the CNS," Gene Therapy 7:93-109.

Cunningham, et al. (). "High-Resolution Epitope Mapping of hGH-receptor Interactions by Alanine-Scanning Mutagenesis," Science 244:1081-1085.

Dalkara, D. et al. (Dec. 2009, e-pub Aug. 11, 2009). "Inner Limiting Membrane Barriers to AAV-mediated Retinal Transduction From the Vitreous," Molecular Therapy 17(12):2096-2102.

Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," PNAS 97(7):3428-32.

Eberling, J.L. et al. (May 20, 2008, e-pub Apr. 9, 2008). "Results from a Phase I Safety Trial of hAADC Gene Therapy for Parkinson Disease," Neurology 70(21):1980-1983.

Fagan, X.J. et al. (Jul. 2013). "Intravitreal Injections: A Review of the Evidence for Best Practice," Clin. Experiment. Ophthalmol. 41(5):500-507.

Fiandaca, M.S. et al. (2009, e-pub. Nov. 27, 2008). "Real-Time MR Imaging of Adeno-Associated Viral Vector Delivery to the Primate Brain," Neuroimage 47(Suppl 2):T27-35.

Fisher, K.J. et al. (Jan. 1996). "Transduction with Recombinant Adeno-Associated Virus for Gene Therapy is Limited by Leading-Strand Synthesis" J. Virol. 70(1):520-532.

Forsayeth, J.R. et al. (Oct. 2006, e-pub Jun. 16, 2006). "A Dose-Ranging Study of AAV-hAADC Therapy in Parkinsonian Monkeys," Mol. Ther. 14(4):571-577, 15 pages.

Fukuda, A.M. et al. (Sep. 5, 2013). "siRNA Treatment: 'A Sword-in-the-Stone' for Acute Brain Injuries," Genes (Basel) 4(3):435-456.

Gao, G.P. et al. (May 13, 2003). "Adeno-Associated Viruses Undergo Substantial Evolution in Primates During Natural Infections," PNAS 100(10):6081-6086.

Gao, G.P. et al. (Sep. 3, 2002). "Novel Adeno-Associated Viruses from Rhesus Monkeys as Vectors for Human Gene Therapy," PNAS 99(18):11854-11859.

Genbank. (Aug. 13, 2018). GenBank Accession No. NC 006261, "Adeno-associated Virus—8, Complete Genome," 3 pages.

Genbank. (Jan. 12, 1998). GenBank Accession No. AF028704, "Adeno-associated Virus 6, Complete Genome," 3 pages.

(56) References Cited

OTHER PUBLICATIONS

Genbank. (May 14, 2003). GenBank Accession No. AY242997, "Non-Human Primate Adeno-associated Virus Isolate AAVrh.8 Capsid Protein (VP1) Gene, Complete Cds," 2 pages.
Giove, T.J. et al. (Nov. 2010). "Transduction of the Inner Mouse Retina Using AAVrh8 and AAVrh10 Viaintravitreal Injection," *Exp Eye Res.* 91(5):652-659, 15 pages.
Gossen, M. et al. (Jun. 15, 1992). "Tight control of gene expression in mammalian cells by tetracycline-responsive promoters," *Proc. Natl. Acad. Sci. USA* 89(12):5547-5551.
Gossen, M. et al. (Jun. 23, 1995). "Transcriptional Activation by Tetracyclines in Mammalian Cells," *Science* 268(5218):1766-1769.
Guo, Z.S. et al. (1996). "Evaluation of Promoter Strength for Hepatic Gene Expression in Vivo Following Adenovirus-Mediated Gene Transfer," *Gene Ther.* 3(9):802-810.
Hadaczek, P. et al. (Mar. 2006). "Convection-Enhanced Delivery of Adeno-Associated Virus Type 2 (AAV2) into the Striatum and Transport of AAV2 Within Monkey Brain," *Hum. Gene Ther.* 17:291-302.
Halder, S. et al. (2015, e-pub. Aug. 31, 2015). "Structure of Neurotropic Adeno-Associated Virus AAVrh.8," Journal of Structural Biology 192:21-36.
Harvey, D.M. et al. (1998). "Inducible Control of Gene Expression: Prospects for Gene Therapy," *Curr. Opin. Chem. Biol.* 2:512-518.
Huntington Study Group (1996). "Unified Huntington's Disease Rating Scale: Reliability and-Consistency," *Movement Disorders* 11(2):136-142.
Kaplitt, M.G. et al. (Jun. 23, 2007). "Safety and Tolerability of Gene Therapy with an Adeno-Associated Virus (AAV) Borne GAD Gene for Parkinson's Disease: an Open Label, Phase I Trial," Lancet 369:2097-2105.
Kern, A. et al. (Oct. 2003). "Identification of a Heparin-Binding Motif on Adeno-Associated Virus Type 2 Capsids," *J. Virol.* 77(20):11072-11081.
Khani, S.C. et al. (Sep. 2007). "AAV-Mediated Expression Targeting of Rod and Cone Photoreceptors with a Human Rhodopsin Kinase Promoter," *Invest. Ophthalmol. Vis. Sci.* 48(9):3954-3961.
Kim, D.W. et al. (Jul. 16, 1990). "Use of the human elongation factor 1 alpha promoter as a versatile and efficient expression system," *Gene* 91(2):217-223.
Kotin, R.M. (Jul. 1994). "Prospects for the Use of Adeno-Associated Virus as a Vector for Human Gene Therapy," *Hum. Gene Ther.* 5(7):793-801.
Krauze, M.T. et al. (2009). "Convection-Enhanced Delivery of Liposomes to Primate Brain," *Methods Enzymol.* 465:349-362.
Lochrie et al. Mutations on the External Surfaces of Adena-Associated Virus Type 2 Capsids That Affect Transduction and Neutralization. Journal of Virology, 2006. 80(2):821-834.
Magari, S.R. et al. (Dec. 1997). "Pharmacologic Control of a Humanized Gene Therapy System Implanted into Nude Mice," J. Clin. Invest. 100(11):2865-2872.
Mandel, R.J. (Apr. 2010) "CERE-110, an Adeno-Associated Virus-Based Gene Delivery Vector Expressing Human Nerve Growth Factor for the Treatment Of Alzheimer's Disease," *Curr. Opin. Mol. Ther.* 12(2):240-247.
Martin, J. et al. (Aug. 2013, e-pub Aug. 9, 2013). "Generation and Characterization of Adeno-Associated Virus Producer Cell Lines for Research and Preclinical Vector Production," *Human Gene Therapy Methods* 24(4):253-269.
Mclaughlin, S.K. et al. (Jun. 1988). "Adeno-Associated Virus General Transduction Vectors: Analysis of Proviral Structures," *J. Virol.* 62(6):1963-1973.
Miyazaki, J. et al. (1989). "Expression Vector System Based on the β-actin Promoter Directs Efficient Production of Interleukin-5," *Gene* 79(2):269-277.
Müller, O.J. et al. (Apr. 1, 2006, e-pub Jan. 31, 2006). "Improved cardiac gene transfer by transcriptional and transductional targeting of adeno-associated viral vectors," *Cardiovascular Research* 70(1):70-78.

Niwa, H. et al. (1991). "Efficient Selection for High-Expression Transfectants with a Novel Eukaryotic Vector," *Gene* 108(2):193-200.
No, D. et al. (Apr. 16, 1996). "Ecdysone-Inducible Gene Expression in Mammalian Cells and Transgenic Mice," *Proc. Natl. Acad. Sci. USA* 93(8):3346-3351.
O'Donnell et al. Adena-Associated Virus-2 and Its Primary Cellular Receptor —Cryo-EM Structure of a Heparin Complex. Virology, 2009. 385:434-443.
Opie, S.R. et al. (Jun. 2003). "Identification of Amino Acid Residues in the Capsid Proteins of Adeno-Associated Virus Type 2 That Contribute to Heparan Sulfate Proteoglycan Binding," *J. Virol.* 77(12):6995-7006.
Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Virol.* 77(12):7034-7040.
Pechan, P. et al. (2009, e-pub. Jul. 17, 2008). "Novel Anti-VEGF Chimeric Molecules Delivered by AAV Vectors For Inhibition of Retinal Neovascularization," *Gene Ther.* 16:10-16.
Petrs-Silva et al. Novel Properties of Tyrosine-mutant AAV2 Vectors in the Mouse Retina. Molecular Therapy, 2011. 19(2):293-301.
Peyman, G.A. et al. (Jul.-Aug. 2009). "Intravitreal Injection of Therapeutic Agents," *Retina* 29(7):875-912.
Piccioli, P. et al. (Aug. 1995). "Neuroantibodies: Ectopic Expression of a Recombinant Anti-Substance P Antibody in the Central Nervous System of Transgenic Mice," *Neuron* 15(2):373-384.
Piccioli, P. et al. (Jul. 1991). "Neuroantibodies: Molecular Cloning of a Monoclonal Antibody Against Substance P for Expression in the Central Nervous System," *Proc. Natl. Acad. Sci. USA* 88:5611-5615.
Qing, K. et al. (Jan. 1999). "Human Fibroblast Growth Factor Receptor 1 is a Co-Receptor for Infection by Adeno-Associated Virus 2," *Nat. Medicine* 5(1):71-77.
Rabinowitz, J.E. et al. (Jan. 2002). "Cross-Packaging of a Single Adeno-Associated Virus (AAV) Type 2 Vector Genome into Multiple AAV Serotypes Enables Transduction with Broad Specificity," *J. Virol.* 76(2):791-801.
Sanftner, L.M. et al. (Aug. 2005, e-pub Nov. 3, 2013). "AAV2-Mediated Gene Delivery to Monkey Putamen: Evaluation of an Infusion Device and Delivery Parameters," *Exp. Neurol.* 194(2):476-483, 17 pages.
Slow, E.J. et al. (Jul. 1, 2003). "Selective Striatal Neuronal Loss in a YAC128 Mouse Model of Huntington Disease," *Hum. Mol. Genet.* 12(13):1555-1567.
Stanek, L.M. et al. (May 1, 2014, e-pub Jan. 31, 2014). "Silencing Mutant Huntingtin by Adeno-Associated Virus-Mediated RNA Interference Ameliorates Disease Manifestations in the YAC128 Mouse Model of Huntington's Disease," *Hum. Gene Ther.* 25(5):461-474.
Summerford, C. et al. (Feb. 1998). "Membrane-Associated Heparan Sulfate Proteoglycan Is A Receeptor For Adeno-Associated Virus Type 2 Virions," *J. Virol.* 72(2):1438-1445.
Summerford, C. et al. (Jan. 1999). "αVβ5 Integrin: A Co-Receptor for Adeno-Associated Virus Type 2 Infection," *Nat. Medicine* 5(1):78-82.
Van Raamsdonk, J.M. et al. (Dec. 15, 2005, e-pub Nov. 8, 2005). "Selective degeneration and nuclear localization of mutant huntingtin in the YAC128 mouse model of Huntington disease," *Hum. Mol. Genet.* 14(24):3823-3835.
Vandenberghe, L.H. et al. (Aug. 2006, e-pub Jul. 16, 2006). "Heparin Binding Directs Activation of T Cells Against Adeno-Associated Virus Serotype 2 Capsid," *Nature Medicine* 12(8):967-971.
Veldwijk, M.R. et al. (Aug. 2002). "Development and Optimization of a Real-Time Quantitative PCR-Based Method for the Titration of AAV-2 Vector Stocks," *Mol. Ther.* 6(2):272-278.
Wang, Y. et al. (Mar. 1997). "Ligand-Inducible and Liver-Specific Target Gene Expression in Transgenic Mice," *Nat. Biotech.* 15(3):239-243.
Wang, Y. et al. (May 1997). "Positive and Negative Regulation of Gene Expression in Eukaryotic Cells with an Inducible Transcriptional Regulator," *Gene Ther.* 4(5):432-441.

(56) References Cited

OTHER PUBLICATIONS

Wang, Z. et al. (2003). "Rapid and Highly Efficient Transduction by Double-Stranded Adeno-Associated Virus Vectors in Vitro and in Vivo," *Gene Ther.* 10:2105-2111.

Wu et al. (2000). "Mutational Analysis of the Adeno-Associated Vireus Type 2 (AAV2) Gene Capsid and Construction of the AAV2 Vectors with Altered Tropism," J. Virol. 74(18):8635-8647.

Wu, Z. et al. (Sep. 2006, e-pub. Jul. 7, 2006). "Adeno-Associated Virus Serotypes: Vector Toolkit for Human Gene Therapy," *Molecular Therapy* 14(3):316-327.

Xiao, X. et al. (Mar. 1997). "Gene Transfer by Adeno-Associated Virus Vectors into the Central Nervous System," *Exp. Neurobiol.* 144(1):113-124.

Xiao, X. et al. (Mar. 1998) "Production of High-Titer Recombinant Adeno-Associated Virus Vectors in the Absence of Helper Adenovirus," *Journal of Virology* 72(3):2224-2232.

Xie, Q. et al. (Aug. 6, 2002). "The atomic structure of adeno-associated virus (AAV-2), a vector for human gene therapy," Proc. Natl. Acad. Sci. 99(16):10405-10410.

Young, J.E. et al. (Sep. 2003). "A Short, Highly Active Photoreceptor-Specific Enhancer/Promoter Region Upstream of the Human Rhodopsin Kinase Gene," *Invest. Ophthalmol. Vis. Sci.* 44(9):4076-4085.

Sullivan, J. A. et al. (Jun. 2018, e-pub. May 22, 2018). "Rationally Designed AAV2 And AAVrh8R Capsids Provide Improved Transduction In The Retina And Brain," Gene Therapy 25(3):205-219.

Yang, B. et al. (May 2012). "526. Intravasuclar Delivery of RAAVRH. 8 Generates Widespreading Transduction of Neuronal and Glial Cell Types in the Adult Mouse Central Nervous System," Molecular Therapy 20(1):S203-S204.

\* cited by examiner

| AAV2 amino acid # | 484 | 487 | 532 | 585 | 588 |
|---|---|---|---|---|---|
| AAV2 | R | R | K | R | R |
| AAV2 HBKO | R | R | K | A | A |

FIG. 1

Arginine mutations decrease AAV2 intravitreal transduction in mouse eye

AAV2-CBA-GFP

- Outer retina
- Inner retina
- Inner Limiting membrane
- VITREOUS

AAV2HBKO(ArginineKO)

No transduction

FIG. 5

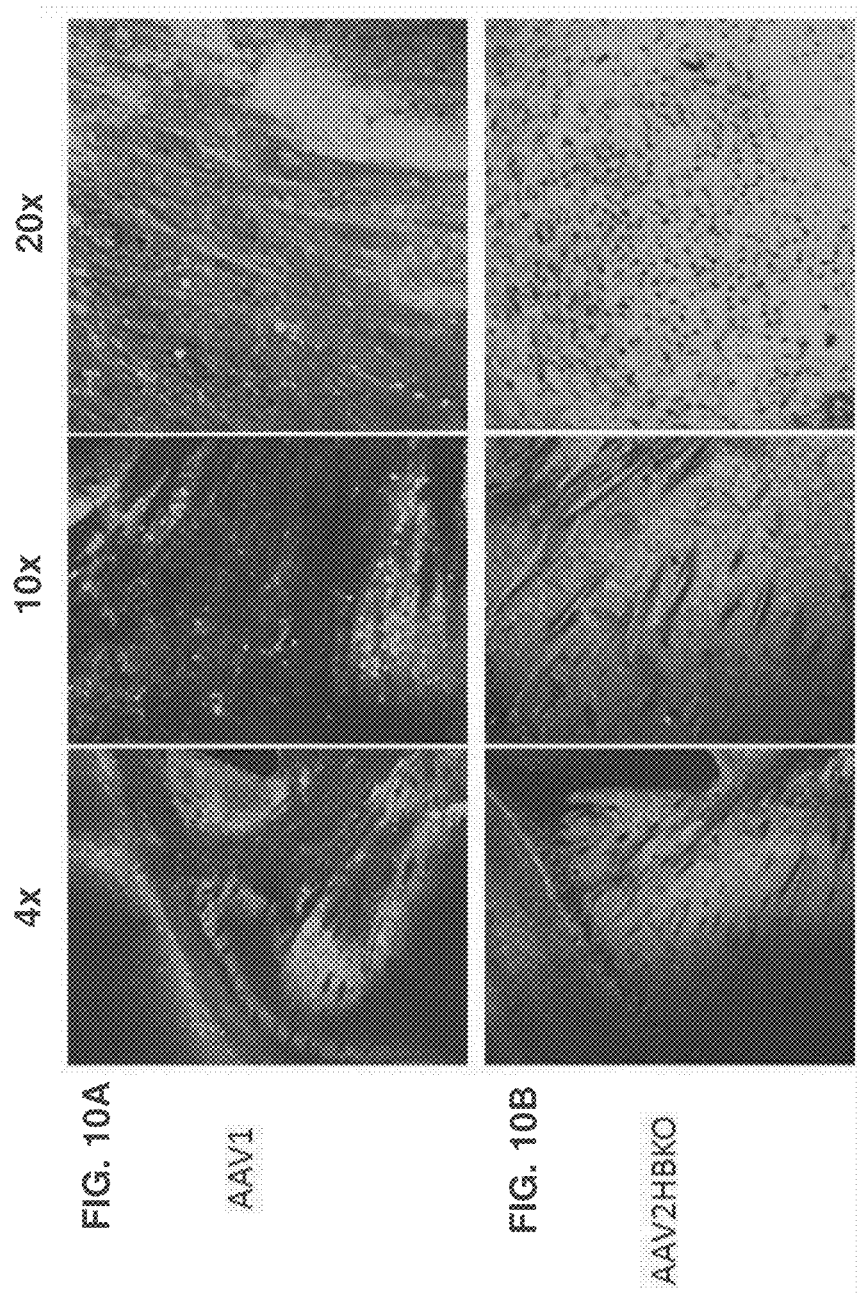

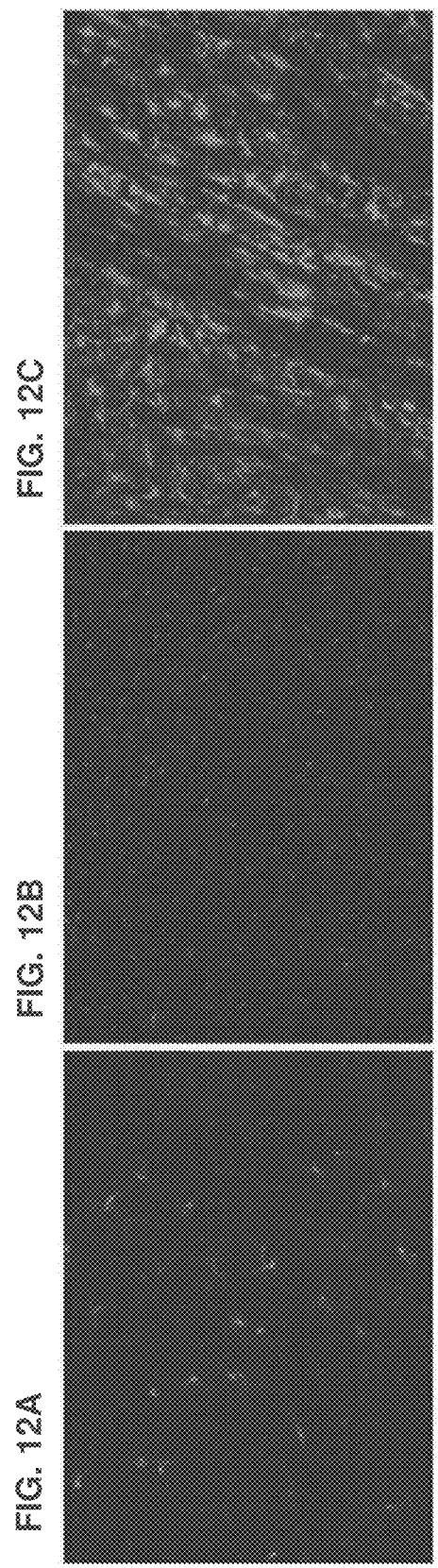

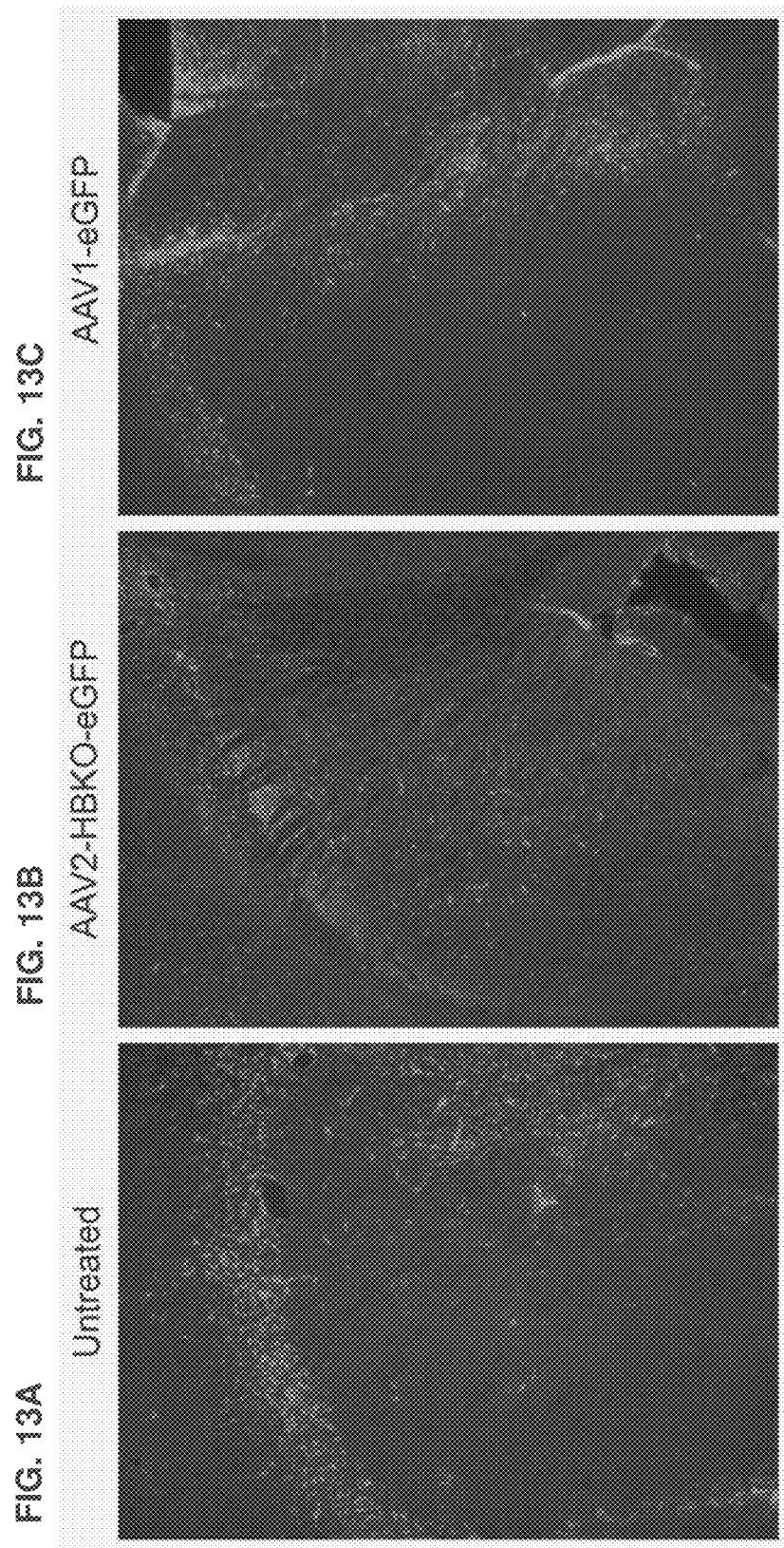

| AAV2 amino acid # | 484 | 487 | 532 | 585 | 588 |
|---|---|---|---|---|---|
| AAV2 | R | R | K | R | R |
| AAVrh8R | R | R | R | A | T |
| AAVrh8R amino acid # | 485 | 488 | 533 | 586 | 589 |

FIG. 14

| AAV2 amino acid # | 484 | 487 | 532 | 585 | 588 |
|---|---|---|---|---|---|
| AAV2 | R | R | K | R | R |
| AAVrh8R | R | R | R | A | T |
| AAVrh8R A586R | R | R | R | (R) | T |
| AAVrh8R R533A | R | R | (A) | A | T |
| AAVrh8R amino acid # | 485 | 488 | 533 | 586 | 589 |

FIG. 15

(+) Arg
AAVrh8R A586R (−) Arg
AAVrh8R R533A

NS1 cells
1E5 DRP/cell
(+) Adts149
AAVrh8R

HeLa cells
1E5 DRP/cell
(+) Adts149
AAVrh8R

| AAV amino acid # | | | | | | |
|---|---|---|---|---|---|---|
| AAV2 | 484 R | 487 R | 527 K | 532 K | 585 R | 588 R |
| AAV amino acid # | | | | | | |
| AAV1 | 485 R | 488 R | 528 K | 533 K | 586 S | 589 T |
| AAV6 | R | R | K | K | S | T |
| AAV9 | R | R | K | R | S | A |
| AAVrh8R | R | R | K | R | A | T |
| AAV amino acid # | | | | | | |
| AAV8 | 487 R | 490 R | 530 K | 535 R | 588 Q | 591 T |
| AAVrh10 | R | R | K | R | Q | A |

FIG. 20

AAV VECTORS FOR RETINAL AND CNS GENE THERAPY

CROSS REFERENCE TO RELATED APPLICATIONS

This application is a divisional of U.S. patent application Ser. No. 15/308,335, which adopts the international filing date of May 2, 2015, which is a National Phase application under 35 U.S.C. § 371 of International Application No. PCT/US2015/028966, filed May 2, 2015, which claims priority benefit of U.S. Provisional Application No. 61/988,131, filed May 2, 2014 and U.S. Provisional Application No. 62/114,575, filed Feb. 10, 2015, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792010410SEQLIST.txt, date recorded: Mar. 3, 2021, size: 85 KB).

FIELD OF THE INVENTION

The present invention relates to variant recombinant adeno-associated viral (rAAV) vectors for improved delivery to the eye and the CNS; for example for improved retinal gene therapy and improved CNS gene therapy.

BRIEF SUMMARY OF THE INVENTION

Retinal degenerative diseases are a promising focus for adeno-associated vector (AAV) mediated gene therapy. AAV vectors can mediate long term gene expression in the retina and elicit minimal immune responses making these vectors an attractive choice for gene delivery to the eye. The retina is a light sensitive tissue at the back of the eye that is composed of a variety of cell types including photoreceptor cells, retinal pigmented epithelial cells and retinal ganglion cells. The target cell type and vector delivery route for the AAV gene therapy vector will depend on the disease indication. For example, a Phase I clinical trial for age-related macular degeneration employs an intravitreal delivery of vector to achieve transduction of the retinal ganglion cells and a recent clinical trial for the treatment of patients with Leber Congenital Amaurosis Type 2, a form of retinitis pigmentosa, uses a subretinal delivery of the RPE65 gene to transduce the retinal pigmented epithelial cells.

In view of such utility, there is a need for developing novel agents and methods for improving AAV delivery to the eye.

Adeno-associated virus (AAV) based vectors have also become the preferred vector system for neurologic gene therapy, with an excellent safety record in multiple clinical trials (Kaplitt, M. G. et al. (2007) Lancet 369:2097-2105; Eberling, J. L. et al. (2008) Neurology 70:1980-1983; Fiandaca, M. S. et al. (2009) Neuroimage. 47 Suppl 2:T27-35). However, effective treatment of neurologic disorders has been largely hindered by problems associated with the delivery of AAV vectors to affected cell populations. This delivery issue has been especially problematic for disorders involving the central nervous system (CNS). Accordingly, there is a further need for enhancing AAV delivery to the CNS.

In some aspects, the invention provides methods for delivering a heterologous nucleic acid to the eye of an individual comprising administering a recombinant adeno-associated virus (rAAV) particle to the subretina of the individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In some embodiments, the rAAV particle comprises an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%. In some embodiments, the one or more amino acid substitutions increases the transduction efficiency by the rAAV particle of a cell in the eye or CNS. In some embodiments, the one or more amino acid substitutions increases the transduction efficiency by the rAAV particle of a cell in the eye or CNS by about at least 10%, about at least 25%, about at least 50%, about at least 75%, or about at least 100%, e.g., as compared to a reference rAAV capsid comprising a wild-type AAV capsid protein. In some embodiments, the cell of the eye is a retina cell, a photoreceptor cell, a retinal pigmented epithelial cells, bipolar cells, horizontal cells, amacrine cells, muller cells and/or ganglion cells. In some embodiments, the cell of the CNS is an oligodendrocyte, astrocyte, neuron, brain parenchyma cell, microglial cell, ependemal cell, and/or a Purkinje cell.

In some embodiments, the AAV particles of the invention comprise capsid with one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises a substitution at position R532. In some embodiments, the one or more amino acid substitutions comprises substitutions at position R484 and R487 or at positions R585 and R588, numbering based on VP1 of AAV2. In further embodiments, the one or more amino acid substitutions comprises R484A and R487A substitutions or R585A and R588A substitutions, numbering based on VP1 of AAV2. In further embodiments, the AAV capsid comprises amino acid substitutions R585A and R588A, numbering based on VP1 of AAV-2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments, the AAV particles of the invention comprise capsid with one or more amino acid substitutions is at position 485, 488, 528, 533, 586 or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an arginine or lysine residue with an alanine residue. In some embodiments, the amino acid substitution is at position 485, 488, 528, 533, or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments, the rAAV particle comprises an AAV1, AAV6, or AAV9 capsid and wherein the one or more amino acid substitutions is at position 485, 488, 528, 533, 586 and/or 589, numbering based on VP1 numbering of AAV1, AAV6, or AAV9; and/or wherein the rAAV particle comprises an AAV8 or AAVrh10 capsid and wherein the one or more amino acid substitutions is at position 487, 490, 535, 588 and/or 591, numbering based on VP1 numbering of AAV8 or AAVrh10.

In some embodiments, the AAV particles of the invention comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a rAAV vector comprising a heterologous nucleic acid encoding a therapeutic polypeptide or therapeutic nucleic acid. In some embodiments, the heterologous nucleic acid encodes a polypeptide selected from the group consisting of an anti-oxidant, a neurotrophic factor, an anti-apoptotic factor, an anti-angiogenic factor, and an anti-inflammatory factor. In further embodiments, the heterologous nucleic acid encodes a polypeptide selected from the group consisting of: Prph2, RPE65, AIPL1, GUCY2D, LCA5, CRX, CEP290, MYO 7a, Clarin, ABCA4, RDH12, IMPDH1, CRB1, LRAT, NMNAT1, TULP1, MERTK, RPGR, RP2, RPGRIP, CNGA3, CNGB3, GNAT2, GDNF, CNTF, FGF2, PEDF, EPO, BCL2, BCL-X, NFκB, Endostatin, Angiostatin, sFlt, sPDGF-R, IL10, anti-IL17, sIL17R, IL1-ra, anti-TGFβ, sTNF-R I, sTNF-R II, and IL4. In other embodiments, the heterologous nucleic acid encodes a therapeutic nucleic acid. In further embodiments, the therapeutic nucleic acid is an siRNA, an shRNA an RNAi, an miRNA, an antisense RNA, a ribozyme or a DNAzyme. In some embodiments, the rAAV vector is a self-complementary rAAV vector.

In some embodiments, the AAV particles of the invention comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a heterologous nucleic acid encoding a therapeutic polypeptide or therapeutic nucleic acid, wherein the heterologous nucleic acid is under the control of a promoter sequence that is expressed in the retina. In some embodiments, the heterologous nucleic acid is operably linked to a promoter suitable for expression of the therapeutic polypeptide or therapeutic nucleic acid in one or more retina cell types. In some embodiments, the retina cell is a photoreceptor cell, a retinal pigmented epithelial cells, bipolar cells, horizontal cells, amacrine cells, muller cells and/or ganglion cells. In some embodiments, the promoter is a rhodopsin kinase (RK) promoter, an opsin promoter, a Cytomegalovirus (CMV) promoter, a chicken β-actin (CBA) promoter.

In some embodiments, the AAV particles of the invention comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a heterologous nucleic acid for delivery of the heterologous nucleic acid to the retina of an individual. In some embodiments, the individual is a human. In some embodiments, the heterologous nucleic acid is used to treat an ocular disorder selected from the group consisting of: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis.

In some aspects, the invention provides methods for improving rAAV transduction of cells following subretinal delivery of a rAAV particle to the eye of an individual compared to transduction of cells with a rAAV comprising a wild-type capsid, the method comprising incorporating one or more amino acid substitutions in an AAV capsid protein at one or more positions that interacts with a heparan sulfate proteoglycan or at one or more positions corresponding to amino acids 484, 487, 527, 532, 585 or 588, numbering based on VP1 numbering of AAV2; wherein the rAAV particle comprises the rAAV capsid protein and a rAAV vector comprising the heterologous nucleic acid and at least one AAV terminal repeat.

In other aspects, the invention provides methods for improving expression of a heterologous nucleic acid following subretinal delivery of rAAV particles to the eye of an individual, the method comprising incorporating one or more amino acid substitutions in an AAV capsid protein at one or more positions that interacts with a heparan sulfate proteoglycan or at one or more positions corresponding to amino acids 484, 487, 532, 585 or 588, numbering based on VP1 numbering of AAV2; wherein the rAAV particle comprises the rAAV capsid protein and a rAAV vector comprising the heterologous nucleic acid and at least one AAV terminal repeat.

In some embodiments, the rAAV particles with improved transduction and/or improved expression of a heterologous nucleic acid comprise an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%.

In some embodiments, the rAAV particles with improved transduction and/or improved expression of a heterologous nucleic acid comprise capsid with one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises substitutions at position R484 and R487 or at positions R585 and R588, numbering based on VP1 of AAV2. In further embodiments, the one or more amino acid substitutions comprises R484A and R487A substitutions or R585A and R588A substitutions, numbering based on VP1 of AAV2. In further embodiments, the AAV capsid comprises amino acid substitutions R585A and R588A, numbering based on VP1 of AAV-2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments, the rAAV particles with improved transduction and/or improved expression of a heterologous nucleic acid comprise capsid with one or more amino acid substitutions is at position 485, 488, 528, 533, 586 or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an alanine residue for an arginine or lysine residue. In some embodiments, the amino acid substitution is at position 485, 488, 528, 533, or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments, the rAAV particles with improved transduction and/or improved expression of a heterologous nucleic acid comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a rAAV vector comprising a heterologous nucleic acid encoding a therapeutic polypeptide or therapeutic nucleic acid. In some embodiments, the heterologous nucleic acid encodes a polypeptide selected from the group consisting of an anti-oxidant, a neurotrophic factor, an anti-apoptotic factor, an anti-angiogenic factor, and an anti-inflammatory factor. In further embodiments, the heterologous nucleic acid encodes a polypeptide selected from the group consisting of: Prph2, RPE65, AIPL1, GUCY2D, LCA5, CRX, CEP290, MYO 7a, Clarin, ABCA4, RDH12, IMPDH1, CRB1, LRAT, NMNAT1, TULP1, MERTK, RPGR, RP2, RPGRIP, CNGA3, CNGB3, GNAT2, GDNF, CNTF, FGF2, PEDF, EPO, BCL2, BCL-X, NFκB, Endostatin, Angiostatin, sFlt, sPDGF-R, IL10, anti-IL17, sIL17R, IL1-ra, anti-TGFβ, sTNF-R I, sTNF-R II, and IL4. In other embodiments, the heterologous nucleic acid encodes a therapeutic nucleic acid. In further embodiments, the therapeutic nucleic acid is an siRNA, an shRNA an RNAi, an miRNA, an antisense RNA, a ribozyme or a DNAzyme. In some embodiments, the rAAV vector is a self-complementary rAAV vector.

In some embodiments, the rAAV particles with improved transduction and/or improved expression of a heterologous nucleic acid comprise a capsid comprising one or more amino acid substitutions which alter binding to HSPG (e.g., reduces or ablates binding to HSPG) or at one or more positions corresponding to amino acids 484, 487, 532, 585 or 588, numbering based on VP1 numbering of AAV2 and a heterologous nucleic acid encoding a therapeutic polypeptide or therapeutic nucleic acid, wherein the heterologous nucleic acid is under the control of a promoter sequence that is expressed in the retina. In some embodiments, the heterologous nucleic acid is operably linked to a promoter suitable for expression of the therapeutic polypeptide or therapeutic nucleic acid in one or more retina cell types. In some embodiments, the retina cell is a photoreceptor cell, a retinal pigmented epithelial cell, and/or a ganglion cell. In some embodiments, the promoter is a rhodopsin kinase (RK) promoter, an opsin promoter, a Cytomegalovirus (CMV) promoter, a chicken β-actin (CBA) promoter.

In some embodiments, the rAAV particles with improved transduction and/or improved expression of a heterologous nucleic acid comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a heterologous nucleic acid for delivery of the heterologous nucleic acid to the retina of an individual. In some embodiments, the individual is a human. In some embodiments, the heterologous nucleic acid is used to treat an ocular disorder selected from the group consisting of: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis.

In some aspects, the invention provides methods to treat an ocular disorder in an individual (e.g., a human) comprising delivery of a composition comprising rAAV particles to the retina of an individual, wherein the rAAV particles comprise a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV terminal repeat. In some embodiments, the rAAV particle comprises an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%.

In some embodiments, the methods comprises subretinal delivery of rAAV particles comprising a rAAV vector encoding a heterologous nucleic acid used in treatment of the ocular disorder in an individual (e.g., a human), wherein the rAAV particles comprise capsid with one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises substitutions at position R484 and R487 or at positions R585 and R588, numbering based on VP1 of AAV2. In further embodiments, the one or more amino acid substitutions comprises R484A and R487A substitutions or R585A and R588A substitutions, numbering based on VP1 of AAV2. In further embodiments, the AAV capsid comprises amino acid substitutions R585A and R588A, numbering based on VP1 of AAV-2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments, the methods comprises subretinal delivery of rAAV particles comprising a rAAV vector encoding a heterologous nucleic acid used in treatment of the ocular disorder in an individual (e.g., a human), wherein the rAAV particles comprise capsid with one or more amino acid substitutions is at position 485, 488, 528, 533, 586 or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an alanine residue for an arginine or lysine residue. In some embodiments, the amino acid substitution is at position 485, 488, 528, 533, or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments, the methods comprises subretinal delivery of rAAV particles comprising a rAAV vector encoding a heterologous nucleic acid used in treatment of the ocular disorder in an individual (e.g., a human) and a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2. In some embodiments, the heterologous nucleic acid encodes a polypeptide selected from the group consisting of an anti-oxidant, a neurotrophic factor, an anti-apoptotic factor, an anti-angiogenic factor, and an anti-inflammatory factor. In further embodiments, the heterologous nucleic acid encodes a polypeptide selected from the group consisting of: Prph2, RPE65, AIPL1, GUCY2D, LCA5, CRX, CEP290, MYO 7a, Clarin, ABCA4, RDH12, IMPDH1, CRB1, LRAT, NMNAT1, TULP1, MERTK, RPGR, RP2, RPGRIP, CNGA30, CNGB3, GNAT2, GDNF, CNTF, FGF2, PEDF, EPO, BCL2, BCL-X, NFκB, Endostatin, Angiostatin, sFlt, sPDGF-R, IL10, anti-IL17, sIL17R, IL1-ra, anti-TGFβ, sTNF-R I, sTNF-R II, and IL4. In other embodiments, the heterologous nucleic acid encodes a therapeutic nucleic acid. In further embodiments, the therapeutic nucleic acid is an siRNA, an shRNA an RNAi, an miRNA, an antisense RNA, a ribozyme or a DNAzyme. In some embodiments, the rAAV vector is a self-complementary rAAV vector.

In some embodiments, the methods comprises subretinal delivery of rAAV particles comprising a rAAV vector encoding a heterologous nucleic acid used in treatment of the ocular disorder in an individual (e.g., a human) and a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2, wherein the heterologous nucleic acid is under the control of a promoter sequence that is expressed in the retina. In some embodiments, the heterologous nucleic acid is operably linked to a promoter suitable for expression of the therapeutic polypeptide or therapeutic nucleic acid in one or more retina cell types. In some embodiments, the retina cell is a photoreceptor cell, a retinal pigmented epithelial cell, and/or a ganglion cell. In some embodiments, the promoter is a rhodopsin kinase (RK) promoter, an opsin promoter, a Cytomegalovirus (CMV) promoter, a chicken β-actin (CBA) promoter.

In some embodiments, the methods comprises subretinal delivery of rAAV particles comprising a rAAV vector encoding a heterologous nucleic acid used in treatment of the ocular disorder in an individual (e.g., a human) and a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2, wherein the ocular disorder selected from the group consisting of: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis.

In some embodiments, the methods comprises subretinal delivery of a composition comprising rAAV particles, wherein the rAAV particles comprise a rAAV vector encoding a heterologous nucleic acid used in treatment of the ocular disorder in an individual (e.g., a human) and a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2. In some embodiments, the concentration of the particles in the composition is about $1\times10^6$ DRP/ml to about $1\times10^{14}$ DRP/ml. In some embodiments, the composition of rAAV particles is effective in treating the individual's visual function. In some embodiments, visual function is assessed by microperimetry, dark-adapted perimetry, assessment of visual mobility, visual acuity, ERG, or reading assessment. In some embodiments, the method results in an improvement in the individual's visual function. In some embodiments, the method results in the prevention of or a slowing of the progression of decline of the human's visual function due to progression of the ocular disorder.

In some aspects, the invention provides systems for subretinal delivery of a vector to an eye of an individual, comprising a) a composition comprising an effective amount of rAAV particles, wherein i) a capsid protein of the rAAV particles comprises one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and ii) the vector comprises a heterologous nucleic acid encoding a therapeutic polypeptide or therapeutic RNA and at least one AAV terminal repeat; and b) a device for retinal delivery of the rAAV. In some embodiments, the device comprises a fine-bore cannula and a syringe, wherein the fine bore cannula is 27 to 45 gauge. In some embodiments, the composition of rAAV particles is contained within the syringe. In some embodiments, the cannula is attached to the syringe. In some embodiments, the concentration of the particles in the composition is about $1\times10^6$ DRP/ml to about $1\times10^{14}$ DRP/ml.

In some embodiments, the rAAV particles of the system comprise an AAV2 capsid comprise one or more amino acid substitutions that alter HSPG binding (e.g., reduces or ablates binding). In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%. In some embodiments, the one or more amino acid substitutions increases the transduction efficiency by the rAAV particle of a cell in the eye or CNS. In some embodiments, the one or more amino acid substitutions increases the transduction efficiency by the rAAV particle of a cell in the eye or CNS by about at least 10%, about at least 25%, about at least 50%, about at least 75%, or about at least 100%, e.g., as compared to a reference rAAV capsid comprising a wild-type AAV capsid protein. In some embodiments, the cell of the eye is a retina cell, a photoreceptor cell, a retinal pigmented epithelial cells, bipolar cells, horizontal cells, amacrine cells, muller cells and/or ganglion cells. In some embodiments, the cell of the CNS is an oligodendrocyte, astrocyte, neuron, brain parenchyma cell, microglial cell, ependemal cell, and/or a Purkinje cell.

In some embodiments, the rAAV particles of the system comprise an AAV2 capsid comprise one or more amino acid substitutions that alter HSPG binding (e.g., reduces or ablates binding). In some embodiments, the one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises substitutions at position R484 and R487 or at positions R585 and R588, numbering based on VP1 of AAV2. In further embodiments, the one or more amino acid substitutions comprises R484A and R487A substitutions or R585A and R588A substitutions, numbering based on VP1 of AAV2. In further embodiments, the AAV capsid comprises amino acid substitutions R585A and R588A, numbering based on VP1 of AAV-2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments, the rAAV particles of the system comprise an AAV2 capsid comprise one or more amino acid substitutions that alter HSPG binding (e.g., reduces or ablates binding). In some embodiments, the one or more amino acid substitutions is at position 485, 488, 528, 533, 586 or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an alanine residue for an arginine or lysine residue. In some embodiments, the amino acid substitution is at position 485, 488, 528, 533, or 589, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments, the rAAV particles of the system comprise an AAV capsid with one or more amino acid substitutions that alter HSPG binding (e.g., reduces or ablates binding) or at one or more positions corresponding to amino acids 484, 487, 527, 532, 585 or 588, numbering based on VP1 numbering of AAV2 and a rAAV vector comprising a heterologous nucleic acid. In some embodiments, the heterologous nucleic acid encodes a therapeutic polypeptide or therapeutic nucleic acid. In some embodiments, the heterologous nucleic acid encodes a polypeptide selected from the group consisting of an anti-oxidant, a neurotrophic factor, an anti-apoptotic factor, an anti-angiogenic factor, and an anti-inflammatory factor. In further embodiments, the heterologous nucleic acid encodes a polypeptide selected from the group consisting of: Prph2, RPE65, AIPL1, GUCY2D, LCA5, CRX, CEP290, MYO 7a, Clarin, ABCA4, RDH12, IMPDH1, CRB1, LRAT, NMNAT1, TULP1, MERTK, RPGR, RP2, RPGRIP, CNGA3, CNGB3, GNAT2, GDNF, CNTF, FGF2, PEDF, EPO, BCL2, BCL-X, NFκB, Endostatin, Angiostatin, sFlt, sPDGF-R, IL10, anti-IL17, sIL17R, IL1-ra, anti-TGFβ, sTNF-R I, sTNF-R II, and IL4. In other embodiments, the heterologous nucleic acid encodes a therapeutic nucleic acid. In further embodiments, the therapeutic nucleic acid is an siRNA, an RNAi, an miRNA, an antisense RNA, a ribozyme or a DNAzyme. In some embodiments, the rAAV vector is a self-complementary rAAV vector.

In some embodiments, the rAAV particles of the system comprise an AAV capsid with one or more amino acid substitutions that alter HSPG binding (e.g., reduces or ablates binding) or at one or more positions corresponding to amino acids 484, 487, 527, 532, 585 or 588, numbering based on VP1 numbering of AAV2 and a rAAV vector comprising a heterologous nucleic acid, wherein the heterologous nucleic acid is under the control of a promoter sequence that is expressed in the retina. In some embodiments, the heterologous nucleic acid is operably linked to a promoter suitable for expression of the therapeutic polypeptide or therapeutic nucleic acid in one or more retina cell types. In some embodiments, the retina cell is a photoreceptor cell, a retinal pigmented epithelial cell, and/or a ganglion cell. In some embodiments, the promoter is a rhodopsin kinase (RK) promoter, an opsin promoter, a Cytomegalovirus (CMV) promoter, a chicken β-actin (CBA) promoter.

In some embodiments, the rAAV particles of the system comprise an AAV capsid with one or more amino acid substitutions that alter HSPG binding (e.g., reduces or ablates binding) or at one or more positions corresponding to amino acids 484, 487, 527, 532, 585 or 588, numbering based on VP1 numbering of AAV2 and a rAAV vector comprising a heterologous nucleic acid are used for delivery of the heterologous nucleic acid to the retina of an individual. In some embodiments, the individual is a human. In some embodiments, the heterologous nucleic acid is used to treat an ocular disorder selected from the group consisting of: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis.

In some aspects, the invention provides a method for delivering a heterologous nucleic acid to the central nervous system (CNS) of an individual comprising administering a recombinant adeno-associated virus (rAAV) particle to the CNS of the individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In some aspects, the invention provides a method for improving rAAV transduction of cells in the central nervous system (CNS) of an individual compared to transduction of cells with a rAAV comprising a wild-type capsid, the method comprising administering a recombinant adeno-associated virus (rAAV) particle to the CNS of the individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV inverted terminal repeat. In further aspects, the invention provides a method for improving expression of a heterologous nucleic acid in the central nervous system (CNS) of an individual, the method comprising administering a recombinant adeno-associated virus (rAAV) particle to the CNS of the individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In still further aspects, the invention provides a method to treat a disorder of the central nervous system (CNS) of an individual comprising administering an effective amount of a composition comprising a rAAV particle to the CNS of the individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat.

In some embodiments of the above aspects and embodiments, the heterologous nucleic acid is expressed at an increased level of expression, as compared to the level of expression of a heterologous nucleic acid of a rAAV particle comprising a reference rAAV capsid. In some embodiments, the expression of the nucleic acid is increased by at least about 10%, at least about 25%, at least about 50%, at least about 75%, or at least about 100%. In some embodiments, the rAAV particle causes reduced neuroinflammation, as compared to a rAAV particle comprising a reference rAAV capsid. In some embodiments, the neuroinflammation is reduced by at least about 10%, at least about 25%, at least about 50%, at least about 75%, or at least about 100%. In some embodiments, the rAAV particle comprises an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan, as compared to the binding of a rAAV particle comprising a reference rAAV capsid to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%. In some embodiments, the one or more amino acid substitutions reduces binding of the rAAV particle to the heparan sulfate proteoglycan by about at least 10%, about at least 25%, about at least 50%, about at least 75%, or about at least 100%, as compared to the binding of a rAAV particle comprising a reference capsid to the heparan sulfate proteoglycan. In some embodiments, a reference rAAV capsid comprises a wild-type rAAV capsid or capsid protein. In some embodiments, a reference rAAV capsid comprises a rAAV capsid or capsid protein that lacks one or more amino acid substitutions at one or more positions that interacts with a heparan sulfate proteoglycan. In some embodiments, the one or more amino acid substitutions increases the transduction efficiency by the rAAV particle of a cell in the eye or CNS. In some embodiments, the one or more amino acid substitutions increases the transduction efficiency by the rAAV particle of a cell in the eye or CNS by about at least 10%, about at least 25%, about at least 50%, about at least 75%, or about at least 100%, e.g., as compared to a reference rAAV capsid comprising a wild-type AAV capsid protein. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments of the above aspects and embodiments, the administration comprises direct spinal cord injection and/or intracerebral administration. In some embodiments, the intracerebral administration is at a site selected from the group consisting of the cerebrum, medulla, pons, cerebellum, intracranial cavity, meninges surrounding the brain, dura mater, arachnoid mater, pia mater, cerebrospinal fluid (CSF) of the subarachnoid space surrounding the brain, deep cerebellar nuclei of the cerebellum, ventricular system of the cerebrum, subarachnoid space, striatum, cortex, septum, thalamus, hypothalamus, and the parenchyma of the brain. In some embodiments, the administration is intracerebroventricular injection into at least one cerebral lateral ventricle. In some embodiments, the administration is intrathecal injection in the cervical, thoracic, and/or lumbar region. In some embodiments, the administration is intrastriatal injection. In some embodiments, the administration is intrathalamic injection. In some embodiments, the administration is intraparenchymal injection. In some embodiments, the administration comprises direct spinal cord injection, intracranial, and/or intracerebral administration. In some embodiments, the rAAV particle is administered at a single site.

In some embodiments of the above aspects and embodiments, the rAAV particle is delivered by stereotactic delivery. In some embodiments, the rAAV particle is delivered by convection enhanced delivery. In some embodiments, the rAAV particle is administered using a CED delivery system. In some embodiments, the CED delivery system comprises a cannula and/or a pump. In some embodiments, the cannula is a reflux-resistant cannula or a stepped cannula. In some embodiments, the pump is a manual pump. In some embodiments, the pump is an osmotic pump. In some embodiments, the pump is an infusion pump.

In some embodiments of the above aspects and embodiments, the heparan sulfate proteoglycan is expressed on one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heparan sulfate proteoglycan is expressed on a neuron.

In some embodiments of the above aspects and embodiments, the heterologous nucleic acid is expressed in one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heterologous nucleic acid is expressed in a neuron. In some embodiments, the heterologous nucleic acid is exclusively expressed in neurons.

In some embodiments of the above aspects and embodiments, the one or more amino acid substitutions is at 448, 451, 484, 487, 527, 532, 585 and/or 588, numbering based on VP1 numbering of AAV2. In some embodiments, the one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In some embodiments, the one or more amino acid substitutions comprises substitution of an arginine or lysine residue. In some embodiments, the one or more amino acid substitutions comprises substitution of an arginine or lysine residue with an alanine residue. In some embodiments, the one or more amino acid substitutions comprises a substitution at position R347, R350, K390, K395, R448, R451, R484, R487, K527, K532, R585 and/or R588, numbering based on VP1 of AAV2. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises a R347A, R350A, K390A, K395A, R448A, R451A, R484A, R487A, K527A, K532A, R585A and/or R588A substitution, numbering based on VP1 of AAV2. In some embodiments, the one or more amino acid substitutions comprises substitutions at position R484 and R487 or at positions R585 and R588, numbering based on VP1 of AAV2. In some embodiments, the one or more amino acid substitutions comprises R484A and R487A substitutions or R585A and R588A substitutions, numbering based on VP1 of AAV2. In some embodiments, the AAV capsid comprises amino acid substitutions R585A and R588A, numbering based on VP1 of AAV2. In some embodiments, the AAV capsid comprises amino acid substitutions K532A, numbering based on VP1 of AAV2.

In some embodiments of the above aspects and embodiments, the one or more amino acid substitutions is at position 485, 488, 528, 533, 586 or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an alanine residue for an arginine or lysine residue. In some embodiments, the amino acid substitution is at position 485, 488, 528, 533, or 589, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments of the above aspects and embodiments, the heterologous nucleic acid encodes a therapeutic polypeptide or therapeutic nucleic acid. In some embodiments, the heterologous nucleic acid encodes a CNS-associated gene. In some embodiments, the heterologous nucleic acid encodes a polypeptide selected from the group consisting of an enzyme, a neurotrophic factor, a polypeptide that is deficient or mutated in an individual with a CNS-related disorder, an antioxidant, an anti-apoptotic factor, an anti-angiogenic factor, and an anti-inflammatory factor, alpha-synuclein, acid beta-glucosidase (GBA), beta-galactosidase-1 (GLB1), iduronate 2-sulfatase (IDS), galactosylceramidase (GALC), a mannosidase, alpha-D-mannosidase (MAN2B1), beta-mannosidase (MANBA), pseudoarylsulfatase A (ARSA), N-acetylglucosamine-1-phosphotransferase (GNPTAB), acid sphingomyelinase (ASM), Niemann-Pick C protein (NPC1), acid alpha-1,4-glucosidase (GAA), hexosaminidase beta subunit, HEXB, N-sulfoglucosamine sulfohydrolase (MPS3A), N-alpha-acetylglucosaminidase (NAGLU), heparin acetyl-CoA, alpha-glucosaminidase N-acetyltransferase (MPS3C), N-acetylglucosamine-6-sulfatase (GNS), alpha-N-acetylgalactosaminidase (NAGA), beta-glucuronidase (GUSB), hexosaminidase alpha subunit (HEXA), huntingtin (HTT), lysosomal acid lipase (LIPA), Aspartylglucosaminidase, Alpha-galactosidase A, Palmitoyl protein thioesterase, Tripeptidyl peptidase, Lysosomal transmembrane protein, Cysteine transporter, Acid ceramidase, Acid alpha-L-fucosidase, cathepsin A, alpha-L-iduronidase, Arylsulfatase B, Arylsulfatase A, N-acetylgalactosamine-6-sulfate, Acid beta-galactosidase, or alpha-neuramidase. In some embodiments, the heterologous nucleic acid encodes a polypeptide selected from the group consisting of neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), amino acid decarboxylase (AADC), an anti-oxidant, an anti-angiogenic polypeptide, an anti-inflammatory polypeptide, and aspartoacylase (ASPA). In some embodiments, the heterologous nucleic acid encodes a therapeutic nucleic acid. In some embodiments, the therapeutic nucleic acid is an siRNA, an shRNA, an RNAi, an miRNA, an antisense RNA, a ribozyme or a DNAzyme. In some embodiments, the heterologous nucleic acid is under the control of a promoter sequence that is expressed in one or more cells of the CNS. In some embodiments, the heterologous nucleic acid is under the control of a promoter sequence selected from the group consisting of a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a β-actin promoter. In some embodiments, the heterologous nucleic acid is operably linked to a promoter suitable for expression of the therapeutic polypeptide or therapeutic nucleic acid in one or more cells of the CNS. In some embodiments, the one or more cells of the CNS comprise one or more cells of the brain. In some embodiments, the one or more cells of the CNS is an oligodendrocyte, astrocyte, neuron, brain parenchyma cell, microglial cell, ependemal cell, and/or a Purkinje cell. In some embodiments, the cell of the brain is a neuron.

In some embodiments of the above aspects and embodiments, the rAAV vector is a self-complementary rAAV vector. In some embodiments, the vector comprises first nucleic acid sequence encoding the heterologous nucleic acid and a second nucleic acid sequence encoding a complement of the nucleic acid, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the individual is a human.

In some embodiments of the above aspects and embodiments, the heterologous nucleic acid encodes a therapeutic polypeptide or a therapeutic nucleic acid used to treat a disorder of the CNS. In some embodiments, the disorder of the CNS is a lysosomal storage disease (LSD), Huntington's disease, epilepsy, Parkinson's disease, Alzheimer's disease, stroke, corticobasal degeneration (CBD), corticogasal ganglionic degeneration (CBGD), frontotemporal dementia (FTD), multiple system atrophy (MSA), progressive supranuclear palsy (PSP) or cancer of the brain. In some embodiments, the disorder is a lysosomal storage disease selected from the group consisting of Aspartylglusoaminuria, Fabry, Infantile Batten Disease (CNL1), Classic Late Infantile Batten Disease (CNL2), Juvenile Batten Disease (CNL3), Batten form CNL4, Batten form CNL5, Batten form CNL6, Batten form CNL7, Batten form CNL8, Cystinosis, Farber, Fucosidosis, Galactosidosialidosis, Gaucher disease type 1, Gaucher disease type 2, Gaucher disease type 3, GM1 gangliosidosis, Hunter disease, Krabbe disease, a mannosidosis disease, β mannosidosis disease, Maroteaux-Lamy, metachromatic leukodystrophy disease, Morquio A, Morquio B, mucolipidosisII/III disease, Niemann-Pick A disease, Niemann-Pick B disease, Niemann-Pick C disease, Pompe disease, Sandhoff disease, Sanfillipo A disease, Sanfillipo B disease, Sanfillipo C disease, Sanfillipo D disease, Schindler disease, Schindler-Kanzaki, sialidosis, Sly disease, Tay-Sachs disease, and Wolman disease. In some embodiments, the disorder of the CNS is Huntington's disease or Parkinson's disease.

In some aspects, the invention provides a method to treat Huntington's Disease in an individual comprising administering an effective amount a composition comprising a recombinant adeno-associated virus (rAAV) particle to the striatum of the individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat. In some embodiments, the heterologous nucleic acid encodes a therapeutic polypeptide or therapeutic nucleic acid. In some embodiments, the therapeutic polypeptide is a huntingtin polypeptide or a fragment thereof. In some embodiments, the huntingtin polypeptide or a fragment thereof is a functional huntingtin polypeptide or a functional fragment thereof. In some embodiments, the therapeutic nucleic acid comprises an RNAi directed to huntingtin. In some embodiments, the RNAi is a miRNA.

In some aspects, the invention provides a method to treat Parkinson's Disease in an individual comprising administering an effective amount a composition comprising a recombinant adeno-associated virus (rAAV) particle to the striatum of the individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat. In some embodiments, the heterologous nucleic acid encodes a therapeutic polypeptide or therapeutic nucleic acid. In some embodiments, the therapeutic polypeptide is TH, GTPCII, GDNF, BDNF, and/or AADC; or a fragment thereof. In some embodiments, the therapeutic polypeptide is AADC or a fragment thereof.

In some embodiments of the above aspects and embodiments, the heterologous nucleic acid is expressed at an increased level of expression, as compared to the level of expression of a heterologous nucleic acid of a rAAV particle comprising a reference rAAV capsid. In some embodiments, the rAAV particle causes reduced neuroinflammation, as compared to a rAAV particle comprising a reference rAAV capsid. In some embodiments, the rAAV particle comprises an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan, as compared to the binding of a rAAV particle comprising a reference rAAV capsid to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%. In some embodiments, the one or more amino acid substitutions reduces binding of the rAAV particle to the heparan sulfate proteoglycan by about at least 10%, about at least 25%, about at least 50%, about at least 75%, or about at least 100%, as compared to the binding of a rAAV particle comprising a reference capsid to the heparan sulfate proteoglycan. In some embodiments, a reference rAAV capsid comprises a wild-type rAAV capsid or capsid protein. In some embodiments, a reference rAAV capsid comprises a rAAV capsid or capsid protein that lacks one or more amino acid substitutions at one or more positions that interacts with a heparan sulfate proteoglycan.

In some embodiments of the above aspects and embodiments, the rAAV particle is delivered by stereotactic delivery. In some embodiments, the rAAV particle is delivered by convection enhanced delivery. In some embodiments, the rAAV particle is administered using a CED delivery system. In some embodiments, the cannula is a reflux-resistant cannula or a stepped cannula. In some embodiments, the CED delivery system comprises a cannula and/or a pump. In some embodiments, the rAAV particle is administered using a CED delivery system. In some embodiments, the pump is a manual pump. In some embodiments, the pump is an osmotic pump. In some embodiments, the pump is an infusion pump.

In some embodiments of the above aspects and embodiments, the heparan sulfate proteoglycan is expressed on one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heparan sulfate proteoglycan is expressed on a neuron.

In some embodiments of the above aspects and embodiments, the heterologous nucleic acid is expressed in one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heterologous nucleic acid is expressed in a neuron. In some embodiments, the heterologous nucleic acid is exclusively expressed in neurons.

In some embodiments of the above aspects and embodiments, the one or more amino acid substitutions is at position 484, 487, 527, 532, 585 or 588, numbering based on VP1 numbering of AAV2. In some embodiments, the numbering is based on the VP1 of AAV2 comprising the amino acid sequence of SEQ ID NO:1. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In some embodiments, the one or more amino acid substitutions comprises substitution of an arginine or lysine residue. In some embodiments, the one or more amino acid substitutions comprises substitution of an arginine or lysine residue with an alanine residue. In some embodiments, the one or more amino acid substitutions comprises a substitution at position R347, R350, K390, K395, R448, R451, R484, R487, K527, K532, R585 and/or R588, numbering based on VP1 of AAV2. In some embodiments, the one or more amino acid substitutions comprises a substitution at position R484, R487, K527, K532, R585 and/or R588, numbering based on VP1 of AAV2. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises a R347A, R350A, K390A, K395A, R448A, R451A, R484A, R487A, K527A, K532A, R585A and/or R588A substitution, numbering based on VP1 of AAV2. In some embodiments, the one or more amino acid substitutions comprises substitutions at position R484 and R487 or at positions R585 and R588, numbering based on VP1 of AAV2. In some embodiments, the one or more amino acid substitutions comprises R484A and R487A substitutions or R585A and R588A substitutions, numbering based on VP1 of AAV2. In some embodiments, the AAV capsid comprises amino acid substitutions R585A and R588A, numbering based on VP1 of AAV2. In some embodiments, the AAV capsid comprises amino acid substitutions K532A, numbering based on VP1 of AAV2.

In some embodiments of the above aspects and embodiments, the one or more amino acid substitutions is at position 485, 488, 528, 533, 586 or 589, numbering based on VP1 numbering of AAVrh8R. In some embodiments, the AAV particles of the invention comprise capsid with one or more amino acid substitutions is at position 485, 488, 528, or 533, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an alanine residue for an arginine or lysine residue. In some embodiments, the amino acid substitution is at position 485, 488, 528, 533, or 589, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments of the above aspects and embodiments, the heterologous nucleic acid is under the control of a promoter sequence that is expressed in one or more cells of the CNS. In some embodiments, the heterologous nucleic acid is under the control of a promoter sequence selected from the group consisting of a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a β-actin promoter. In some embodiments, the heterologous nucleic acid is operably linked to a promoter suitable for expression of the therapeutic polypeptide or therapeutic nucleic acid in one or more cells of the CNS. In some embodiments, the one or more cells of the CNS comprise one or more cells of the brain. In some embodiments, the one or more cells of the CNS is an oligodendrocyte, astrocyte, neuron, brain parenchyma cell, microglial cell, ependemal cell, and/or a Purkinje cell. In some embodiments, the cell of the brain is a neuron.

In some embodiments of the above aspects and embodiments, the rAAV vector is a self-complementary rAAV vector. In some embodiments, the vector comprises first nucleic acid sequence encoding the heterologous nucleic acid and a second nucleic acid sequence encoding a complement of the nucleic acid, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the individual is a human.

In some aspects, the invention provides a kit for use in any of the above embodiments, comprising a recombinant adeno-associated virus (rAAV) particle, wherein the rAAV particle comprises a) a rAAV capsid comprising rAAV capsid proteins comprising one or more amino acid substitutions at one or more positions that interact with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In some aspects, the invention provides a kit for delivering a heterologous nucleic acid to the central nervous system (CNS) of an individual comprising a composition comprising a recombinant adeno-associated virus (rAAV) particle, wherein the rAAV particle comprises a) a rAAV capsid comprising rAAV capsid proteins comprising one or more amino acid substitutions at one or more positions that interact with a heparan sulfate proteoglycan, and b) a rAAV vector comprising the heterologous nucleic acid and at least one AAV inverted terminal repeat. In some aspects, the invention provides a kit for treating a central nervous system (CNS) disorder in an individual comprising a composition comprising a recombinant adeno-associated virus (rAAV) particle, wherein the rAAV particle comprises a) a rAAV capsid comprising rAAV capsid proteins comprising one or more amino acid substitutions at one or more positions that interact with a heparan sulfate proteoglycan, and b) a rAAV vector comprising the heterologous nucleic acid for treating a CNS disorder and at least one AAV inverted terminal repeat.

In some embodiments of the above aspects and embodiments, the CNS disorder is Huntington's disease. In some embodiments, the heterologous nucleic acid encodes a therapeutic polypeptide or therapeutic nucleic acid. In some embodiments, the therapeutic polypeptide is a huntingtin polypeptide or a fragment thereof. In some embodiments, the huntingtin polypeptide or a fragment thereof is a functional huntingtin polypeptide or a functional fragment thereof. In some embodiments, the therapeutic nucleic acid comprises an RNAi directed to huntingtin. In some embodiments, the RNAi is a miRNA. In some embodiments, the CNS disorder is Parkinson's disease. In some embodiments, the heterologous nucleic acid encodes a therapeutic polypeptide or therapeutic nucleic acid. In some embodiments, the therapeutic polypeptide is TH, GTPCII, GDNF, BDNF, and/or AADC; or a fragment thereof. In some embodiments, the therapeutic polypeptide is AADC or a fragment thereof.

In some aspects, the invention provides a recombinant adeno-associated virus (rAAV) particle for use in any of the above embodiments. In some aspects, the invention provides a recombinant adeno-associated virus (rAAV) particle for delivering a heterologous nucleic acid to the central nervous system (CNS) of an individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In some aspects, the invention provides a recombinant adeno-associated virus (rAAV) particle for treating a disorder of the central nervous system (CNS) of an individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat. In some aspects, the invention provides a recombinant adeno-associated virus (rAAV) particle for treating Huntington's Disease in an individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat, wherein the rAAV particle is formulated for delivery to the striatum. In some aspects, the invention provides a recombinant adeno-associated virus (rAAV) particle for treating Parkinson's Disease in an individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat, wherein the rAAV particle is formulated for delivery to the striatum. In some aspects, the invention provides a recombinant adeno-associated virus (rAAV) particle for treating Huntington's Disease in an individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat, wherein the rAAV particle is formulated for single site delivery (e.g., to the CNS of an individual). In some aspects, the invention provides a recombinant adeno-associated virus (rAAV) particle for treating Parkinson's Disease in an individual, wherein the rAAV particle comprises a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat, wherein the rAAV particle is formulated for single site delivery (e.g., to the CNS of an individual).

In some embodiments of the above aspects and embodiments, the heterologous nucleic acid is expressed at an increased level of expression, as compared to the level of expression of a heterologous nucleic acid of a rAAV particle comprising a reference rAAV capsid. In some embodiments, the rAAV particle causes reduced neuroinflammation, as compared to a rAAV particle comprising a rAAV capsid comprising a reference capsid. In some embodiments, the rAAV particle comprises an AAV serotype 2 (AAV2) capsid. In some embodiments, the one or more amino acid substitutions reduces binding of the rAAV particle to the heparan sulfate proteoglycan. In some embodiments, the one or more amino acid substitutions reduces binding of the rAAV particle to the heparan sulfate proteoglycan, as compared to the binding of a rAAV particle comprising a reference rAAV capsid to the heparan sulfate proteoglycan. In some embodiments, the one or more amino acid substitutions reduces binding of the rAAV particle to the heparan sulfate proteoglycan by about at least 10%, about at least 25%, about at least 50%, about at least 75%, or about at least 100%. In some embodiments, the one or more amino acid substitutions reduces binding of the rAAV particle to the heparan sulfate proteoglycan by about at least 10%, about at least 25%, about at least 50%, about at least 75%, or about at least 100%, as compared to the binding of a rAAV particle comprising a reference capsid to the heparan sulfate proteoglycan. In some embodiments, a reference rAAV capsid comprises a wild-type rAAV capsid or capsid protein. In some embodiments, a reference rAAV capsid comprises a rAAV capsid or capsid protein that lacks one or more amino acid substitutions at one or more positions that interacts with a heparan sulfate proteoglycan.

In some embodiments of the above aspects and embodiments, the heparan sulfate proteoglycan is expressed on one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heparan sulfate proteoglycan is expressed on a neuron.

In some embodiments of the above aspects and embodiments, the heterologous nucleic acid is expressed in one or more cells of the CNS. In some embodiments, the one or more cells of the CNS is an oligodendrocyte, astrocyte, neuron, brain parenchyma cell, microglial cell, ependemal cell, and/or a Purkinje cell. In some embodiments, the heterologous nucleic acid is expressed in a neuron. In some embodiments, the heterologous nucleic acid is exclusively expressed in neurons.

In some embodiments of the above aspects and embodiments, the one or more amino acid substitutions is at position 484, 487, 527, 532, 585 or 588, numbering based on VP1 numbering of AAV2. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In some embodiments, the one or more amino acid substitutions comprises substitution of an arginine or lysine residue. In some embodiments, the one or more amino acid substitutions comprises substitution of an arginine or lysine residue with an alanine residue. In some embodiments, the one or more amino acid substitutions comprises a substitution at position R347, R350, K390, K395, R448, R451, R484, R487, K527, K532, R585 and/or R588, numbering based on VP1 of AAV2. In some embodiments, the one or more amino acid substitutions comprises a substitution at position R484, R487, K527, K532, R585 and/or R588, numbering based on VP1 of AAV2. In some embodiments, the rAAV particle comprises the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NOs:2, 4 and/or 6. In some embodiments, the one or more amino acid substitutions comprises a R347A, R350A, K390A, K395A, R448A, R451A, R484A, R487A, K527A, K532A, R585A and/or R588A substitution, numbering based on VP1 of AAV2. In some embodiments, the one or more amino acid substitutions comprises substitutions at position R484 and R487 or at positions R585 and R588, numbering based on VP1 of AAV2. In some embodiments, the one or more amino acid substitutions comprises R484A and R487A substitutions or R585A and R588A substitutions, numbering based on VP1 of AAV2. In some embodiments, the AAV capsid comprises amino acid substitutions R585A and R588A, numbering based on VP1 of AAV2. In some embodiments, the AAV capsid comprises amino acid substitutions K532A, numbering based on VP1 of AAV2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid.

In some embodiments of the above aspects and embodiments, the one or more amino acid substitutions is at position 485, 488, 528, 533, 586 or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an arginine or lysine residue with an alanine residue. In some embodiments, the amino acid substitution is at position 485, 488, 528, 533, or 589, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position R485, R488, R533, or T589, numbering based on VP1 numbering of AAVrh8R. In some embodiments, the rAAV particle comprises rAAV capsid protein of SEQ ID NO:11. In some embodiments, the rAAV particle comprises one or more rAAV capsid proteins having at least about 90%, at least about 91%, at least about 92%, at least about 93%, at least about 94%, at least about 95%, at least about 96%, at least about 97%, at least about 98%, at least about 99%, or 100% sequence identity to SEQ ID NO:11. In some embodiments, the one amino acid substitution comprises a R533A substitution, numbering based on VP1 of AAVrh8R.

In some embodiments of the above aspects and embodiments, the heterologous nucleic acid is under the control of a promoter sequence that is expressed in one or more cells of the CNS. In some embodiments, the heterologous nucleic acid is under the control of a promoter sequence selected from the group consisting of a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a β-actin promoter. In some embodiments, the heterologous nucleic acid is operably linked to a promoter suitable for expression of the therapeutic polypeptide or therapeutic nucleic acid in one or more cells of the CNS. In some embodiments, the one or more cells of the CNS comprise one or more cells of the brain. In some embodiments, the one or more cells of the CNS is an oligodendrocyte, astrocyte, neuron, brain parenchyma cell, microglial cell, ependemal cell, and/or a Purkinje cell.

In some embodiments of the above aspects and embodiments, the rAAV vector is a self-complementary rAAV vector. In some embodiments, the vector comprises first nucleic acid sequence encoding the heterologous nucleic acid and a second nucleic acid sequence encoding a complement of the nucleic acid, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects and embodiments, the individual is a human.

In some embodiments of the above aspects and embodiments, the rAAV particles are in a composition. In some embodiments, the composition comprises a buffer and/or a pharmaceutically acceptable excipient. In some embodiments, the kit or rAAV particle further comprises instructions for delivery of the composition of rAAV particles to the CNS. In some embodiments, the kit or rAAV particle further comprises instructions for delivery of the composition of rAAV particles to the striatum.

In some aspects, the invention provides a rAAV particle comprising a AAVrh8R capsid protein, wherein the AAVrh8R capsid protein comprises one or more amino acid substitution, wherein the one or more amino acid substitutions increases binding of the rAAV particle to the heparan sulfate proteoglycan compared to an AAV particle comprising a wild type AAVrh8R capsid protein, or wherein the one or more amino acid substitution is at one or more positions corresponding to amino acids 484, 487, 527, 532, 585 or 588, numbering based on VP1 numbering of AAV2. In some embodiments, the one or more amino acid substitutions increases binding of the rAAV particle to the heparan sulfate proteoglycan by about at least 10%, about at least 25%, about at least 50%, about at least 75%, or about at least 100%. In some embodiments, the amino acid substitution is at position 586, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position A586, numbering based on VP1 numbering of AAVrh8R. In some embodiments, the amino acid substitution comprises a A586R or A586K substitution, numbering based on VP1 numbering of AAVrh8R. In some embodiments, the rAAV particle comprises rAAV capsid protein of SEQ ID NO:10.

In some aspects, the invention provides a method of increasing the binding of a rAAV particle comprising a AAVrh8R capsid protein to heparan sulfate proteoglycan, comprising introducing one or more amino acid substitution to the capsid protein, wherein the one or more amino acid substitutions increases binding of the rAAV particle to the heparan sulfate proteoglycan compared to an AAV particle comprising a wild type AAVrh8R capsid protein. In some embodiments, the one or more amino acid substitutions increases binding of the rAAV particle to the heparan sulfate proteoglycan by about at least 10%, about at least 25%, about at least 50%, about at least 75%, or about at least 100%. In some embodiments, the amino acid substitution is at position 586, numbering based on VP1 numbering of AAVrh8R. In some embodiments, the numbering is based on the VP1 of AAVrh8R comprising the amino acid sequence of SEQ ID NO:9. In some embodiments, the amino acid substitution comprises a substitution at position A586, numbering based on VP1 numbering of AAVrh8R. In some embodiments, the amino acid substitution comprises a A586R or A586K substitution, numbering based on VP1 numbering of AAVrh8R. In some embodiments, the rAAV particle comprises rAAV capsid protein of SEQ ID NO:10.

In some aspects, the invention provides a method for delivering a heterologous nucleic acid to the retina of an individual comprising intravitreally administering a recombinant adeno-associated virus (rAAV) particle to the individual, wherein the rAAV particle comprises a) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising the heterologous nucleic acid and at least one AAV inverted terminal repeat. In some aspects, the invention provides a method for improving rAAV transduction of cells following intravitreal delivery of a rAAV particle to the eye of an individual compared to transduction of cells with a rAAV comprising a wild-type capsid, the method comprising incorporating one or more amino acid substitutions in an AAV capsid protein at one or more positions that interacts with a heparan sulfate proteoglycan or at one or more positions corresponding to amino acids 484, 487, 527, 532, 585 or 588, numbering based on VP1 numbering of AAV2; wherein the rAAV particle comprises the rAAV capsid protein and a rAAV vector comprising a heterologous nucleic acid and at least one AAV terminal repeat. In some aspects, the invention provides a method for improving expression of a heterologous nucleic acid following intravitreal delivery of rAAV particles to the eye of an individual, the method comprising incorporating one or more amino acid substitutions in an AAV capsid protein at one or more positions that interacts with a heparan sulfate proteoglycan or at one or more positions corresponding to amino acids 484, 487, 527, 532, 585 or 588, numbering based on VP1 numbering of AAV2; wherein the rAAV particle comprises the rAAV capsid protein and a rAAV vector comprising a heterologous nucleic acid and at least one AAV terminal repeat. In some aspects, the invention provides a method to treat an ocular disorder in an individual comprising intravitreal delivery of a composition comprising rAAV particles to the retina of an individual, wherein the rAAV particles comprise a) a rAAV capsid comprising a rAAV capsid protein comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and b) a rAAV vector comprising a heterologous nucleic acid and at least one AAV terminal repeat. In some aspects, the invention provides a system for intravitreal delivery of a vector to an eye of an individual, comprising a) a composition comprising an effective amount of rAAV particles, wherein i) a capsid protein of the rAAV particles comprises one or more amino acid substitutions at one or more positions that interacts with a heparan sulfate proteoglycan or at one or more positions corresponding to amino acids 484, 487, 527, 532, 585 or 588, and ii) the vector comprises a heterologous nucleic acid encoding a therapeutic polypeptide or therapeutic RNA and at least one AAV terminal repeat; and b) a device for intravitreal delivery of the rAAV. In some embodiments, the rAAV particle comprises an AAVrh8R, AAV1, AAV6, AAV8, AAV9, or AAVrh10 serotype capsid. In some aspects, the invention provides a kit for treating an ocular disorder comprising a) a composition comprising rAAV particles, wherein the rAAV particle comprises i) a rAAV capsid comprising rAAV capsid proteins comprising one or more amino acid substitutions at one or more positions that interacts with a heparan sulfate proteoglycan or at one or more positions corresponding to amino acids 484, 487, 527, 532, 585 or 588, numbering based on VP1 numbering of AAV2, and ii) a rAAV vector comprising the heterologous nucleic acid for treating an ocular disorder and at least one AAV inverted terminal repeat; and b) a pharmaceutical excipient suitable for intravitreal administration. In some embodiments, the rAAV particle comprises an AAVrh8R, AAV1, AAV6, AAV8, AAV9, or AAVrh10 capsid. In some aspects, the invention provides rAAV particle comprising a AAV1 capsid protein, wherein the AAV1 capsid protein comprises one or more amino acid substitutions, wherein the one or more amino acid substitutions increase transduction efficiency of the rAAV particle to a cell in the eye compared to an AAV particle comprising a wild type AAV1 capsid protein, or wherein the one or more amino acid substitution is at one or more positions corresponding to amino acids 484, 487, 527, 532, 585 or 588, numbering based on VP1 numbering of AAV2. In some aspects, the invention provides a rAAV particle comprising a AAV6 capsid protein, wherein the AAV6 capsid protein comprises one or more amino acid substitutions, wherein the one or more amino acid substitutions increase transduction efficiency of the rAAV particle to a cell in the eye compared to an AAV particle comprising a wild type AAV6 capsid protein, or wherein the one or more amino acid substitution is at one or more positions corresponding to amino acids 484, 487, 527, 532, 585 or 588, numbering based on VP1 numbering of AAV2. In some aspects, the invention provides a rAAV particle comprising a AAV8 capsid protein, wherein the AAV8 capsid protein comprises one or more amino acid substitutions, wherein the one or more amino acid substitutions increase transduction efficiency of the rAAV particle to a cell in the eye compared to an AAV particle comprising a wild type AAV8 capsid protein, or wherein the one or more amino acid substitution is at one or more positions corresponding to amino acids 484, 487, 527, 532, 585 or 588, numbering based on VP1 numbering of AAV2. In some aspects, the invention provides a rAAV particle comprising a AAV9 capsid protein, wherein the AAV9 capsid protein comprises one or more amino acid substitutions, wherein the one or more amino acid substitutions increase transduction efficiency of the rAAV particle to a cell in the eye compared to an AAV particle comprising a wild type AAV9 capsid protein, or wherein the one or more amino acid substitution is at one or more positions corresponding to amino acids 484, 487, 527, 532, 585 or 588, numbering based on VP1 numbering of AAV2. In some aspects, the invention provides a rAAV particle comprising a AAVrh10 capsid protein, wherein the AAVrh10 capsid protein comprises one or more amino acid substitutions, wherein the one or more amino acid substitutions increase transduction efficiency of the rAAV particle to a cell in the eye compared to an AAV particle comprising a wild type AAVrh10 capsid protein, or wherein the one or more amino acid substitution is at one or more positions corresponding to amino acids 484, 487, 527, 532, 585 or 588, numbering based on VP1 numbering of AAV2. In some aspects, the invention provides a rAAV particle comprising an AAV3 capsid protein, wherein the AAV3 capsid protein comprises one or more amino acid substitutions at one or more positions corresponding to amino acids 484, 487, 527, 532, 585 or 588, numbering based on VP1 numbering of AAV2. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid. In some embodiments, the transduction efficiency is increased by at least about 10%, at least about 25%, at least about 50%, at least about 75%, or at least about 100%.

In some embodiments, the one or more amino acid substitutions increases binding of the rAAV particle to the heparan sulfate proteoglycan. In some embodiments, the one or more amino acid substitutions increases binding of the rAAV particle to the heparan sulfate proteoglycan by about at least 10%, about at least 25%, about at least 50%, about at least 75%, or about at least 100%. In some embodiments, the one or more amino acid substitutions increases transduction efficiency of the rAAV particle for a cell in the eye or the central nervous system, as compared to an AAV particle comprising a wild-type AAVrh8R capsid protein, by about at least 10%, about at least 25%, about at least 50%, about at least 75%, or about at least 100%. In some embodiments, the cell of the eye is a retina cell, a photoreceptor cell, a retinal pigmented epithelial cells, bipolar cells, horizontal cells, amacrine cells, muller cells and/or ganglion cells. In some embodiments, the one or more amino acid substitutions comprise a substitution of an amino acid residue that is not positively charged with a positively charged amino acid residue. In some embodiments, the positively charged amino acid residue replaces a hydrophobic amino acid residue. In some embodiments, the one or more amino acid substitutions comprises substitution with an arginine or lysine residue. In some embodiments, the one or more amino acid substitutions comprises substitution of an alanine, serine, glutamine, or threonine residue with an arginine or lysine residue. In some embodiments, the rAAV particle comprises an AAV serotype rh8R (AAVrh8R) capsid. In some embodiments, the one or more amino acid substitutions are at positions 586 and/or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution at position A586 and/or T589, numbering based on VP1 numbering of AAVrh8R. In some embodiments, the one or more amino acid substitutions comprise an A586R or A586K substitution, numbering based on VP1 of AAVrh8R. In some embodiments, the one or more amino acid substitutions comprise a T589R or T589K substitution, numbering based on VP1 of AAVrh8R. In some embodiments, the rAAV particle comprises an AAV serotype 1 (AAV1) capsid. In some embodiments, the one or more amino acid substitutions are at positions 586 and/or 589, numbering based on VP1 numbering of AAV1. In some embodiments, the VP1 of AAV1 comprises the amino acid sequence of SEQ ID NO:12. In some embodiments, the one or more amino acid substitutions comprise a substitution at position S586 and/or T589, numbering based on VP1 numbering of AAV1. In some embodiments, the one or more amino acid substitutions comprise an S586R or S586K substitution, numbering based on VP1 of AAV1. In some embodiments, the one or more amino acid substitutions comprise a T589R or T589K substitution, numbering based on VP1 of AAV1. In some embodiments, the rAAV particle comprises an AAV serotype 6 (AAV6) capsid. In some embodiments, the one or more amino acid substitutions are at positions 586 and/or 589, numbering based on VP1 numbering of AAV6. In some embodiments, the numbering is based on the VP1 of AAV6 comprising the amino acid sequence of SEQ ID NO:13. In some embodiments, the one or more amino acid substitutions comprise a substitution at position S586 and/or T589, numbering based on VP1 numbering of AAV6. In some embodiments, the one or more amino acid substitutions comprise an S586R substitution, numbering based on VP1 of AAV6. In some embodiments, the one or more amino acid substitutions comprise a T589R or T589K substitution, numbering based on VP1 of AAV6. In some embodiments, the rAAV particle comprises an AAV serotype 8 (AAV8) capsid. In some embodiments, the one or more amino acid substitutions are at positions 588 and/or 591, numbering based on VP1 numbering of AAV8. In some embodiments, the VP1 of AAV8 comprises the amino acid sequence of SEQ ID NO:14. In some embodiments, the one or more amino acid substitutions comprise a substitution at position Q588 and/or T591, numbering based on VP1 numbering of AAV8. In some embodiments, the one or more amino acid substitutions comprise a Q588R or Q588K substitution, numbering based on VP1 of AAV8. In some embodiments, the one or more amino acid substitutions comprise a T591R substitution, numbering based on VP1 of AAV8. In some embodiments, the rAAV particle comprises an AAV serotype 9 (AAV9) capsid. In some embodiments, the one or more amino acid substitutions are at positions 586 and/or 589, numbering based on VP1 numbering of AAV9. In some embodiments, the VP1 of AAV9 comprises the amino acid sequence of SEQ ID NO:15. In some embodiments, the one or more amino acid substitutions comprise a substitution at position S586 and/or A589, numbering based on VP1 numbering of AAV9. In some embodiments, the one or more amino acid substitutions comprise an S586R or S586K substitution, numbering based on VP1 of AAV9. In some embodiments, the one or more amino acid substitutions comprise an A589R or A589K substitution, numbering based on VP1 of AAV9. In some embodiments, the rAAV particle comprises an AAV serotype rh10 (AAVrh10) capsid. In some embodiments, the one or more amino acid substitutions are at positions 588 and/or 591, numbering based on VP1 numbering of AAVrh10. In some embodiments, the VP1 of AAVrh10 comprises the amino acid sequence of SEQ ID NO:16. In some embodiments, the one or more amino acid substitutions comprise a substitution at position Q588 and/or A591, numbering based on VP1 numbering of AAVrh10. In some embodiments, the one or more amino acid substitutions comprise a Q588R or Q588K substitution, numbering based on VP1 of AAVrh10. In some embodiments, the one or more amino acid substitutions comprise an A591R or A591K substitution, numbering based on VP1 of AAVrh10. In some embodiments, the invention provides a rAAV particle comprising an AAV3 capsid protein, wherein the AAV3 capsid protein comprises one or more amino acid substitutions at one or more positions corresponding to amino acids 484, 487, 527, 532, 585 or 588, numbering based on VP1 numbering of AAV2. In some embodiments, the one or more amino acid substitutions increases transduction efficiency of the rAAV particle for a cell in the eye or the central nervous system, as compared to an AAV particle comprising a wild-type AAVrh8R capsid protein, by about at least 10%, about at least 25%, about at least 50%, about at least 75%, or about at least 100%. In some embodiments, the rAAV particle comprises an AAV1 capsid, an AAV2 capsid, an AAV3 capsid, an AAV6 capsid, an AAV8 capsid, an AAVrh8R capsid, an AAV9 capsid, or an AAVrh10 capsid. In some embodiments, the heterologous nucleic acid encodes a therapeutic polypeptide or therapeutic nucleic acid. In some embodiments, the heterologous nucleic acid encodes a polypeptide selected from the group consisting of an anti-oxidant, a neurotrophic factor, an anti-apoptotic factor, an anti-angiogenic factor, and an anti-inflammatory factor. In further embodiments, the heterologous nucleic acid encodes a polypeptide selected from the group consisting of: Prph2, RPE65, AIPL1, GUCY2D, LCA5, CRX, CEP290, MYO 7a, Clarin, ABCA4, RDH12, IMPDH1, CRB1, LRAT, NMNAT1, TULP1, MERTK, RPGR, RP2, RPGRIP, CNGA3, CNGB3, GNAT2, GDNF, CNTF, FGF2, PEDF, EPO, BCL2, BCL-X, NFκB, Endostatin, Angiostatin, sFlt, sPDGF-R, IL10, anti-IL17, sIL17R, IL1-ra, anti-TGFβ, sTNF-R I, sTNF-R II, and IL4. In other embodiments, the heterologous nucleic acid encodes a therapeutic nucleic acid. In further embodiments, the therapeutic nucleic acid is an siRNA, an shRNA an RNAi, an miRNA, an antisense RNA, a ribozyme or a DNAzyme. In some embodiments, the rAAV vector is a self-complementary rAAV vector. In some embodiments, the AAV particles of the invention comprise a capsid comprising one or more amino acid substitutions which alter binding to HSPG (e.g., reduces or ablates binding to HSPG) or at one or more positions corresponding to amino acids 484, 487, 527, 532, 585 or 588, numbering based on VP1 numbering of AAV2 and a heterologous nucleic acid encoding a therapeutic polypeptide or therapeutic nucleic acid, wherein the heterologous nucleic acid is under the control of a promoter sequence that is expressed in the retina. In some embodiments, the heterologous nucleic acid is operably linked to a promoter suitable for expression of the therapeutic polypeptide or therapeutic nucleic acid in one or more retina cell types. In some embodiments, the retina cell is a photoreceptor cell, a retinal pigmented epithelial cells, bipolar cells, horizontal cells, amacrine cells, muller cells and/or ganglion cells. In some embodiments, the promoter is a rhodopsin kinase (RK) promoter, an opsin promoter, a Cytomegalovirus (CMV) promoter, a chicken β-actin (CBA) promoter. In some embodiments, the individual is a human. In some embodiments, the heterologous nucleic acid is used to treat an ocular disorder selected from the group consisting of: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis. In some embodiments, the rAAV vector is a self-complementary rAAV vector. In some embodiments, the vector comprises first nucleic acid sequence encoding the heterologous nucleic acid and a second nucleic acid sequence encoding a complement of the nucleic acid, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the individual is a human. In some embodiments, the one or more amino acid substitutions increases transduction efficiency of the rAAV particle for a cell in the eye or the central nervous system, as compared to an AAV particle comprising a wild-type AAVrh8R capsid protein, by about at least 10%, about at least 25%, about at least 50%, about at least 75%, or about at least 100%.

All references cited herein, including patent applications and publications, are incorporated by reference in their entirety.

BRIEF DESCRIPTION OF THE DRAWINGS

FIG. 1 indicates the capsid residues implicated in heparan sulfate proteoglycan binding and the mutations introduced to generate the AAV2 HBKO mutant. Numbering is based on the VP1 amino acid sequence.

FIG. 5 shows that HBKO mutant AAV2 particles fail to transduce the mouse eye after intravitreal injection. Mice were given an intravitreal injection of wild-type (AAV2 CBA-GFP) or HBKO mutant (AAV2 HBKO CBA-GFP) AAV2 particles bearing vectors that use the CBA promoter to drive expression of EGFP, and sections were imaged by fluorescence microscopy.

FIGS. 10A&10B show expression of GFP in the mouse brain 30 days following intrastriatal injection of AAV2HBKO-miRNA-Htt-GFP (FIG. 10A), compared to AAV1-miRNA-Htt-GFP (FIG. 10B) in YAC128 HD mice. The miRNA-Htt-GFP vectors refer to constructs that express an artificial miRNA targeting human Htt and a GFP reporter. In each panel, expression of GFP was driven by the CBA promoter and visualized using fluorescence microscopy at three different magnifications (4×, 10×, and 20×, as labeled).

FIGS. 12A-12C show expression of Iba1 in YAC128 mouse striatum 30 days post injection with AAV2HBKO-miRNA-Htt-GFP (FIG. 12B) or AAV1-miRNA-Htt-GFP (FIG. 12C), compared to untreated controls (FIG. 12A).

FIGS. 13A-13C show expression of GFP in YAC128 mouse striatum 30 days post injection with AAV2HBKO-miRNA-Htt-GFP (FIG. 13B) or AAV1-miRNA-Htt-GFP (FIG. 13C), compared to untreated controls (FIG. 13A).

FIG. 14 compares the capsid residues implicated in heparan sulfate proteoglycan binding between AAV2 and AAVrh8R capsids. Numbering is based on the VP1 amino acid sequence.

FIG. 15 shows an amino acid alignment of AAV2 and AAVrh8R at the residues responsible for heparan binding of AAV2. The positions of the AAVrh8R arginine capsid modifications are circled.

(FIG. 18A) AAVrh8R A586R mutant shows decreased subretinal transduction, as compared to wild-type AAVrh8R. AAV2 vector was also tested. (FIG. 18B) AAVrh8R R533A mutant shows increased subretinal transduction, as compared to wild-type AAVrh8R and naïve mice. Transduction was monitored by sFLT02 in retinal lysates of C57B16 mice 30 days post-subretinal administration of AAVrh8R or AAVrh8R arginine modified vectors.

FIG. 20 shows an amino acid alignment at the residues responsible for heparan binding of AAV2 with AAVrh8R, AAV1, AAV6, AAV8, AAV9, and AAVrh10.

DETAILED DESCRIPTION

Figure 2:
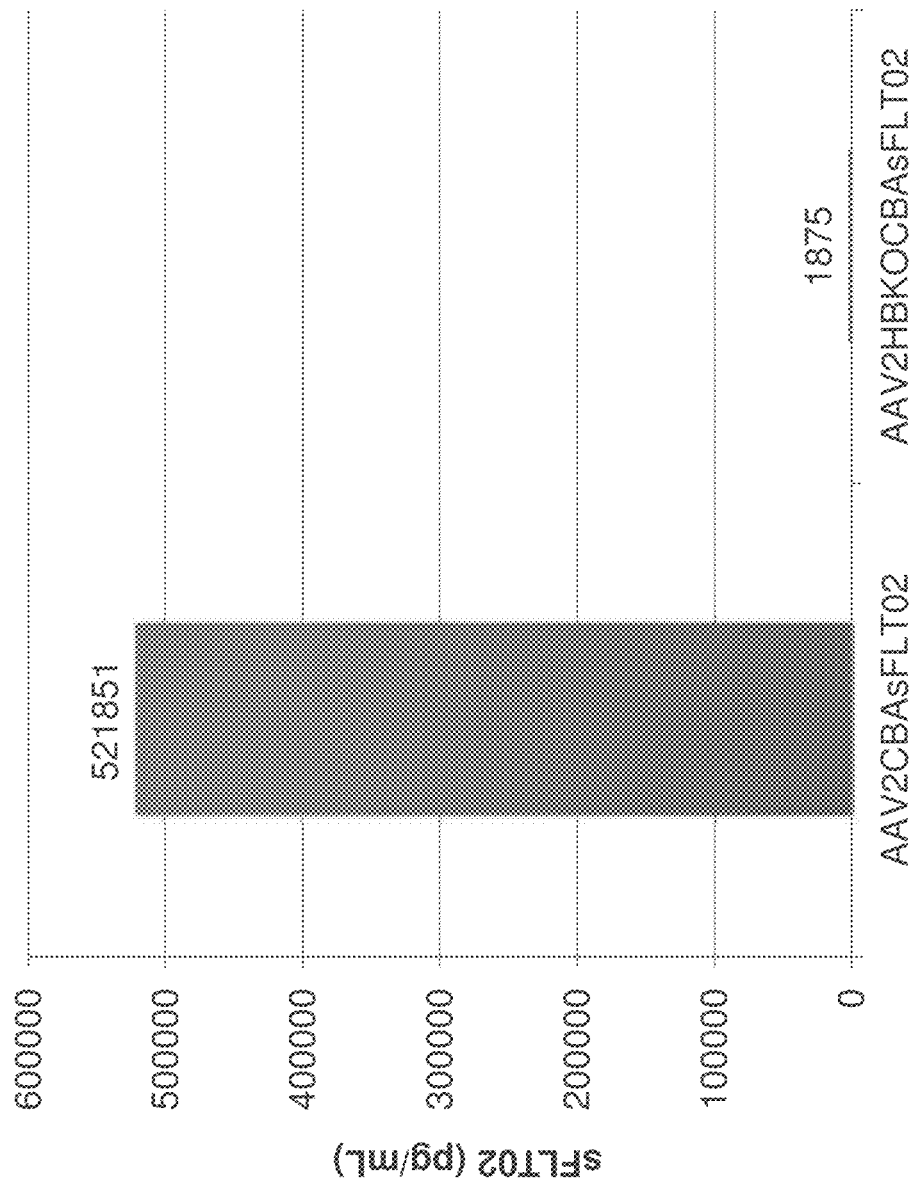
FIG. 2 shows the decrease in transduction of 293 cells in culture observed with HBKO mutant AAV2 particles (AAV2 HBKO CBA-sFLT02), as compared to wild-type AAV2 particles (AAV2 CBA-sFLT02). Transduction was assayed by measuring the amount of soluble Flt (sFLT) present in the cell culture media 48 hours after injection with wild-type or HBKO mutant AAV2 particles bearing vectors that use the CBA promoter to drive expression of Flt.

As described herein, the inventors have surprisingly discovered that modifications in rAAV particles corresponding to amino acids 484, 487, 532, 585, and/or 588, numbering based on VP1 numbering of AAV2, demonstrate increased transduction of cells following administration to the eye or CNS of a subject. Not wishing to be bound by any theory, it is believed that these rAAV particles have reduced or ablated binding to HSPG or have modified charge on the capsid such that administration of the rAAV particles results in increased transduction of cells in the eye or CNS of a subject. The present invention therefore provides methods for delivering a heterologous nucleic acid to the eye or CNS of an individual comprising administering a recombinant adeno-associated virus (rAAV) particle to the eye or CNS of the individual, wherein the rAAV particle comprises a) a rAAV capsid comprising rAAV capsid proteins comprising one or more amino acid substitutions at one or more positions that interacts with a heparan sulfate proteoglycan, and b) a rAAV vector comprising the heterologous nucleic acid and at least one AAV inverted terminal repeat. In some embodiments, the amino acid substitutions result in reduced or ablated binding to HSPG.

In some aspects, the present invention provides methods for delivering a heterologous nucleic acid to the eye of an individual comprising administering a recombinant adeno-associated virus (rAAV) particle to the subretina of the individual, wherein the rAAV particle comprises a) a rAAV capsid comprising rAAV capsid proteins comprising one or more amino acid substitutions at one or more positions that interacts with a heparan sulfate proteoglycan, and b) a rAAV vector comprising the heterologous nucleic acid and at least one AAV inverted terminal repeat.

In some aspects, the invention provides methods for improving rAAV transduction of cells following subretinal delivery of a rAAV particle to the eye of an individual compared to transduction of cells with a rAAV comprising a wild-type capsid, the method comprising incorporating one or more amino acid substitutions in an AAV capsid protein at one or more positions that interacts with a heparan sulfate proteoglycan; wherein the rAAV particle comprises the rAAV capsid protein and a rAAV vector comprising the heterologous nucleic acid and at least one AAV terminal repeat. In some embodiments, the amino acid substitutions result in reduced or ablated binding to HSPG. In some embodiments, the rAAV particles comprise a capsid comprise R585A and R588A substitutions of rAAV2, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

In some aspects, the invention provides methods for improving expression of a heterologous nucleic acid following subretinal delivery of rAAV particles to the eye of an individual, the method comprising incorporating one or more amino acid substitutions in an AAV capsid protein at one or more positions that interacts with a heparan sulfate proteoglycan; wherein the rAAV particle comprises the rAAV capsid protein and a rAAV vector comprising the heterologous nucleic acid and at least one AAV terminal repeat. In some embodiments, the amino acid substitutions result in reduced or ablated binding to HSPG. In some embodiments, the rAAV particles comprise a capsid comprise R585A and R588A substitutions of rAAV2, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

In some aspects, the invention provides methods for improving expression of a heterologous nucleic acid following subretinal delivery of rAAV particles to the eye of an individual, the method comprising incorporating one or more amino acid substitutions in an AAV capsid protein at one or more positions that interacts with a heparan sulfate proteoglycan; wherein the rAAV particle comprises the rAAV capsid protein and a rAAV vector comprising the heterologous nucleic acid and at least one AAV terminal repeat. The improvement is transduction is compared to rAAV particles comprising wild-type capsid. In some embodiments, the amino acid substitutions result in reduced or ablated binding to HSPG. In some embodiments, the rAAV particles comprise a capsid comprise R585A and R588A substitutions of rAAV2 capsid, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

In some aspects, the invention provides methods to treat an ocular disorder in an individual comprising delivery of a composition comprising an effective amount of rAAV particles to the retina of an individual, wherein the rAAV particles comprise a) a rAAV capsid comprising a rAAV capsid protein comprising one or more amino acid substitutions at one or more positions that interacts with a heparan sulfate proteoglycan, and b) a rAAV vector comprising the heterologous nucleic acid and at least one AAV terminal repeat. In some embodiments, the amino acid substitutions result in reduced or ablated binding to HSPG. In some embodiments, the rAAV particles comprise a capsid comprise R585A and R588A substitutions of rAAV2, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

The invention also provides systems for subretinal delivery of a vector to an eye of an individual, comprising a) a composition comprising an effective amount of rAAV particles, wherein i) a capsid protein of the rAAV particles comprises one or more amino acid substitutions at one or more positions that interacts with a heparan sulfate proteoglycan, and ii) the vector comprises a heterologous nucleic acid encoding a therapeutic polypeptide or therapeutic RNA and at least one AAV terminal repeat; and b) a device for retinal delivery of the rAAV. In some embodiments, the amino acid substitutions result in reduced or ablated binding to HSPG. In some embodiments, the rAAV particles comprise a capsid comprise R585A and R588A substitutions of rAAV2, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

In some aspects, the present invention further provides methods for delivering a heterologous nucleic acid to the central nervous system (CNS) of an individual comprising administering a recombinant adeno-associated virus (rAAV) particle to the CNS of the individual. The rAAV particle comprises (a) a rAAV capsid comprising rAAV capsid proteins comprising one or more amino acid substitutions at one or more positions that interacts with a heparan sulfate proteoglycan, and (b) a rAAV vector comprising the heterologous nucleic acid and at least one AAV inverted terminal repeat. These methods exhibit improved heterologous nucleic acid expression and/or rAAV transduction of cells following delivery of a rAAV particle to the CNS of an individual, e.g., as compared to transduction of cells with a rAAV comprising a wild-type capsid. Moreover, the methods of the present invention are capable of infecting specific cells (e.g., neurons) while still achieving a widespread and robust transduction efficiency. Such rAAV particles and methods are suitable for use in treating CNS disorders, including but not limited to Huntington's Disease. In some embodiments, the amino acid substitutions result in reduced or ablated binding to HSPG. In some embodiments, the rAAV particles comprise a capsid comprise R585A and R588A substitutions of rAAV2, numbering based on VP1 of AAV2 (SEQ ID NO:1). In some embodiments, the rAAV particles comprise a capsid comprising A586R and/or R533A substitutions of AAVrh8R, numbering based on VP1 of AAVrh8R (SEQ ID NO:9).

The present invention also provides kits containing rAAV particles or compositions containing rAAV particles having (a) a rAAV capsid comprising rAAV capsid proteins comprising one or more amino acid substitutions at one or more positions that interacts with a heparan sulfate proteoglycan, and (b) a rAAV vector comprising the heterologous nucleic acid and at least one AAV inverted terminal repeat. These kits are useful for delivering heterologous nucleic acids to the eye or CNS of an individual, as well as for treating ocular or CNS disorders in an individual (e.g., treating a retinopathy or Huntington's disease).

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two ITRs.

A "recombinant AAV vector (rAAV vector)" refers to a polynucleotide vector comprising one or more heterologous sequences (i.e., nucleic acid sequence not of AAV origin) that are flanked by at least one AAV inverted terminal repeat sequence (ITR). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)".

An "rAAV virus" or "rAAV viral particle" refers to a viral particle composed of at least one AAV capsid protein and an encapsidated rAAV vector genome.

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. An example of an alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, a "therapeutic" agent (e.g., a therapeutic polypeptide, nucleic acid, or transgene) is one that provides a beneficial or desired clinical result, such as the exemplary clinical results described above. As such, a therapeutic agent may be used in a treatment as described above.

The term "central retina" as used herein refers to the outer macula and/or inner macula and/or the fovea. The term "central retina cell types" as used herein refers to cell types of the central retina, such as, for example, RPE and photoreceptor cells.

The term "macula" refers to a region of the central retina in primates that contains a higher relative concentration of photoreceptor cells, specifically rods and cones, compared to the peripheral retina. The term "outer macula" as used herein may also be referred to as the "peripheral macula". The term "inner macula" as used herein may also be referred to as the "central macula".

The term "fovea" refers to a small region in the central retina of primates of approximately equal to or less than 0.5 mm in diameter that contains a higher relative concentration of photoreceptor cells, specifically cones, when compared to the peripheral retina and the macula.

The term "subretinal space" as used herein refers to the location in the retina between the photoreceptor cells and the retinal pigment epithelium cells. The subretinal space may be a potential space, such as prior to any subretinal injection of fluid. The subretinal space may also contain a fluid that is injected into the potential space. In this case, the fluid is "in contact with the subretinal space." Cells that are "in contact with the subretinal space" include the cells that border the subretinal space, such as RPE and photoreceptor cells.

The term "bleb" as used herein refers to a fluid space within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

"Rhodopsin kinase (RK) promoter" refers to a polynucleotide sequence derived from a rhodopsin kinase gene (e.g., human RK, represented by GenBank Entrez Gene ID 6011) that drives expression specifically in rod and cone photoreceptor cells, as well as retinal cell lines such as WERI Rb-1. As used herein, "rhodopsin kinase promoter" may refer to an entire promoter sequence or a fragment of the promoter sequence sufficient to drive photoreceptor-specific expression, such as the sequences described in Khani, S. C., et al. (2007) *Invest. Ophthalmol. Vis. Sci.* 48(9):3954-61 and Young, J. E., et al. (2003) *Invest. Ophthalmol. Vis. Sci.* 44(9):4076-85. In some embodiments, the RK promoter spans from −112 to +180 relative to the transcription start site.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J., et al. (1989) *Gene* 79(2):269-77. As used herein, the term "CAG promoter" may be used interchangeably. As used herein, the term "CMV early enhancer/chicken beta actin (CAG) promoter" may be used interchangeably.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Viral Particles

Heparan sulfate proteoglycan (HSPG) is known in the art to act as the cellular receptor for AAV2 particles (Summerford, C. and Samulski, R. J. (1998) *J. Virol.* 72(2):1438-45). Binding between an AAV2 particle and HSPG at the cell membrane serves to attach the particle to the cell. Other cell surface proteins such as fibroblast growth factor receptor and αvβ5 integrin may also facilitate cellular infection. After binding, an AAV2 particle may enter the cell through mechanisms including receptor mediated endocytosis via clathrin-coated pits. An AAV2 particle may be released from an endocytic vesicle upon endosomal acidification. This allows the AAV2 particle to travel to the perinuclear region and then the cell nucleus. AAV3 particles are also known to bind heparan (Rabinowitz, J. E., et al. (2002) *J. Virol.* 76(2):791-801).

Gene therapy protocols for disorders of the eye require the localized delivery of the vector to the cells in the eye (e.g., cells of the retina). The cells that will be the treatment target in these diseases may include, inter alia, one or more cells of the eye (e.g., photoreceptors, ocular neurons, etc.). The methods and kits of the invention are based, at least in part, on the discovery that specific rAAV capsids (e.g., those comprising a rAAV capsid protein comprising one or more amino acid substitutions at one or more positions that interacts with a heparan sulfate proteoglycan) allow for widespread vector distribution among cells of the eye. As such, these capsids may be particularly advantageous for delivering a heterologous nucleic acid to the eye of an individual, improving rAAV transduction of cells following delivery of a rAAV particle to the eye of an individual, improving expression of a heterologous nucleic acid following delivery of rAAV particles to the eye of an individual, and/or treating a disorder of the eye of an individual using rAAV particles.

Likewise, gene therapy protocols for disorders of the CNS require the localized delivery of the vector to the cells in the CNS. The cells that will be the treatment target in these diseases may include, inter alia, one or more cells of the brain (e.g., neurons). The methods and kits of the invention are based, at least in part, on the discovery that specific rAAV capsids (e.g., those comprising a rAAV capsid protein comprising one or more amino acid substitutions at one or more positions that interacts with a heparan sulfate proteoglycan) allow for widespread vector distribution among cells of the CNS. As such, these capsids may be particularly advantageous for delivering a heterologous nucleic acid to the central nervous system (CNS) of an individual, improving rAAV transduction of cells following delivery of a rAAV particle to the CNS of an individual, improving expression of a heterologous nucleic acid following delivery of rAAV particles to the CNS of an individual, and/or treating a disorder of the CNS of an individual using rAAV particles.

The capsid of AAV (e.g., AAV2, AAVrh8R, etc.) is known to include three capsid proteins: VP1, VP2, and VP3. These proteins contain significant amounts of overlapping amino acid sequence and unique N-terminal sequences. An AAV2 capsid includes 60 subunits arranged by icosahedral symmetry (Xie, Q., et al. (2002) *Proc. Natl. Acad. Sci.* 99(16): 10405-10). VP1, VP2, and VP3 have been found to be present in a 1:1:10 ratio.

The binding between AAV2 capsid proteins and HSPG is known to occur via electrostatic interactions between basic AAV2 capsid protein residues and negatively charged glycosaminoglycan residues (Opie, S R et al., (2003) *J. Virol.* 77:6995-7006; Kern, A et al., (2003) *J. Virol.* 77:11072-11081). Specific capsid residues implicated in these interactions include R484, R487, K532, R585, and R588. Mutations in these residues have been shown to reduce AAV2 binding to Hela cells and heparan itself (Opie, S R et al., (2003) *J. Virol.* 77:6995-7006; Kern, A et al., (2003) *J. Virol.* 77:11072-11081; WO 2004/027019 A2, U.S. Pat. No. 7,629, 322). Further, without wishing to be bound to theory, it is thought that amino acid substitution(s) at one or more of the residues corresponding to amino acids 484, 487, 532, 585 or 588, numbering based on VP1 numbering of AAV2 may modulate the transduction properties of AAV capsid types that do not bind to HSPG, or may modulate the transduction properties of AAV capsid types independent from their ability to bind HSPG.

Certain aspects of the invention relate to delivering a heterologous nucleic acid to an eye or the central nervous system (CNS) of an individual comprising administering a recombinant adeno-associated virus (rAAV) particle to an eye or the CNS of the individual. In some embodiments, the rAAV particle comprises a rAAV capsid comprising rAAV capsid proteins comprising one or more amino acid substitutions at one or more positions that interact with a heparan sulfate proteoglycan. In some embodiments, the rAAV particle of the invention comprises an AAV serotype 2 (AAV2) capsid. In some embodiments, the rAAV particle of the invention comprises an AAV serotype rh8R (AAVrh8R) capsid.

As described herein, rAAV particles with mutations in capsid proteins at residues that interact with HSPG or at one or more of the residues corresponding to amino acids 484, 487, 532, 585 or 588, numbering based on VP1 numbering of AAV2 show advantageous properties, such as enhanced expression and/or reduced neuroinflammation. Accordingly, in some embodiments, upon delivery the heterologous nucleic acid encoded by the rAAV vector is expressed at an increased level of expression, as compared to the level of expression of a heterologous nucleic acid of a rAAV particle comprising a rAAV capsid comprising a reference rAAV capsid protein (e.g., a wild-type rAAV capsid protein). In some embodiments, the expression of the nucleic acid is increased by at least about 10%, at least about 25%, at least about 50%, at least about 75%, or at least about 100%. In some embodiments, upon delivery the rAAV particle causes reduced neuroinflammation, as compared to a rAAV particle comprising a reference rAAV capsid protein (e.g., a wild-type rAAV capsid protein). In some embodiments, the neuroinflammation is reduced by at least about 10%, at least about 25%, at least about 50%, at least about 75%, or at least about 100%. A suitable reference rAAV capsid protein may include any capsid protein that lacks one or more amino acid substitutions at one or more positions that interact with a heparan sulfate proteoglycan (the reference capsid may thus contain one or more "background" substitutions that do not alter binding to HSPG).

In some embodiments, the invention provides methods for delivering a heterologous nucleic acid to the eye of an individual comprising administering a recombinant adeno-associated virus (rAAV) particle to the subretinal space of the individual wherein the rAAV particle comprises a) a rAAV capsid comprising rAAV capsid proteins comprising one or more amino acid substitutions at one or more positions that interacts with a heparan sulfate proteoglycan, and b) a rAAV vector comprising the heterologous nucleic acid and at least one AAV inverted terminal repeat.

In some embodiments, the rAAV particle of the invention comprises an AAV serotype 2 (AAV2) capsid. In some embodiments, one or more amino acid substitutions are substitutions of amino acid residues of any one of VP1, VP2 and/or VP3 of AAV2, wherein the amino substitutions alter interaction of the rAAV particle with HSPG (e.g., reduce or ablate binding to HSPG). In some embodiments, the one or more amino acid substitutions are substitutions of amino acid residues of VP1 AAV2. In some embodiments, the one or more amino acid substitutions are substitutions of amino acid residues of VP2 AAV2. In some embodiments, the one or more amino acid substitutions are substitutions of amino acid residues of VP3 AAV2. In some embodiments, one or more amino acid substitutions are substitutions of amino acid residues of combination of VP1, VP2 and VP3 of AAV2. In some embodiments, one or more amino acid substitutions are substitutions of amino acid residues of any one of VP1, VP2 and/or VP3 of AAV2. In some embodiments, one or more amino acid substitutions are substitutions of amino acid residues of any one of capsid proteins of SEQ ID NO:1, 3 and/or 5. In some embodiments, the rAAV particles of the invention comprise capsid proteins of SEQ ID NO:2, 4 and/or 6.

In some embodiments, the rAAV particle of the invention comprises an AAV serotype 3 (AAV3) capsid. In some embodiments, one or more amino acid substitutions are substitutions of amino acid residues of any one of VP1, VP2 and/or VP3 of AAV3, wherein the amino substitutions alter interaction of the rAAV particle with HSPG (e.g., reduce or ablate binding to HSPG). In some embodiments, the one or more amino acid substitutions are substitutions of amino acid residues of VP1 AAV3. In some embodiments, the one or more amino acid substitutions are substitutions of amino acid residues of VP2 AAV3. In some embodiments, the one or more amino acid substitutions are substitutions of amino acid residues of VP3 AAV3. In some embodiments, one or more amino acid substitutions are substitutions of amino acid residues of combination of VP1, VP2 and VP3 of AAV3. In some embodiments, one or more amino acid substitutions are substitutions of amino acid residues of any one of VP1, VP2 and/or VP3 of AAV3. In some embodiments, one or more amino acid substitutions are substitutions of amino acid residues corresponding to the capsid protein of SEQ ID NO:7.

In some embodiments, the rAAV particle of the invention comprises an AAV serotype rh8R (AAVrh8R) capsid, e.g., as described in U.S. PG Pub. No. 20090317417. In some embodiments, one or more amino acid substitutions are substitutions of amino acid residues of any one of VP1, VP2 and/or VP3 of AAVrh8R, wherein the amino substitutions alter interaction of the rAAV particle with HSPG (e.g., reduce or ablate binding to HSPG). In some embodiments, the one or more amino acid substitutions are substitutions of amino acid residues of VP1 AAVrh8R. In some embodiments, the one or more amino acid substitutions are substitutions of amino acid residues of VP2 AAVrh8R. In some embodiments, the one or more amino acid substitutions are substitutions of amino acid residues of VP3 AAVrh8R. In some embodiments, one or more amino acid substitutions are substitutions of amino acid residues of combination of VP1, VP2 and VP3 of AAVrh8R. In some embodiments, one or more amino acid substitutions are substitutions of amino acid residues of any one of VP1, VP2 and/or VP3 of AAVrh8R. In some embodiments, one or more amino acid substitutions are substitutions of amino acid residues of the capsid protein exemplified by SEQ ID NO:9. In some embodiments, the rAAV particles of the invention comprise capsid proteins of SEQ ID NOs:10 and/or 11.

In some embodiments, the one or more amino acid substitutions reduce binding of the rAAV particle to the heparan sulfate proteoglycan by about at least 10%, about at least 25%, about at least 50%, about at least 75%, or about at least 100%. In some embodiments, the one or more amino acid substitutions reduce binding of the rAAV particle to the heparan sulfate proteoglycan by about at least 10%, about at least 15%, about at least 20%, about at least 25%, about at least 30%, about at least 35%, about at least 40%, about at least 45%, about at least 50%, about at least 55%, about at least 60%, about at least 65%, about at least 70%, about at least 75%, about at least 80%, about at least 85%, about at least 90%, about at least 95%, or about at least 100% (as compared to binding of a rAAV particle comprising a wild-type capsid). In some embodiments, the one or more amino acid substitutions reduce binding of the rAAV particle to the heparan sulfate proteoglycan by any one of about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 90%, about 30% to about 90%, about 40% to about 90%, about 50% to about 90%, about 60% to about 90%, about 70% to about 90%, about 80% to about 90%, about 10% to about 80%, about 20% to about 80%, about 30% to about 80%, about 40% to about 80%, about 50% to about 80%, about 60% to about 80%, about 70% to about 80%, about 10% to about 70%, about 20% to about 70%, about 30% to about 70%, about 40% to about 70%, about 50% to about 70%, about 60% to about 70%, about 10% to about 60%, about 20% to about 60%, about 30% to about 60%, about 40% to about 60%, about 50% to about 60%, about 10% to about 50%, about 20% to about 50%, about 30% to about 50%, about 40% to about 50%, about 10% to about 40%, about 20% to about 40%, about 30% to about 40%, about 10% to about 30%, about 20% to about 30%, or about 10% to about 20%, (as compared to binding of a rAAV particle comprising a wild-type capsid). In some embodiments, the one or more amino acid substitutions results in no detectable binding of the rAAV particle to the heparan sulfate proteoglycan compared to binding of a wild-type rAAV particle. Means to measure binding of AAV particles to HSPG are known in the art; e.g., binding to a heparan sulfate chromatography media or binding to a cell known to express HSPG on its surface. For example, see Opie, S R et al., (2003) *J. Virol.* 77:6995-7006 and Kern, A et al., (2003) *J. Virol.* 77:11072-11081.

In some embodiments, the invention provides rAAV particles for subretinal delivery of a therapeutic nucleic acid, wherein the rAAV particles comprise one or more amino acid substitutions of capsid proteins that reduce or ablate binding of the rAAV particle to the heparan sulfate proteoglycan, wherein the one or more amino acid substitutions is at position 484, 487, 532, 585 or 588, numbering based on VP1 numbering of AAV2. In some embodiments, the one or more amino acid substitutions is at position 484, 487, 532, 585 or 588 of VP1 of AAV2. In some embodiments, the one or more amino acid substitutions is at position 484, 487, 532, 585 or 588 of VP2 of AAV2, numbering based on VP1 of AAV2. In some embodiments, the one or more amino acid substitutions is at position 484, 487, 532, 585 or 588 of VP3 of AAV2, numbering based on VP1 of AAV2. In some embodiments, the one or more amino acid substitutions is at position 484, 487, 532, 585 or 588 of VP1 of AAV2, VP2 of AAV2, and/or VP3 of AAV2, numbering based on VP1 of AAV2. In some embodiments, the VP1 of rAAV2 comprises the amino acid sequence of SEQ ID NO:1.

In some embodiments, the one or more amino acid substitutions is at position 484, 487, 532, 585 or 588 of VP1 of AAV3, numbering based on VP1 of AAV2. In some embodiments, the one or more amino acid substitutions is at position 484, 487, 532, 585 or 588 of VP2 of AAV3, numbering based on VP1 of AAV2. In some embodiments, the one or more amino acid substitutions is at position 484, 487, 532, 585 or 588 of VP3 of AAV3, numbering based on VP1 of AAV2. In some embodiments, the one or more amino acid substitutions is at position 484, 487, 532, 585 or 588 of VP1 of AAV3, VP2 of AAV3, and/or VP3 of AAV3, numbering based on VP1 of rAAV2. In some embodiments, the VP1 of rAAV2 comprises the amino acid sequence of SEQ ID NO:1.

In some embodiments, the AAV particles of the invention comprise capsid with one or more amino acid substitutions is at position 485, 488, 528, 533, 586 or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution of a positively charged amino acid residue with an amino acid residue that is not positively charged. In some embodiments, the positively charged amino acid residue is substituted with a hydrophobic amino acid residue. In further embodiments, the one or more amino acid substitutions comprises substitution of an arginine or lysine residue. In yet further embodiments, the one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an arginine or lysine residue with an alanine residue. In some embodiments, the one or more amino acid substitutions comprises a substitution at position R533 and/or A586, numbering based on VP1 of AAVrh8R. In further embodiments, the AAV capsid comprises amino acid substitutions A586R and/or R533A, numbering based on VP1 of AAVrh8R. In some embodiments, the rAAV particle comprises rAAV capsid proteins of SEQ ID NOs:10 and/or 11.

In some embodiments of the invention, the one or more amino acid substitutions comprise a substitution of a positively charged amino acid residue (e.g., an amino acid with a positively charged side chain) with an amino acid residue that is not positively charged (e.g., an amino acid that does not contain a positively charged side chain). Positively charged amino acids include arginine, histidine and lysine. Examples of amino acid residues that are not positively charged include negatively charged amino acids (aspartic acid and glutamic acid), amino acids with uncharged polar side chains (serine, threonine, asparagine, and glutamine), amino acids with hyrdrophobic side chains (alanine, valine, isoleucine, leucine, methionine, phenylalanine, tyrosine and tryptophan), glycine, cysteine, and proline. In some embodiments, the one or more positively charged amino acid residues of AAV capsid is substituted with a hydrophobic amino acid residue. In some embodiments, the one or more amino acid substitutions comprises substitution of an arginine or lysine residue. In further embodiments, one or more amino acid substitutions comprises substitution of an arginine or lysine residue with an alanine residue. In other embodiments, the one or more amino acid substitutions comprise a substitution of an amino acid residue that is not positively charged with a positively charged amino acid residue. In some embodiments, a hydrophobic amino acid residue is substituted with a positively charged amino acid residue. In further embodiments, the one or more amino acid substitutions comprises substitution of an alanine residue. In yet further embodiments, the one or more amino acid substitutions comprises substitution of an arginine or lysine residue with an alanine residue.

In some embodiments, the one or more amino acid substitutions comprises a substitution at position R484, R487, K527, K532, R585 and/or R588 of VP1, VP2 and/or VP3, numbering based on VP1 of AAV2. In some embodiments, the one or more amino acid substitutions comprises a substitution at position R484, R487, K527, K532, R585 and/or R588 of VP1, VP2 and/or VP3 of AAV2, numbering based on VP1 of AAV2. In some embodiments, the one or more amino acid substitutions comprises a substitution at position R484, R487, K527, K532, and/or R588 of VP1, VP2 and/or VP3 of AAV2, numbering based on SEQ ID NO:1. In some embodiments, the one or more amino acid substitutions comprises one or more of substitutions R484A, R487A, R585A and/or R588A of VP1, VP2 and/or VP3 of AAV2, numbering based on VP1 of AAV2. In some embodiments, the one or more amino acid substitutions comprises a substitution at position R484, R487, K527, K532, R585 and/or R588 of VP1, VP2 and/or VP3 of AAV3, numbering based on VP1 of AAV2. In some embodiments, the one or more amino acid substitutions comprises one or more of substitutions R484A, R487A, R585A and/or R588A of VP1, VP2 and/or VP3 of AAV3, numbering based on VP1 of AAV2. In some embodiments, the rAAV particle comprises rAAV capsid proteins of SEQ ID NOs:2, 4 and/or 6.

In some embodiments, the one or more amino acid substitutions comprises a substitution at position R485, R488, R533, A586 and/or T589 of VP1, VP2 and/or VP3, numbering based on VP1 of AAVrh8R. In some embodiments, the one or more amino acid substitutions comprises a substitution at position R485, R488, R533, A586 and/or T589 of VP1, VP2 and/or VP3, numbering based on VP1 of AAVrh8R, numbering based on SEQ ID NO:9. In some embodiments, the one or more amino acid substitutions comprises one or more of substitutions R533A and/or A586R of VP1, VP2 and/or VP3 of AAV2, numbering based on VP1 of AAVrh8R. In some embodiments, the rAAV particle comprises rAAV capsid proteins of SEQ ID NOs:10 and/or 11.

In some embodiments, the AAV capsid comprises one or more amino acid substitutions at one or more positions that interacts with HSPG. In some embodiments, the AAV capsid comprises one or more amino acid substitutions at one or more positions that reduces or ablates binding to HSPG. In some embodiments, the AAV capsid comprises one, two, three, four, five, six, seven, eight, nine, or ten amino acid substitutions that reduce or ablate binding to HSPG. In some embodiments, the AAV capsid has one, two, three, four, five, six, seven, eight, nine, or ten amino acid substitutions that reduce or ablate binding to HSPG. In some embodiments, the AAV capsid comprises substitutions at position R484 and R487, numbering based on VP1 of rAAV2. In some embodiments, the AAV capsid has substitutions at position R484 and R487, numbering based on VP1 of rAAV2. In some embodiments, the AAV capsid comprises substitutions at position R585 and R588, numbering based on VP1 of rAAV2. In some embodiments, the AAV capsid has substitutions at position R585 and R588, numbering based on VP1 of rAAV2. In some embodiments, the AAV capsid comprises substitutions R484A and R487A, numbering based on VP1 of rAAV2. In some embodiments, the AAV capsid has substitutions R484A and R487A, numbering based on VP1 of rAAV2. In some embodiments, the AAV capsid comprises substitutions R585A and R588A, numbering based on VP1 of rAAV2. In some embodiments, the AAV capsid has substitutions R585A and R588A, numbering based on VP1 of rAAV2.

Heparan sulfate proteoglycans (HSPGs) are known to be expressed in many tissues throughout the body and play important roles in the extracellular matrix, cell adhesion, and cell signaling. In some embodiments, the heparan sulfate proteoglycan is expressed on one or more cells of the CNS. In certain embodiments, the one or more cells of the CNS is a neuron.

In some embodiments, the invention provides rAAV particles for CNS delivery of a therapeutic nucleic acid, wherein the rAAV particles comprise one or more amino acid substitutions of capsid proteins that reduce or ablate binding of the rAAV particle to the heparan sulfate proteoglycan. In some embodiments, the one or more amino acid substitutions is at position 347, 350, 390, 395, 448, 451, 484, 487, 527, 532, 585 and/or 588, numbering based on VP1 of AAV2. As used herein, "numbering based on VP1 of AAV2" refers to the amino acid of the recited capsid protein corresponding to the recited amino acid of VP1 of AAV2. For example, if one or more amino acid substitutions are at position 347, 350, 390, 395, 448, 451, 484, 487, 527, 532, 585 and/or 588, numbering based on VP1 of AAV2, then the one or more amino acid substitutions are at the amino acid(s) of the recited capsid protein corresponding to amino acids 347, 350, 390, 395, 448, 451, 484, 487, 527, 532, 585 and/or 588 of VP1 of AAV2. In some embodiments, the one or more amino acid substitutions is at position R347, R350, K390, K395, R448, R451, R484, R487, K527, K532, R585 and/or R588, numbering based on VP1 of AAV2. In some embodiments, the one or more amino acid substitutions is at position 484, 487, 532, 585 or 588 of AAV2. In some embodiments, the one or more amino acid substitutions is at position 484, 487, 532, 585 or 588 of VP1 of AAV2, VP2 of AAV2, and/or VP3 of AAV2, numbering based on VP1 of AAV2. In some embodiments, the VP1 of AAV2 (e.g., rAAV2) comprises the amino acid sequence of SEQ ID NO:1.

In some embodiments, the AAV capsid comprises substitutions at positions R484, R487, K527, K532, R585 and/or R588, numbering based on VP1 of rAAV2. In some embodiments, the rAAV particles of the invention comprise capsid proteins of SEQ ID NOs:2, 4 and/or 6. In some embodiments, the AAV capsid comprises substitutions at positions R484 and R487 or R585 and R588, numbering based on VP1 of rAAV2. In some embodiments, the AAV capsid comprises R484A and R487A substitutions or R585A and R588A substitutions, numbering based on VP1 of AAV2. In some embodiments, the AAV capsid comprises amino acid substitutions R585A and R588A, numbering based on VP1 of AAV2. In some embodiments, the AAV capsid comprises amino acid substitution K532A, numbering based on VP1 of AAV2. In some embodiments, the one or more amino acid substitutions comprises R347A, R350A, K390A, K395A, R448A, R451A, R484A, R487A, K527A, K532A, R585A and/or R588A substitutions, numbering based on VP1 of AAV2.

In some embodiments, the invention provides rAAV particles for CNS delivery of a therapeutic nucleic acid, wherein the rAAV particles comprise one or more amino acid substitutions of capsid proteins that reduce or ablate binding of the rAAV particle to the heparan sulfate proteoglycan. In some embodiments, the rAAV particle of the invention comprises an AAV serotype rh8R (AAVrh8R) capsid, e.g., as described in U.S. PG Pub. No. 20090317417.

In some embodiments, one or more amino acid substitutions are substitutions of amino acid residues of any one of VP1, VP2 and/or VP3 of AAVrh8R, wherein the amino acid substitutions alter interaction of the rAAV particle with HSPG (e.g., reduce or ablate binding to HSPG). In some embodiments, the one or more amino acid substitutions are substitutions of amino acid residues of VP1 AAVrh8R. In some embodiments, the one or more amino acid substitutions are substitutions of amino acid residues of VP2 AAVrh8R. In some embodiments, the one or more amino acid substitutions are substitutions of amino acid residues of VP3 AAVrh8R. In some embodiments, one or more amino acid substitutions are substitutions of amino acid residues of combination of VP1, VP2 and VP3 of AAVrh8R. In some embodiments, one or more amino acid substitutions are substitutions of amino acid residues of any one of VP1, VP2 and/or VP3 of AAVrh8R. In some embodiments, one or more amino acid substitutions are substitutions of amino acid residues of the capsid protein exemplified by SEQ ID NO:9. In some embodiments, the rAAV particles of the invention comprise capsid proteins of SEQ ID NOs:10 and/or 11.

In some embodiments, the rAAV particle comprises an AAV serotype rh8R (AAVrh8R) capsid. In some embodiments, the one or more amino acid substitutions are at positions 586 and/or 589, numbering based on VP1 numbering of AAVrh8R. In some embodiments, the numbering is based on the VP1 of AAVrh8R comprising the amino acid sequence of SEQ ID NO:9. In some embodiments, the one or more amino acid substitutions comprise a substitution at position A586 and/or T589, numbering based on VP1 numbering of AAVrh8R. In some embodiments, the one or more amino acid substitutions comprise an A586R substitution, numbering based on VP1 of AAVrh8R. In some embodiments, the one or more amino acid substitutions comprise a T589R or T589K substitution, numbering based on VP1 of AAVrh8R.

As discussed above, without wishing to be bound to theory, it is thought that amino acid substitution(s) at one or more of the residues corresponding to amino acids 484, 487, 532, 585 or 588, numbering based on VP1 numbering of AAV2 may modulate the transduction properties of AAV capsid types that do not bind to HSPG, or may modulate the transduction properties of AAV capsid types independent from their ability to bind HSPG. In some embodiments, the one or more amino acid substitions comprise one or more amino acid corresponding to an amino acid shown in FIG. 20. For example, in some embodiments, one or more amino acids at position(s) corresponding to amino acids 585 and/or 588 (numbering based on VP1 of AAV2) are replaced by arginine residues (e.g., S586 and/or T589 for AAV1 or AAV6; S586 and/or A589 for AAV9; A586 and/or T589 for AAVrh8R; Q588 and/or T591 for AAV8; and Q588 and/or A591 for AAVrh10). These modified capsids may find use, inter alia, in improving intravitreal transduction targeting the retina. In other embodiments, one or more amino acids (e.g., arginine or lysine) at position(s) corresponding to amino acids 484, 487, 527 and/or 532 (numbering based on VP1 of AAV2) are replaced by non-positively charged amino acid(s) such as alanine (e.g., R485, R488, K528, and/or K533 for AAV1 or AAV6; R485, R488, K528, and/or R533 for AAV9 or AAVrh8R; and R487, R490, K530, and/or R535 for AAV8 or AAVrh10). These modified capsids may find use, inter alfa, in improving subretinal or CNS transduction.

In some embodiments, the rAAV particle comprises an AAV serotype 1 (AAV1) capsid. In some embodiments, the one or more amino acid substitutions are at positions 586 and/or 589, numbering based on VP1 numbering of AAV1.

In some embodiments, the VP1 of AAV1 comprises the amino acid sequence of SEQ ID NO:12. In some embodiments, the one or more amino acid substitutions comprise a substitution at position S586 and/or T589, numbering based on VP1 numbering of AAV1. In some embodiments, the one or more amino acid substitutions comprise an S586R or S586K substitution, numbering based on VP1 of AAV1. In some embodiments, the one or more amino acid substitutions comprise a T589R substitution, numbering based on VP1 of AAV1. In some embodiments, the rAAV particle comprises an AAV serotype 6 (AAV6) capsid. In some embodiments, the one or more amino acid substitutions are at positions 586 and/or 589, numbering based on VP1 numbering of AAV6. In some embodiments, the numbering is based on the VP1 of AAV6 comprising the amino acid sequence of SEQ ID NO:13. In some embodiments, the one or more amino acid substitutions comprise a substitution at position S586 and/or T589, numbering based on VP1 numbering of AAV6. In some embodiments, the one or more amino acid substitutions comprise an S586R or S586K substitution, numbering based on VP1 of AAV6. In some embodiments, the one or more amino acid substitutions comprise a T589R substitution, numbering based on VP1 of AAV6. In some embodiments, the rAAV particle comprises an AAV serotype 8 (AAV8) capsid. In some embodiments, the one or more amino acid substitutions are at positions 588 and/or 591, numbering based on VP1 numbering of AAV8. In some embodiments, the numbering is based on the VP1 of AAV8 comprising the amino acid sequence of SEQ ID NO:14. In some embodiments, the one or more amino acid substitutions comprise a substitution at position Q588 and/or T591, numbering based on VP1 numbering of AAV8. In some embodiments, the one or more amino acid substitutions comprise a Q588R or Q588K substitution, numbering based on VP1 of AAV8. In some embodiments, the one or more amino acid substitutions comprise a T591R substitution, numbering based on VP1 of AAV8. In some embodiments, the rAAV particle comprises an AAV serotype 9 (AAV9) capsid. In some embodiments, the one or more amino acid substitutions are at positions 586 and/or 589, numbering based on VP1 numbering of AAV9. In some embodiments, the numbering is based on the VP1 of AAV9 comprising the amino acid sequence of SEQ ID NO:15. In some embodiments, the one or more amino acid substitutions comprise a substitution at position S586 and/or A589, numbering based on VP1 numbering of AAV9. In some embodiments, the one or more amino acid substitutions comprise an S586R or S586K substitution, numbering based on VP1 of AAV9. In some embodiments, the one or more amino acid substitutions comprise an A589R or A589K substitution, numbering based on VP1 of AAV9. In some embodiments, the rAAV particle comprises an AAV serotype rh10 (AAVrh10) capsid. In some embodiments, the one or more amino acid substitutions are at positions 588 and/or 591, numbering based on VP1 numbering of AAVrh10. In some embodiments, the numbering is based on the VP1 of AAVrh10 comprising the amino acid sequence of SEQ ID NO:16. In some embodiments, the one or more amino acid substitutions comprise a substitution at position Q588 and/or A591, numbering based on VP1 numbering of AAVrh10. In some embodiments, the one or more amino acid substitutions comprise a Q588R or Q588K substitution, numbering based on VP1 of AAVrh10. In some embodiments, the one or more amino acid substitutions comprise an A591R substitution, numbering based on VP1 of AAVrh10.

IV. Methods of Treatment

Gene therapy protocols for retinal diseases, such as LCA, retinitis pigmentosa, and age-related macular degeneration require the localized delivery of the vector to the cells in the retina. The cells that will be the treatment target in these diseases are either the photoreceptor cells in the retina or the cells of the RPE underlying the neurosensory retina. Delivering gene therapy vectors to these cells requires injection into the subretinal space between the retina and the RPE. In some embodiments, the invention provides methods to deliver rAAV gene therapy vectors to cells of the retina where the rAAV vectors are encapsidated in AAV capsid comprising substitutions of one or more amino acid residues that interact with HSPG.

In some aspects, the invention provides methods of treating a disorder of the CNS of an individual comprising delivery of a composition comprising rAAV particles to the CNS of the individual, wherein the rAAV particles comprise (a) a rAAV capsid comprising a rAAV capsid protein comprising one or more amino acid substitutions at one or more positions that interacts with a heparan sulfate proteoglycan, and (b) a rAAV vector comprising the heterologous nucleic acid and at least one AAV terminal repeat. Further, the methods for delivering a heterologous nucleic acid to the central nervous system (CNS) of an individual, the methods for improving rAAV transduction of cells following delivery of a rAAV particle to the CNS of an individual, and the methods for improving expression of a heterologous nucleic acid following delivery of rAAV particles to the CNS of an individual described herein may be used to deliver, e.g., a heterologous nucleic acid, such as one that encodes a therapeutic polypeptide or therapeutic nucleic acid. These methods may find use, inter aha, in treating a disorder of the CNS. In some embodiments, the individual is a human.

Therapeutic Vectors

The invention provides methods of gene therapy for ocular disorders wherein rAAV particles comprising therapeutic vectors are delivered to the retina of an individual. Improved transduction of cells of the retina may be achieved by encapsidating the rAAV vectors in rAAV capsids (e.g., rAAV2, rAAVrh8R, etc. particles) where one or more amino acids of the capsid that interact with HSPG are substituted such that binding of the rAAV particles to HSPG is reduced or ablated. The vector may comprise a heterologous nucleic acid encoding a polypeptide (e.g., a therapeutic or diagnostic polypeptide) and/or a therapeutic nucleic acid. Nucleic acid which encodes therapeutic or diagnostic polypeptides and/or therapeutic nucleic acid can be generated using methods known in the art, using standard synthesis and recombinant methods. In some embodiments, the heterologous nucleic acid encodes a therapeutic polypeptide. In some embodiments, the heterologous nucleic acid encodes a diagnostic polypeptide. Non-limiting examples of nucleic acid encoding therapeutic polypeptides include: nucleic acids for replacement of a missing or mutated gene known to cause retinal disease, for example Prph2, RPE65, MERTK, RPGR, RP2, RPGRIP, CNGA3, CNGB3, and GNAT2. Other non-limiting examples of nucleic acids encoding therapeutic polypeptides include those encoding neurotrophic factors (such as GDNF, CNTF, FGF2, PEDF, EPO), anti-apoptotic genes (such as BCL2, BCL-X, NFκB), anti-angiogenic factors (such as Endostatin, Angiostatin, sFlt), and anti-inflammatory factors (such as IL10, IL1-ra, TGF, IL4). Other therapeutic polypeptides for ocular disorders include but are not limited to Myo7a, ABCA4, REP1, GUCY2D, PDE6C, RS1, RPGRIP, Lpcat1, AIPL1, RDH12, CHM. In some embodiments, the encoded polypeptide is the human variant of the polypeptide.

The nucleic acids of the invention may encode polypeptides that are intracellular proteins, anchored in the cell membrane, remain within the cell, or are secreted by the cell transduced with the vectors of the invention. For polypeptides secreted by the cell that receives the vector; the polypeptide can be soluble (i.e., not attached to the cell). For example, soluble polypeptides are devoid of a transmembrane region and are secreted from the cell. Techniques to identify and remove nucleic acid sequences which encode transmembrane domains are known in the art.

The vectors that can be administered according to the present invention also include vectors comprising a nucleic acid which encodes a RNA (e.g., RNAi, ribozymes, miRNA, siRNA, antisense RNA) that when transcribed from the nucleic acids of the vector can treat an ocular disorder by interfering with translation or transcription of an abnormal or excess protein associated with a disease state of the invention. For example, the nucleic acids of the invention may encode for an RNA which treats a disease by highly specific elimination or reduction of mRNA encoding the abnormal and/or excess proteins. Therapeutic RNA sequences include RNAi, small inhibitory RNA (siRNA), micro RNA (miRNA), and/or ribozymes (such as hammerhead and hairpin ribozymes) that can treat diseases by highly specific elimination or reduction of mRNA encoding the abnormal and/or excess proteins, such as those occurring in various forms of inherited retinal degeneration. Non-limiting examples of ocular disorders which may be treated by therapeutic RNA sequences include, for example, autosomal dominant retinitis pigmentosa (ADRP) and diabetic retinopathy. Examples of therapeutic RNA sequences and nucleic acids encoding these sequences which may be used in the invention include those described in, for example, U.S. Pat. No. 6,225,291, the disclosure of which is herein incorporated by reference in its entirety. In some embodiments, the therapeutic RNA sequence is miR-708. In some embodiments, the miR-708 is used in combination with a nucleic acid encoding a wild-type rhodopsin, either as part of the same rAAV vector or as part of a second rAAV vector. In some embodiments, the nucleic acid encoding the wild-type rhodopsin lacks the miR-708 target sequence located in 3' untranslated region of the rhodopsin gene. rAAV vectors encoding miR-708 and/or rhodopsin are provided by U.S. Provisional Patent Application Ser. No. 61/969,027, incorporated herein by reference in its entirety.

Certain aspects of the invention relate to the use of rAAV particles (e.g., a therapeutic vector) that comprise (a) a rAAV capsid comprising a rAAV capsid protein comprising one or more amino acid substitutions at one or more positions that interacts with a heparan sulfate proteoglycan, and (b) a rAAV vector comprising the heterologous nucleic acid and at least one AAV terminal repeat. In some embodiments, the heterologous nucleic acid encodes a therapeutic polypeptide or therapeutic nucleic acid. As used herein, a therapeutic nucleic acid may express any therapeutic nucleic acid of the present disclosure or any nucleic acid that encodes a therapeutic polypeptide of the present disclosure. A therapeutic nucleic acid may be used, for example, to ameliorate a symptom, prevent or delay progression, and/or provide a treatment of a disorder (e.g., a disorder described herein).

Improved transduction of cells of the CNS may be achieved by encapsidating the rAAV vectors in rAAV capsids (e.g., rAAV2, rAAVrh8R, etc.) where one or more amino acids of the capsid that interact with HSPG are substituted such that binding of the rAAV particles to HSPG is reduced or ablated. The vector may comprise a heterologous nucleic acid encoding a polypeptide (e.g., a therapeutic or diagnostic polypeptide) and/or a therapeutic nucleic acid. Nucleic acid which encodes therapeutic or diagnostic polypeptides and/or therapeutic nucleic acid can be generated using methods known in the art, using standard synthesis and recombinant methods. In some embodiments, the heterologous nucleic acid encodes a therapeutic polypeptide. In some embodiments, the heterologous nucleic acid encodes a diagnostic polypeptide. In some embodiments, the heterologous nucleic acid encodes a CNS-associated gene.

In some embodiments, the heterologous nucleic acid encodes a therapeutic nucleic acid. In some embodiments, a therapeutic nucleic acid may include without limitation an siRNA, an shRNA, an RNAi, a miRNA, an antisense RNA, a ribozyme or a DNAzyme. As such, a therapeutic nucleic acid may encode an RNA that when transcribed from the nucleic acids of the vector can treat a disorder of the invention (e.g., a disorder of the CNS) by interfering with translation or transcription of an abnormal or excess protein associated with a disorder of the invention. For example, the nucleic acids of the invention may encode for an RNA which treats a disorder by highly specific elimination or reduction of mRNA encoding the abnormal and/or excess proteins. Therapeutic RNA sequences include RNAi, small inhibitory RNA (siRNA), micro RNA (miRNA), and/or ribozymes (such as hammerhead and hairpin ribozymes) that can treat disorders by highly specific elimination or reduction of mRNA encoding the abnormal and/or excess proteins.

In some embodiments, the heterologous nucleic acid encodes a therapeutic polypeptide. A therapeutic polypeptide may, e.g., supply a polypeptide and/or enzymatic activity that is absent or present at a reduced level in a cell or organism. Alternatively, a therapeutic polypeptide may supply a polypeptide and/or enzymatic activity that indirectly counteracts an imbalance in a cell or organism. For example, a therapeutic polypeptide for a disorder related to buildup of a metabolite caused by a deficiency in a metabolic enzyme or activity may supply a missing metabolic enzyme or activity, or it may supply an alternate metabolic enzyme or activity that leads to reduction of the metabolite. A therapeutic polypeptide may also be used to reduce the activity of a polypeptide (e.g., one that is overexpressed, activated by a gain-of-function mutation, or whose activity is otherwise misregulated) by acting, e.g., as a dominant-negative polypeptide.

In some embodiments, the heterologous nucleic acid encodes a polypeptide selected from an enzyme, a neurotrophic factor, a polypeptide that is deficient or mutated in an individual with a CNS-related disorder, an antioxidant, an anti-apoptotic factor, an anti-angiogenic factor, and an anti-inflammatory factor. Such polypeptides may be used to treat disorders of the CNS by, e.g., supplying a polypeptide and/or enzymatic activity that is reduced, absent, or misregulated in a disorder of the CNS, ameliorating a cause and/or symptom of a CNS disorder, and/or mitigating damage to the CNS caused by a CNS disorder (e.g., apoptosis, inflammation, or other type of cell death). Non-limiting examples of nucleic acid encoding therapeutic polypeptides include: nucleic acids for replacement of a missing or mutated gene known to cause a disorder of the CNS, for example Prph2, RPE65, MERTK, RPGR, RP2, RPGRIP, CNGA3, CNGB3, and GNAT2. Other non-limiting examples of nucleic acids encoding therapeutic polypeptides include those encoding neurotrophic factors (such as GDNF, CNTF, FGF2, PEDF, EPO), anti-apoptotic genes (such as BCL2, BCL-X, NFκB), anti-angiogenic factors (such as Endostatin, Angiostatin, sFlt), and anti-inflammatory factors (such as IL10, IL1-ra, TGFβ, IL4). Other therapeutic polypeptides for CNS disorders include but are not limited to Myo7a, ABCA4, REP1, GUCY2D, PDE6C, RS1, RPGRIP, Lpcat1, AIPL1, RDH12, CHM. In some embodiments, the encoded polypeptide is the human variant of the polypeptide. In some embodiments, the heterologous nucleic acid encodes neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), amino acid decarboxylase (AADC), an anti-oxidant, an anti-angiogenic polypeptide, an anti-inflammatory polypeptide, and/or aspartoacylase (ASPA). Examples of anti-oxidants include without limitation SOD1; SOD2; Catalase; Sirtuins 1, 3, 4, or 5; NRF2; PGC1a; GCL (catalytic subunit); GCL (modifier subunit); adiponectin; glutathione peroxidase 1; and neuroglobin. Exanples of anti-angiogenic polypeptides include without limitation angiostatin, endostatin, PEDF, a soluble VEGF receptor, and a soluble PDGF receptor. Examples of anti-inflammatory polypeptides include without limitation IL-10, soluble IL17R, soluble TNF-R, TNF-R-Ig, an IL-1 inhibitor, and an IL18 inhibitor. Other exemplary polypeptides of these classes that may be used to treat a disorder of the CNS are provided infra.

The nucleic acids of the invention may encode polypeptides that are intracellular proteins, anchored in the cell membrane, remain within the cell, or are secreted by the cell transduced with the vectors of the invention. For polypeptides secreted by the cell that receives the vector; the polypeptide can be soluble (i.e., not attached to the cell). For example, soluble polypeptides are devoid of a transmembrane region and are secreted from the cell. Techniques to identify and remove nucleic acid sequences which encode transmembrane domains are known in the art.

In some embodiments, the heterologous nucleic acid is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., Gene, 1991, 108(2):193-9) and the elongation factor 1-alpha promoter (EF1-alpha) promoter (Kim et al., Gene, 1990, 91(2):217-23 and Guo et al., Gene Ther., 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides a recombinant vector comprising nucleic acid encoding a heterologous transgene of the present disclosure operably linked to a CBA promoter. Exemplary promoters and descriptions may be found, e.g., in U.S. PG Pub. 20140335054.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EFla promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

In some embodiments, the heterologous nucleic acid is under the control of a promoter sequence that is expressed in one or more cells of the CNS. Many of the promoter sequences listed above (e.g., a CBA promoter) are known in the art to be expressed in one or more cells of the CNS. In some embodiments, the promoter sequence may be ubiquitously expressed in an organism, and thus may express in one or more cells of the CNS by virtue of its delivery to the CNS. In other embodiments, a promoter sequence that specifically expresses in the CNS, or a subset of one or more CNS cells, may be used. In some embodiments, the heterologous nucleic acid is operably linked to a promoter suitable for expression of the therapeutic polypeptide or therapeutic nucleic acid in one or more cells of the CNS. As such, in some embodiments, a therapeutic polypeptide or a therapeutic nucleic acid of the invention may be used to treat a disorder of the CNS.

In some embodiments, the promoter expresses the heterologous nucleic acid in a brain cell. A brain cell may refer to any brain cell known in the art, including without limitation a neuron (such as a sensory neuron, motor neuron, interneuron, dopaminergic neuron, medium spiny neuron, cholinergic neuron, GABAergic neuron, pyramidal neuron, etc.), a glial cell (such as microglia, macroglia, astrocytes, oligodendrocytes, ependymal cells, radial glia, etc.), a brain parenchyma cell, microglial cell, ependemal cell, and/or a Purkinje cell. In some embodiments, the promoter expresses the heterologous nucleic acid in a neuron. In some embodiments, the heterologous nucleic acid is exclusively expressed in neurons (e.g., expressed in a neuron and not expressed in other cells of the CNS, such as glial cells).

In some aspects, the invention provides rAAV vectors for use in methods of preventing or treating one or more gene defects (e.g., heritable gene defects, somatic gene alterations, and the like) in a mammal, such as for example, a gene defect that results in a polypeptide deficiency or polypeptide excess in a subject, or for treating or reducing the severity or extent of deficiency in a subject manifesting a CNS-associated disorder linked to a deficiency in such polypeptides in cells and tissues. In some embodiments, methods involve administration of a rAAV vector that encodes one or more therapeutic peptides, polypeptides, functional RNAs, inhibitory nucleic acids, shRNAs, microRNAs, antisense nucleotides, etc. in a pharmaceutically-acceptable carrier to the subject in an amount and for a period of time sufficient to treat the CNS-associated disorder in the subject having or suspected of having such a disorder.

A rAAV vector may comprise as a transgene, a nucleic acid encoding a protein or functional RNA that modulates or treats a CNS-associated disorder. The following is a non-limiting list of genes associated with CNS-associated disorders: neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TM, GTP-cyclohydrolase (GTPCH), aspartoacylase (ASPA), superoxide dismutase (SOD1), an anti-oxidant, an anti-angiogenic polypeptide, an anti-inflammatory polypeptide, and amino acid decorboxylase (AADC). For example, a useful transgene in the treatment of Parkinson's disease encodes TH, which is a rate limiting enzyme in the synthesis of dopamine. A transgene encoding GTPCII, which generates the TII cofactor tetrahydrobiopterin, may also be used in the treatment of Parkinson's disease. A transgene encoding GDNF or BDNF, or AADC, which facilitates conversion of L-Dopa to DA, may also be used for the treatment of Parkinson's disease. For the treatment of ALS, a useful transgene may encode: GDNF, BDNF or CNTF. Also for the treatment of ALS, a useful transgene may encode a functional RNA, e.g., shRNA, miRNA, that inhibits the expression of SOD1. For the treatment of ischemia a useful transgene may encode NAIP or NGF. A transgene encoding Beta-glucuronidase (GUS) may be useful for the treatment of certain lysosomal storage diseases (e.g., Mucopolysacharidosis type VII (MPS VII)). A transgene encoding a prodrug activation gene, e.g., HSV-Thymidine kinase which converts ganciclovir to a toxic nucleotide which disrupts DNA synthesis and leads to cell death, may be useful for treating certain cancers, e.g., when administered in combination with the prodrug. A transgene encoding an endogenous opioid, such a β-endorphin may be useful for treating pain. Examples of anti-oxidants include without limitation SOD1; SOD2; Catalase; Sirtuins 1, 3, 4, or 5; NRF2; PGC1a; GCL (catalytic subunit); GCL (modifier subunit); adiponectin; glutathione peroxidase 1; and neuroglobin. Exanples of anti-angiogenic polypeptides include without limitation angiostatin, endostatin, PEDF, a soluble VEGF receptor, and a soluble PDGF receptor. Examples of anti-inflammatory polypeptides include without limitation IL-10, soluble IL17R, soluble TNF-R, TNF-R-Ig, an IL-1 inhibitor, and an IL18 inhibitor. Other examples of transgenes that may be used in the rAAV vectors of the invention will be apparent to the skilled artisan (See, e.g., Costantini L C, et al., *Gene Therapy* (2000) 7, 93-109).

In some embodiments, the therapeutic polypeptide or therapeutic nucleic acid is used to treat a disorder of the CNS. Without wishing to be bound to theory, it is thought that a therapeutic polypeptide or therapeutic nucleic acid may be used to reduce or eliminate the expression and/or activity of a polypeptide whose gain-of-function has been associated with a disorder, or to enhance the expression and/or activity of a polypeptide to complement a deficiency that has been associated with a disorder (e.g., a mutation in a gene whose expression shows similar or related activity). Non-limiting examples of disorders of the invention that may be treated by a therapeutic polypeptide or therapeutic nucleic acid of the invention (exemplary genes that may be targeted or supplied are provided in parenthesis for each disorder) include stroke (e.g., caspase-3, Beclin1, Ask1, PAR1, HIF1a, PUMA, and/or any of the genes described in Fukuda, A. M. and Badaut, J. (2013) *Genes* (Basel) 4:435-456), Huntington's disease (mutant HTT), epilepsy (e.g., SCN1A, NMDAR, ADK, and/or any of the genes described in Boison, D. (2010) *Epilepsia* 51:1659-1668), Parkinson's disease (alpha-synuclein), Lou Gehrig's disease (also known as amyotrophic lateral sclerosis; SOD1), Alzheimer's disease (tau, amyloid precursor protein), corticobasal degeneration or CBD (tau), corticogasal ganglionic degeneration or CBGD (tau), frontotemporal dementia or FTD (tau), progressive supranuclear palsy or PSP (tau), multiple system atrophy or MSA (alpha-synuclein), cancer of the brain (e.g., a mutant or overexpressed oncogene implicated in brain cancer), and lysosomal storage diseases (LSD). Disorders of the invention may include those that involve large areas of the cortex, e.g., more than one functional area of the cortex, more than one lobe of the cortex, and/or the entire cortex. Other non-limiting examples of disorders of the invention that may be treated by a therapeutic polypeptide or therapeutic nucleic acid of the invention include traumatic brain injury, enzymatic dysfunction disorders, psychiatric disorders (including post-traumatic stress syndrome), neurodegenerative diseases, and cognitive disorders (including dementias, autism, and depression). Enzymatic dysfunction disorders include without limitation leukodystrophies (including Canavan's disease) and any of the lysosomal storage diseases described below.

In some embodiments, the therapeutic polypeptide or therapeutic nucleic acid is used to treat a lysosomal storage disease. As is commonly known in the art, lysosomal storage disease are rare, inherited metabolic disorders characterized by defects in lysosomal function. Such disorders are often caused by a deficiency in an enzyme required for proper mucopolysaccharide, glycoprotein, and/or lipid metabolism, leading to a pathological accumulation of lysosomally stored cellular materials. Non-limiting examples of lysosomal storage diseases of the invention that may be treated by a therapeutic polypeptide or therapeutic nucleic acid of the invention (exemplary genes that may be targeted or supplied are provided in parenthesis for each disorder) include Gaucher disease type 2 or type 3 (acid beta-glucosidase, GBA), GM1 gangliosidosis (beta-galactosidase-1, GLB1), Hunter disease (iduronate 2-sulfatase, IDS), Krabbe disease (galactosylceramidase, GALC), a mannosidosis disease (a mannosidase, such as alpha-D-mannosidase, MAN2B1), β mannosidosis disease (beta-mannosidase, MANBA), metachromatic leukodystrophy disease (pseudoarylsulfatase A, ARSA), mucolipidosisII/III disease (N-acetylglucosamine-1-phosphotransferase, GNP TAB), Niemann-Pick A disease (acid sphingomyelinase, ASM), Niemann-Pick C disease (Niemann-Pick C protein, NPC1), Pompe disease (acid alpha-1,4-glucosidase, GAA), Sandhoff disease (hexosaminidase beta subunit, HEXB), Sanfilippo A disease (N-sulfoglucosamine sulfohydrolase, MPS3A), Sanfilippo B disease (N-alpha-acetylglucosaminidase, NAGLU), Sanfilippo C disease (heparin acetyl-CoA:alpha-glucosaminidase N-acetyltransferase, MPS3C), Sanfilippo D disease (N-acetylglucosamine-6-sulfatase, GNS), Schindler disease (alpha-N-acetylgalactosaminidase, NAGA), Sly disease (beta-glucuronidase, GUSB), Tay-Sachs disease (hexosaminidase alpha subunit, HEXA), and Wolman disease (lysosomal acid lipase, LIPA).

Additional lysosomal storage diseases, as well as the defective enzyme associated with each disease, are listed in Table 1 below. In some embodiments, a disease listed in the table below is treated by a therapeutic polypeptide or therapeutic nucleic acid of the invention that complements or otherwise compensates for the corresponding enzymatic defect.

TABLE 1

Lysosomal storage disorders and associated defective enzymes.

| Lysosomal storage disease | Defective enzyme |
|---|---|
| Aspartylglusoaminuria | Aspartylglucosaminidase |
| Fabry | Alpha-galactosidase A |
| Infantile Batten Disease (CNL1) | Palmitoyl protein thioesterase |
| Classic Late Infantile Batten Disease (CNL2) | Tripeptidyl peptidase |
| Juvenile Batten Disease (CNL3) | Lysosomal transmembrane protein |
| Batten, other forms (CNL4-CNL8) | multiple gene products |
| Cystinosis | Cysteine transporter |
| Farber | Acid ceramidase |
| Fucosidosis | Acid alpha-L-fucosidase |
| Galactosidosialidosis | Protective protein/cathepsin A |
| Gaucher types 1, 2, and 3 | Acid beta-glucosidase |
| GM1 gangliosidosis | Acid beta-galactosidase |
| Hunter | Iduronate-2-sulfatase |
| Hurler-Scheie | Alpha-L-iduronidase |
| Krabbe | Galactocerebrosidase |
| alpha-mannosidosis | Acid alpha-mannosidase |
| beta-mannosidosis | Acid beta-mannosidase |
| Maroteaux-Lamy | Arylsulfatase B |
| Metachromatic leukodystrophy | Aryl sulfatase A |
| Morquio A | N-acetylgalactosamine-6-sulfate |
| Morquio B | Acid beta-galactosidase |
| Mucolipidosis II/III | N-acetylglucosamine-1-phosphotransferase |
| Niemann-Pick A, B | Acid sphingomyelinase |
| Niemann-Pick C | NPC-1 |
| Pompe acid | alpha-glucosidase |
| Sandhoff | beta-hexosaminidase B |
| Sanfilippo A | Heparan N-sulfatase |
| Sanfilippo B | alpha-N-acetylglucosaminidase |
| Sanfilippo C | Acetyl-CoA:alpha-glucoasaminide N-acetyltransferase |

TABLE 1-continued

Lysosomal storage disorders and associated defective enzymes.

| Lysosomal storage disease | Defective enzyme |
|---|---|
| Sanfilippo D | N-acetylglucosamine-6-sulfate |
| Schindler disease | alpha-N-acetylgalactosaminidase |
| Schindler-Kanzaki | alpha-N-acetylgalactosaminidase |
| Sialidosis | alpha-neuramidase |
| Sly | beta-glucuronidase |
| Tay-Sachs | beta-hexosaminidase A |
| Wolman | Acid lipase |

Huntington's Disease

One example of a disease where such vectors may be advantageous is Huntington's disease (HD), which is caused by a CAG repeat expansion mutation that encodes an expanded polyglutamine (polyQ) repeat in the mutant huntingtin protein (mHTT). HD is an attractive target for DNA- and RNA-based therapies because it is an autosomal dominant disease resulting from mutation of a single allele. AAV vectors could provide an ideal delivery system for nucleic acid therapeutics and would allow for long lasting and continuous expression of these huntingtin lowering molecules in the brain.

As described herein, intracranial administration of rAAV particles (e.g., a therapeutic vector) having a rAAV capsid protein containing one or more amino acid substitutions at one or more positions that interacts with a heparan sulfate proteoglycan, yields widespread neuronal transduction. Accordingly, aspects of the invention provide for methods of delivering a heterologous nucleic acid to the central nervous system using the recombinant viral particles described herein for the treatment of Huntington's disease. In some embodiments, the invention provides methods and compositions for treating Huntington's disease in an individual comprising administering to the mammal a pharmaceutical composition of the present disclosure (e.g., a pharmaceutical composition comprising a variant viral particle of the present disclosure). In some aspects, the invention provides methods and compositions for inhibiting the expression of htt in a mammal with Huntington's disease comprising administering to the individual a pharmaceutical composition of the present disclosure (e.g., a pharmaceutical composition comprising a variant viral particle of the present disclosure). In some aspects, the invention provides methods and compositions for inhibiting the accumulation of htt in a cell of an individual with Huntington's disease comprising administering to the individual a pharmaceutical composition of the present disclosure (e.g., a pharmaceutical composition comprising a variant viral particle of the present disclosure).

In some aspects, the invention provides methods and compositions for ameliorating a symptom of HD in an individual, comprising administration of an effective amount of recombinant viral particles comprising one or more amino acid substitutions at one or more positions that interacts with heparan sulfate proteoglycan to the CNS of the individual, wherein the rAAV particles comprising a vector encoding an RNAi that inhibits the expression and/or accumulation of HTT in the individual. In some embodiments, the symptoms of HD include, but are not limited to, chorea, rigidity, uncontrollable body movements, loss of muscle control, lack of coordination, restlessness, slowed eye movements, abnormal posturing, instability, ataxic gait, abnormal facial expression, speech problems, difficulties chewing and/or swallowing, disturbance of sleep, seizures, dementia, cognitive deficits (e.g., diminished abilities related to planning, abstract thought, flexibility, rule acquisition, interpersonal sensitivity, self-control, attention, learning, and memory), depression, anxiety, changes in personality, aggression, compulsive behavior, obsessive-compulsive behavior, hypersexuality, psychosis, apathy, irritability, suicidal thoughts, weight loss, muscle atrophy, heart failure, reduced glucose tolerance, testicular atrophy, and osteoporosis.

In some aspects, the invention provides methods to prevent or delay progression of HD. Autosomal dominant HD is a genetic disease that can be genotyped. For example, the number of CAG repeats in HTT may be determined by PCR-based repeat sizing. This type of diagnosis may be performed at any stage of life through directly testing juveniles or adults (e.g., along with presentation of clinical symptoms), prenatal screening or prenatal exclusion testing (e.g., by chorionic villus sampling or amniocentesis), or preimplantation screening of embryos. Additionally, HD may be diagnosed by brain imaging, looking for shrinkage of the caudate nuclei and/or putamen and/or enlarged ventricles. These symptoms, combined with a family history of HD and/or clinical symptoms, may indicate HD.

Means for determining amelioration of the symptoms of HD are known in the art. For example, the Unified Huntington's Disease Rating Scale (UHDRS) may be used to assess motor function, cognitive function, behavioral abnormalities, and functional capacity (see, e.g., Huntington Study Group (1996) *Movement Disorders* 11:136-42). This rating scale was developed to provide a uniform, comprehensive test for multiple facets of the disease pathology, incorporating elements from tests such as the HD Activities and Daily Living Scale, Marsden and Quinn's chorea severity scale, the Physical Disability and Independence scales, the HD motor rating scale (HDMRS), the HD functional capacity scale (HDFCS), and the quantitated neurological exam (QNE). Other test useful for determining amelioration of HD symptoms may include without limitation the Montreal Cognitive Assessment, brain imaging (e.g., MM), Category Fluency Test, Trail Making Test, Map Search, Stroop Word Reading Test, Speeded Tapping Task, and the Symbol Digit Modalities Test.

In some aspects of the invention, the methods and compositions are used for the treatment of humans with HD. As described above, HD is inherited in an autosomal dominant manner and caused by CAG repeat expansion in the HTT gene. Juvenile-onset HD is most often inherited from the paternal side. Huntington disease-like phenotypes have also been correlated with other genetic loci, such as HDL1, PRNP, HDL2, HDL3, and HDL4. It is thought that other genetic loci may modify the manifestation of HD symptoms, including mutations in the GRIN2A, GRIN2B, MSXJ, GRIK2, and APOE genes.

rAAV Compositions

In some aspects, the invention provides compositions comprising any of the rAAV particles described herein. Generally, the compositions for use in the methods and systems of the invention comprise an effective amount of rAAV particles comprising rAAV vectors encoding a polypeptide and/or RNA, optionally in a pharmaceutically acceptable excipient. The viral particles comprise AAV capsid (e.g., an AAV2 or AAVrh8R capsid) wherein one or more amino acids that interact with HSPG is substituted such that rAAV particle binding to HSPG is reduced or ablated. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

Generally, these compositions are formulated for administration by subretinal injection. Accordingly, these compositions can be combined with pharmaceutically acceptable vehicles such as saline, Ringer's balanced salt solution (pH 7.4), and the like. Although not required, the compositions may optionally be supplied in unit dosage form suitable for administration of a precise amount.

Methods of Subretinal Delivery of rAAV

Methods of subretinal delivery are known in the art. For example, see WO 2009/105690, incorporated herein by reference. Briefly, the general method for delivering rAAV particles (e.g., rAAV2, rAAVrh8R, etc. particles) to the subretina of the macula and fovea may be illustrated by the following brief outline. This example is merely meant to illustrate certain features of the method, and is in no way meant to be limiting.

Generally, the rAAV vector can be delivered in the form of a composition injected intraocularly (subretinally) under direct observation using an operating microscope. In some embodiments the vector is encapsidated in a rAAV particle wherein the rAAV particle comprises a rAAV capsid comprising rAAV capsid proteins comprising one or more amino acid substitutions at one or more positions that interacts with a heparan sulfate proteoglycan (e.g., inhibits or ablates HSPG binding), and the rAAV vector comprising a heterologous nucleic acid and at least one AAV inverted terminal repeat. This procedure may involve vitrectomy followed by injection of rAAV vector suspension using a fine cannula through one or more small retinotomies into the subretinal space.

Briefly, an infusion cannula can be sutured in place to maintain a normal globe volume by infusion (of e.g., saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g., saline) creates space to accommodate the intraocular injection of vector, and (3) its controlled removal reduces the possibility of retinal tears and unplanned retinal detachment.

In some embodiments, the rAAV composition is directly injected into the subretinal space outside the central retina, by utilizing a cannula of the appropriate bore size (e.g., 27-45 gauge), thus creating a bleb in the subretinal space. In other embodiments, the subretinal injection of rAAV composition is preceded by subretinal injection of a small volume (e.g., about 0.1 to about 0.5 ml) of an appropriate fluid (such as saline or Ringer's solution) into the subretinal space outside the central retina. This initial injection into the subretinal space establishes an initial fluid bleb within the subretinal space, causing localized retinal detachment at the location of the initial bleb. This initial fluid bleb can facilitate targeted delivery of rAAV composition to the subretinal space (by defining the plane of injection prior to rAAV delivery), and minimize possible rAAV administration into the choroid and the possibility of rAAV injection or reflux into the vitreous cavity. In some embodiments, this initial fluid bleb can be further injected with fluids comprising one or more rAAV compositions and/or one or more additional therapeutic agents by administration of these fluids directly to the initial fluid bleb with either the same or additional fine bore cannulas.

Intraocular administration of the rAAV compositions and/or the initial small volume of fluid can be performed using a fine bore cannula (e.g., 27-45 gauge) attached to a syringe. In some embodiments, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (but outside the central retina). Under direct visualization the vector suspension is injected mechanically under the neurosensory retina causing a localized retinal detachment with a self-sealing non-expanding retinotomy. As noted above, the rAAV composition can be either directly injected into the subretinal space creating a bleb outside the central retina or the vector can be injected into an initial bleb outside the central retina, causing it to expand (and expanding the area of retinal detachment). In some embodiments, the injection of rAAV composition is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. In some embodiments, the rAAV composition is injected over about 15-17 minutes. In some embodiments, the vector is injected over about 17-20 minutes. In some embodiments, the rAAV composition is injected over about 20-22 minutes. In some embodiments, the rAAV composition is injected at a rate of about 35 to about 65 µl/min. In some embodiments, the rAAV composition is injected at a rate of about 35 µl/min. In some embodiments, the rAAV composition is injected at a rate of about 40 µl/min. In some embodiments, the rAAV composition is injected at a rate of about 45 µl/min. In some embodiments, the rAAV composition is injected at a rate of about 50 µl/min. In some embodiments, the rAAV composition is injected at a rate of about 55 µl/min. In some embodiments, the rAAV composition is injected at a rate of about 60 µl/min. In some embodiments, the rAAV composition is injected at a rate of about 65 µl/min. One of ordinary skill in the art would recognize that the rate and time of injection of the bleb may be directed by, for example, the volume of the rAAV composition or size of the bleb necessary to create sufficient retinal detachment to access the cells of central retina, the size of the cannula used to deliver the rAAV composition, and the ability to safely maintain the position of the cannula of the invention.

In some embodiments of the invention, the volume of the composition injected to the subretinal space of the retina is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, 1 mL, or any amount therebetween.

In some embodiments, the methods comprise administration to the eye (e.g., by subretinal and/or intravitreal administration) an effective amount of recombinant viral particles comprising one or more amino acid substitutions at one or more positions that interacts with heparan sulfate proteoglycan comprising a vector encoding a heterologous nucleic acid. In some embodiments, the viral titer of the composition is at least about any of $5 \times 10^{12}$, $6 \times 10^{12}$, $7 \times 10^{12}$, $8 \times 10^{12}$, $9 \times 10^{12}$, $10 \times 10^{12}$, $11 \times 10^{12}$, $15 \times 10^{12}$, $20 \times 10^{12}$, $25 \times 10^{12}$, $30 \times 10^{12}$ or $50 \times 10^{12}$ genome copies/mL. In some embodiments, the viral titer of the composition is about any of $5 \times 10^{12}$ to $6 \times 10^{12}$, $6 \times 10^{12}$ to $7 \times 10^{12}$, $7 \times 10^{12}$ to $8 \times 10^{12}$, $8 \times 10^{12}$ to $9 \times 10^{12}$, $9 \times 10^{12}$ to $10 \times 10^{12}$, $10 \times 10^{12}$ to $11 \times 10^{12}$, $11 \times 10^{12}$ to $15 \times 10^{12}$, $15 \times 10^{12}$ to $20 \times 10^{12}$, $20 \times 10^{12}$ to $25 \times 10^{12}$, $25 \times 10^{12}$ to $30 \times 10^{12}$, $30 \times 10^{12}$ to $50 \times 10^{12}$, or $50 \times 10^{12}$ to $100 \times 10^{12}$ genome copies/mL. In some embodiments, the viral titer of the composition is about any of $5 \times 10^{12}$ to $10 \times 10^{12}$, $10 \times 10^{12}$ to $25 \times 10^{12}$, or $25 \times 10^{12}$ to $50 \times 10^{12}$ genome copies/mL. In some embodiments, the viral titer of the composition is at least about any of $5 \times 10^{9}$, $6 \times 10^{9}$, $7 \times 10^{9}$, $8 \times 10^{9}$, $9 \times 10^{9}$, $10 \times 10^{9}$, $11 \times 10^{9}$, $15 \times 10^{9}$, $20 \times 10^{9}$, $25 \times 10^{9}$, $30 \times 10^{9}$, or $50 \times 10^{9}$ transducing units/mL. In some embodiments, the viral titer of the composition is about any of $5 \times 10^{9}$ to $6 \times 10^{9}$, $6 \times 10^{9}$ to $7 \times 10^{9}$, $7 \times 10^{9}$ to $8 \times 10^{9}$, $8 \times 10^{9}$ to $9 \times 10^{9}$, $9 \times 10^{9}$ to $10 \times 10^{9}$, $10 \times 10^{9}$ to $11 \times 10^{9}$, $11 \times 10^{9}$ to $15 \times 10^{9}$, $15 \times 10^{9}$ to $20 \times 10^{9}$, $20 \times 10^{9}$ to $25 \times 10^{9}$, $25 \times 10^{9}$ to $30 \times 10^{9}$, $30 \times 10^{9}$ to $50 \times 10^{9}$ or $50 \times 10^{9}$ to $100 \times 10^{9}$ transducing units/mL. In some embodiments, the viral titer of the composition is about any of $5 \times 10^{9}$ to $10 \times 10^{9}$, $10 \times 10^{9}$ to $15 \times 10^{9}$, $15 \times 10^{9}$ to $25 \times 10^{9}$, or $25 \times 10^{9}$ to $50 \times 10^{9}$ transducing units/mL. In some embodiments, the viral titer of the composition is at least any of about $5 \times 10^{10}$, $6 \times 10^{10}$, $7 \times 10^{10}$, $8 \times 10^{10}$, $9 \times 10^{10}$, $10 \times 10^{10}$, $11 \times 10^{10}$, $15 \times 10^{10}$, $20 \times 10^{10}$, $25 \times 10^{10}$, $30 \times 10^{10}$, $40 \times 10^{10}$, or $50 \times 10^{10}$ infectious units/mL. In some embodiments, the viral titer of the composition is at least any of about $5 \times 10^{10}$ to $6 \times 10^{10}$, $6 \times 10^{10}$ to $7 \times 10^{10}$, $7 \times 10^{10}$ to $8 \times 10^{10}$, $8 \times 10^{10}$ to $9 \times 10^{10}$, $9 \times 10^{10}$ to $10 \times 10^{10}$, $10 \times 10^{10}$ to $11 \times 10^{10}$, $11 \times 10^{10}$ to $15 \times 10^{10}$, $15 \times 10^{10}$ to $20 \times 10^{10}$, $20 \times 10^{10}$ to $25 \times 10^{10}$, $25 \times 10^{10}$ to $30 \times 10^{10}$, $30 \times 10^{10}$ to $40 \times 10^{10}$, $40 \times 10^{10}$ to $50 \times 10^{10}$, or $50 \times 10^{10}$ to $100 \times 10^{10}$ infectious units/mL. In some embodiments, the viral titer of the composition is at least any of about $5 \times 10^{10}$ to $10 \times 10^{10}$, $10 \times 10^{10}$ to $15 \times 10^{10}$, $15 \times 10^{10}$ to $25 \times 10^{10}$, or $25 \times 10^{10}$ to $50 \times 10^{10}$, infectious units/mL.

In some embodiments, the methods comprise administration to the eye (e.g., by subretinal and/or intravitreal administration) of an individual (e.g., a human) an effective amount of recombinant viral particles comprising one or more amino acid substitutions at one or more positions that interacts with heparan sulfate proteoglycan. In some embodiments, the dose of viral particles administered to the individual is at least about any of $1 \times 10^{8}$ to about $1 \times 10^{13}$ genome copies/kg of body weight. In some embodiments, the dose of viral particles administered to the individual is about any of $1 \times 10^{8}$ to about $1 \times 10^{13}$ genome copies/kg of body weight.

One or multiple (e.g., 2, 3, or more) blebs can be created. Generally, the total volume of bleb or blebs created by the methods and systems of the invention cannot exceed the fluid volume of the eye, for example about 4 ml in a typical human subject. The total volume of each individual bleb can be at least about 0.3 ml, or at least about 0.5 ml in order to facilitate a retinal detachment of sufficient size to expose the cell types of the central retina and create a bleb of sufficient dependency for optimal manipulation. One of ordinary skill in the art will appreciate that in creating the bleb according to the methods and systems of the invention that the appropriate intraocular pressure must be maintained in order to avoid damage to the ocular structures. The size of each individual bleb may be, for example, about 0.5 to about 1.2 ml, about 0.8 to about 1.2 ml, about 0.9 to about 1.2 ml, about 0.9 to about 1.0 ml, about 1.0 to about 2.0 ml, about 1.0 to about 3.0 ml. Thus, in one example, to inject a total of 3 ml of rAAV composition suspension, 3 blebs of about 1 ml each can be established. The total volume of all blebs in combination may be, for example, about 0.5 to about 3.0 ml, about 0.8 to about 3.0 ml, about 0.9 to about 3.0 ml, about 1.0 to about 3.0 ml, about 0.5 to about 1.5 ml, about 0.5 to about 1.2 ml, about 0.9 to about 3.0 ml, about 0.9 to about 2.0 ml, about 0.9 to about 1.0 ml.

In order to safely and efficiently transduce areas of target retina (e.g., the central retina) outside the edge of the original location of the bleb, the bleb may be manipulated to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area typically resists detachment by subretinal injection. In some embodiments fluid-air exchange is utilized to reposition the bleb; fluid from the infusion cannula is temporarily replaced by air, e.g., from blowing air onto the surface of the retina. As the volume of the air displaces vitreous cavity fluid from the surface of the retina, the fluid in the vitreous cavity may flow out of a cannula. The temporary lack of pressure from the vitreous cavity fluid causes the bleb to move and gravitate to a dependent part of the eye. By positioning the eye globe appropriately, the bleb of subretinal rAAV composition is manipulated to involve adjacent areas (e.g., the macula and/or fovea). In some cases, the mass of the bleb is sufficient to cause it to gravitate, even without use of the fluid-air exchange. Movement of the bleb to the desired location may further be facilitated by altering the position of the subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal rAAV composition may be left in situ without retinopexy to the retinotomy and without intraocular tamponade, and the retina will spontaneously reattach within about 48 hours.

By safely and effectively transducing ocular cells (e.g., RPE and/or photoreceptor cells of e.g., the macula and/or fovea) with a vector comprising a therapeutic polypeptide or RNA sequence, the methods of the invention may be used to treat an individual; e.g., a human, having an ocular disorder, wherein the transduced cells produce the therapeutic polypeptide or RNA sequence in an amount sufficient to treat the ocular disorder. In some embodiments, transduction of ocular cells is improved by using rAAV particles (e.g., rAAV2, rAAVrh8R, etc. particles) comprising AAV capsid proteins comprising one or more substitutions of amino acids that interact with HSPG (e.g., inhibit or ablate binding to HSPG). In some embodiments, the rAAV particles demonstrate reduced binding to HSPG; e.g., reduced by greater than about 10%, 25%, 50%, 75%, 100% or any number therebetween. In some embodiments, rAAV binding to HSPG is reduces by about 5% to about 100%, by about 10% to about 50%, by about 10% to about 30%, by about 25% to about 75%, by about 25% to about 50%, or by about 30% to about 50%.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As discussed above, substitution of one or more amino acids of the rAAV capsid that interacts with HSPG improves rAAV transduction. As a guide, the number of particles administered per injection is generally between about $1 \times 10^6$ and about $1 \times 10^{14}$ particles, between about $1 \times 10^7$ and $1 \times 10^{13}$ particles, between about $1 \times 10^9$ and $1 \times 10^{12}$ particles or about $1 \times 10^{11}$ particles. The rAAV composition may be administered by one or more subretinal injections, either during the same procedure or spaced apart by days, weeks, months, or years. In some embodiments, multiple vectors may be used to treat the human.

In some embodiments, the administration to the retina of an effective amount of rAAV viral particles comprising a rAAV capsid with one or more substitutions of amino acids that interact with HSPG transduces photoreceptor cells at or near the site of administration. In some embodiments, more than about any of 5%, 10%, 15%, 20%, 25%, 30%, 35%, 40%, 45%, 50%, 55%, 60%, 65%, 70%, 75% or 100% of photoreceptor cells are transduced. In some embodiments, about 5% to about 100%, about 10% to about 50%, about 10% to about 30%, about 25% to about 75%, about 25% to about 50%, or about 30% to about 50% of the photoreceptor cells are transduced. Methods to identify photoreceptor cells transduced by AAV viral particles comprising a rAAV capsid with one or more substitutions of amino acids that interact with HSPG are known in the art; for example, immunohistochemistry or the use of a marker such as enhanced green fluorescent protein can be used to detect transduction of viral particles comprising a rAAV capsid with one or more substitutions of amino acids that interact with HSPG.

In some embodiments of the invention, the methods comprise administration to the subretina (e.g., the subretinal space) of a mammal an effective amount of AAV viral particles viral particles comprising a rAAV capsid with one or more substitutions of amino acids that interact with HSPG for treating an individual with an ocular disorder; e.g., a human with an ocular disorder. In some embodiments, the composition is injected to one or more locations in the subretina to allow expression of a heterologous nucleic acid in photoreceptor cells. In some embodiments, the composition is injected into any one of one, two, three, four, five, six, seven, eight, nine, ten or more than ten locations in the subretina.

In some embodiments the rAAV viral particles comprising a rAAV capsid with one or more substitutions of amino acids that interact with HSPG are administered to more than one location simultaneously or sequentially. In some embodiment, multiple injections of rAAV viral particles are no more than one hour, two hours, three hours, four hours, five hours, six hours, nine hours, twelve hours or 24 hours apart.

Methods of Intravitreal Injection

The general method for intravitreal injection may be illustrated by the following brief outline. This example is merely meant to illustrate certain features of the method, and is in no way meant to be limiting. Procedures for intravitreal injection are known in the art (see, e.g., Peyman, G. A., et al. (2009) *Retina* 29(7):875-912 and Fagan, X. J. and Al-Qureshi, S. (2013) *Clin. Experiment. Ophthalmol.* 41(5): 500-7).

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site.

In some embodiments, the methods comprise administration to the eye (e.g., by subretinal and/or intravitreal administration) an effective amount of recombinant viral particles comprising one or more amino acid substitutions at one or more positions that interacts with heparan sulfate proteoglycan comprising a vector encoding a heterologous nucleic acid. In some embodiments, the viral titer of the composition is at least about any of $5\times10^{12}$, $6\times10^{12}$, $7\times10^{12}$, $8\times10^{12}$, $9\times10^{12}$, $10\times10^{12}$, $10\times10^{12}$, $15\times10^{12}$, $20\times10^{12}$, $25\times10^{12}$, $30\times10^{12}$, or $50\times10^{12}$ genome copies/mL. In some embodiments, the viral titer of the composition is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the composition is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the composition is at least about any of $5\times10^{9}$, $6\times10^{9}$, $7\times10^{9}$, $8\times10^{9}$, $9\times10^{9}$, $10\times10^{9}$, $11\times10^{9}$, $15\times10^{9}$, $20\times10^{9}$, $25\times10^{9}$, $30\times10^{9}$, or $50\times10^{9}$ transducing units/mL. In some embodiments, the viral titer of the composition is about any of $5\times10^{9}$ to $6\times10^{9}$, $6\times10^{9}$ to $7\times10^{9}$, $7\times10^{9}$ to $8\times10^{9}$, $8\times10^{9}$ to $9\times10^{9}$, $9\times10^{9}$ to $10\times10^{9}$, $10\times10^{9}$ to $11\times10^{9}$, $11\times10^{9}$ to $15\times10^{9}$, $15\times10^{9}$ to $20\times10^{9}$, $20\times10^{9}$ to $25\times10^{9}$, $25\times10^{9}$ to $30\times10^{9}$, $30\times10^{9}$ to $50\times10^{9}$ or $50\times10^{9}$ to $100\times10^{9}$ transducing units/mL. In some embodiments, the viral titer of the composition is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL. In some embodiments, the viral titer of the composition is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL. In some embodiments, the viral titer of the composition is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL. In some embodiments, the viral titer of the composition is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL.

In some embodiments, the methods comprise administration to the eye (e.g., by subretinal and/or intravitreal administration) of an individual (e.g., a human) an effective amount of recombinant viral particles comprising one or more amino acid substitutions at one or more positions that interacts with heparan sulfate proteoglycan. In some embodiments, the dose of viral particles administered to the individual is at least about any of $1\times10^{8}$ to about $1\times10^{13}$ genome copies/kg of body weight. In some embodiments, the dose of viral particles administered to the individual is about any of $1\times10^{8}$ to about $1\times10^{13}$ genome copies/kg of body weight.

During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

Structure of Retina and Means to Determine Effectiveness of rAAV Delivery

The retina is known to contain multiple layers. Cell layers in the retina may include the inner limiting membrane, nerve fiber, ganglion cell, inner plexiform, inner nuclear, outer plexiform, outer nuclear, external limiting membrane, photoreceptor, and retinal pigment epithelium layers. The layer most proximal to the vitreous is the inner limiting membrane. This layer may contain Müller cells, a class of glia. The nerve fiber layer may contain axons from ganglion cells that form the optic nerve. The ganglion cell layer may include ganglion cells and amacrine cells. The inner plexiform layer may contain synapses between dendrites of the ganglion and amacrine cells and axons of the bipolar cells. The inner nuclear layer may contain cell nuclei of amacrine, bipolar, and horizontal cells. The outer plexiform layer may contain synapses between horizontal cell dendrites and photoreceptor cell projections. The outer nuclear layer may contain photoreceptor cell bodies. The external or outer limiting membrane may include cell connections, such as adherens junctions and desmosomes, among Müller cell apical processes and between these processes and photoreceptor cell inner segments. The photoreceptor layer, also known as the layer of rod and cones and Jacob's membrane, may contain photoreceptor cells include rods and cones. The retinal layer most distal to the vitreous is the retinal pigment epithelium (RPE), which may include a layer of hexagonal epithelial cells containing pigment granules.

The retina is also known to contain many different cell types. Retinal neurons may include photoreceptor cells, bipolar cells, ganglion cells, amacrine cells, and horizontal cells. Photoreceptor cells are sensitive to light. They may sense light and respond by transmitting signals to the optic nerve through the bipolar cells and the ganglion cells. Photoreceptor cells may include rod cells, which generally sense light in low-light conditions, and cone cells, which generally sense color and brighter light perception. Bipolar cells may receive inputs from photoreceptor cells and synapse onto amacrine or ganglion cells. Ganglion cells may receive information from amacrine cells or horizontal cells, and their axons form the optic nerve. Horizontal cells may integrate inputs from multiple photoreceptors and aid in adjustment to light levels. Amacrine cells are interneurons that help regulate bipolar cells and provide inputs to ganglion cells. Glial cells of the retina may include Müller cells, astroglia, and microglia.

The effectiveness of rAAV delivery by subretinal or intravitreal injection can be monitored by several criteria as described herein. For example, after treatment in a subject using methods of the present invention, the subject may be assessed for e.g., an improvement and/or stabilization and/or delay in the progression of one or more signs or symptoms of the disease state by one or more clinical parameters including those described herein. Examples of such tests are known in the art, and include objective as well as subjective (e.g., subject reported) measures. For example, to measure the effectiveness of a treatment on a subject's visual function, one or more of the following may be evaluated: the subject's subjective quality of vision or improved central vision function (e.g., an improvement in the subject's ability to read fluently and recognize faces), the subject's visual mobility (e.g., a decrease in time needed to navigate a maze), visual acuity (e.g., an improvement in the subject's Log-MAR score), microperimetry (e.g., an improvement in the subject's dB score), dark-adapted perimetry (e.g., an improvement in the subject's dB score), fine matrix mapping (e.g., an improvement in the subject's dB score), Goldmann perimetry (e.g., a reduced size of scotomatous area (i.e. areas of blindness) and improvement of the ability to resolve smaller targets), flicker sensitivities (e.g., an improvement in Hertz), autofluorescence, and electrophysiology measurements (e.g., improvement in ERG). In some embodiments, the visual function is measured by the subject's visual mobility. In some embodiments, the visual function is measured by the subject's visual acuity. In some embodiments, the visual function is measured by microperimetry. In some embodiments, the visual function is measured by dark-adapted perimetry. In some embodiments, the visual function is measured by ERG. In some embodiments, the visual function is measured by the subject's subjective quality of vision.

In the case of diseases resulting in progressive degenerative visual function, treating the subject at an early age may not only result in a slowing or halting of the progression of the disease, it may also ameliorate or prevent visual function loss due to acquired amblyopia. Amblyopia may be of two types. In studies in nonhuman primates and kittens that are kept in total darkness from birth until even a few months of age, the animals even when subsequently exposed to light are functionally irreversibly blind despite having functional signals sent by the retina. This blindness occurs because the neural connections and "education" of the cortex is developmentally is arrested from birth due to stimulus arrest. It is unknown if this function could ever be restored. In the case of diseases of retinal degeneration, normal visual cortex circuitry was initially "learned" or developmentally appropriate until the point at which the degeneration created significant dysfunction. The loss of visual stimulus in terms of signaling in the dysfunctional eye creates "acquired" or "learned" dysfunction ("acquired amblyopia"), resulting in the brain's inability to interpret signals, or to "use" that eye. It is unknown in these cases of "acquired amblyopia" whether with improved signaling from the retina as a result of gene therapy of the amblyopic eye could ever result in a gain of more normal function in addition to a slowing of the progression or a stabilization of the disease state. In some embodiments, the human treated is less than 30 years of age. In some embodiments, the human treated is less than 20 years of age. In some embodiments, the human treated is less than 18 years of age. In some embodiments, the human treated is less than 15 years of age. In some embodiments, the human treated is less than 14 years of age. In some embodiments, the human treated is less than 13 years of age. In some embodiments, the human treated is less than 12 years of age. In some embodiments, the human treated is less than 10 years of age. In some embodiments, the human treated is less than 8 years of age. In some embodiments, the human treated is less than 6 years of age.

In some ocular disorders, there is a "nurse cell" phenomena, in which improving the function of one type of cell improves the function of another. For example, transduction of the RPE of the central retina by a rAAV of the invention may then improve the function of the rods, and in turn, improved rod function results in improved cone function. Accordingly, treatment of one type of cell may result in improved function in another.

The selection of a particular rAAV vector and composition depend on a number of different factors, including, but not limited to, the individual human's medical history and features of the condition and the individual being treated. The assessment of such features and the design of an appropriate therapeutic regimen is ultimately the responsibility of the prescribing physician.

In some embodiments, the human to be treated has a genetic ocular disorder, but has not yet manifested clinical signs or symptoms. In some embodiments, the human to be treated has an ocular disorder. In some embodiments, the human to be treated has manifested one or more signs or symptoms of an ocular disorder.

Non-limiting examples of ocular disorders which may be treated by the systems and methods of the invention include: autosomal recessive severe early-onset retinal degeneration (Leber's Congenital Amaurosis), congenital achromatopsia, Stargardt's disease, Best's disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, posterior uveitis, choroideremia, and Leber hereditary optic neuropathy.

Compositions of the invention (e.g., AAV viral particles for subretinal or intravitreal delivery comprising an AAV capsid with one or more substitutions of amino acids that interact with HSPG or at one or more positions corresponding to amino acids 484, 487, 532, 585 or 588) can be used either alone or in combination with one or more additional therapeutic agents for treating ocular disorders. The interval between sequential administration can be in terms of at least (or, alternatively, less than) minutes, hours, or days.

In some embodiments, one or more additional therapeutic agents may be administered to the subretina or vitreous (e.g., through intravitreal administration). Non-limiting examples of the additional therapeutic agent include polypeptide neurotrophic factors (e.g., GDNF, CNTF, BDNF, FGF2, PEDF, EPO), polypeptide anti-angiogenic factors (e.g., sFlt, angiostatin, endostatin), anti-angiogenic nucleic acids (e.g., siRNA, miRNA, ribozyme), for example anti-angiogenic nucleic acids against VEGF, anti-angiogenic morpholinos, for example anti-angiogenic morpholinos against VEGF, anti-angiogenic antibodies and/or anti-body fragments (e.g., Fab fragments), for example anti-angiogenic antibodies and/or anti-body fragments against VEGF.

Methods for CNS delivery

In some embodiments, the administration of an effective amount of recombinant viral particles (e.g., AAV2, AAVrh8R particles, etc.) comprising one or more amino acid substitutions at one or more positions that interacts with heparan sulfate proteoglycan of the present disclosure transduces neurons (e.g., striatal neurons, such as spiny neurons) at or near the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing a heterologous nucleic acid are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some embodiments of the invention, the methods comprise administration to the brain of a mammal an effective amount of recombinant viral particles recombinant viral particles comprising one or more amino acid substitutions at one or more positions that interacts with heparan sulfate proteoglycan of the present disclosure for treating a mammal, e.g., a human. In some embodiments, the composition is injected to one or more locations in the brain to allow expression of a heterologous nucleic acid of the present disclosure in at least the neurons. In some embodiments, the composition is injected into any one of one, two, three, four, five, six, seven, eight, nine, ten or more than ten locations in the brain. In some embodiments, the composition is injected into the striatum. In some embodiments, the composition is injected into the dorsal striatum. In some embodiments, the composition is injected into the putamen. In some embodiments, the composition is injected into the caudate nucleus. In some embodiments, the composition is injected into the putamen and into the caudate nucleus. In some embodiments, the recombinant viral particles comprising one or more amino acid substitutions at one or more positions that interacts with heparan sulfate proteoglycan are administered to the CNS of an individual by stereotaxic injection, for example to the striatum. In some embodiments, the recombinant viral particles comprising one or more amino acid substitutions at one or more positions that interacts with heparan sulfate proteoglycan are administered to the CNS of an individual by convection enhanced delivery (CED); for example CED to the striatum.

Administration of the rAAV particles may be conducted through various routes. In some embodiments, the administration includes direct spinal cord injection and/or intracerebral administration. In some embodiments, the administration is at a site selected from the cerebrum, medulla, pons, cerebellum, intracranial cavity, meninges surrounding the brain, dura mater, arachnoid mater, pia mater, cerebrospinal fluid (CSF) of the subarachnoid space surrounding the brain, deep cerebellar nuclei of the cerebellum, ventricular system of the cerebrum, subarachnoid space, striatum, cortex, septum, thalamus, hypothalamus, and the parenchyma of the brain. In some embodiments, the administration comprises intracerebroventricular injection into at least one cerebral lateral ventricle. In some embodiments, the administration comprises intrathecal injection in the cervical, thoracic, and/or lumbar region. In some embodiments, the administration comprises intrastriatal injection. In some embodiments, the administration comprises intrathalamic injection. Various techniques and devices suitable for these routes of administration are described herein, e.g., CED and/or stereotaxic injection.

In some embodiments, the recombinant viral particles comprising one or more amino acid substitutions at one or more positions that interacts with heparan sulfate proteoglycan are administered to one hemisphere of the brain. In some embodiments, the recombinant viral particles are administered to both hemispheres of the brain.

In some embodiments the recombinant viral particles comprising one or more amino acid substitutions at one or more positions that interacts with heparan sulfate proteoglycan are administered to more than one location simultaneously or sequentially. In some embodiment, multiple injections of recombinant viral particles are no more than one hour, two hours, three hours, four hours, five hours, six hours, nine hours, twelve hours or 24 hours apart.

In some embodiments, the invention provides a method for treating a human with a disorder of the CNS by administering an effective amount of a pharmaceutical composition comprising a recombinant viral particles comprising one or more amino acid substitutions at one or more positions that interacts with heparan sulfate proteoglycan of the present disclosure to treat the disorder of the CNS. In some embodiments, the pharmaceutical composition comprises one or more pharmaceutically acceptable excipients.

Generally, from about 1 µl, to about 1 mL of a composition of the invention can be delivered (e.g., from about 100 µL to about 500 µL of a composition). In some embodiments of the invention, the volume of the recombinant viral particles comprising one or more amino acid substitutions at one or more positions that interacts with heparan sulfate proteoglycan injected to the striatum is about or more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

In some embodiments, a first volume of the recombinant viral particles comprising one or more amino acid substitutions at one or more positions that interacts with heparan sulfate proteoglycan is injected into a first region of the brain, and a second volume of the variant rAAV particles is injected into a second region of the brain. For example, in some embodiments, a first volume of the variant rAAV particles is injected into the caudate nucleus, and a second volume of the composition is injected into the putamen. In some embodiments, a 1× volume of the variant rAAV particles is injected into the caudate nucleus, and a 1.5×, 2×, 2.5×, 3×, 3.5×, or 4× volume of the variant rAAV particles is injected into the putamen, where X is a volume that is about or more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

Compositions of the invention (e.g., recombinant viral particles comprising one or more amino acid substitutions at one or more positions that interacts with heparan sulfate proteoglycan of the present disclosure) can be used either alone or in combination with one or more additional therapeutic agents for treating a disorder of the CNS (e.g., HD). The interval between sequential administration can be in terms of at least (or, alternatively, less than) minutes, hours, or days.

In some embodiments, the methods comprise administration to CNS an effective amount of recombinant viral particles comprising one or more amino acid substitutions at one or more positions that interacts with heparan sulfate proteoglycan comprising a vector encoding a heterologous nucleic acid. In some embodiments, the viral titer of the composition is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$, or $50\times10^{12}$ genome copies/mL. In some embodiments, the viral titer of the composition is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the composition is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the composition is at least about any of $5\times10^9$, $6\times10^9$, $7\times10^9$, $8\times10^9$, $9\times10^9$, $10\times10^9$, $11\times10^9$, $15\times10^9$, $20\times10^9$, $25\times10^9$, $30\times10^9$, or $50\times10^9$ transducing units/mL. In some embodiments, the viral titer of the composition is about any of $5\times10^9$ to $6\times10^9$, $6\times10^9$ to $7\times10^9$, $7\times10^9$ to $8\times10^9$, $8\times10^9$ to $9\times10^9$, $9\times10^9$ to $10\times10^9$, $10\times10^9$ to $11\times10^9$, $11\times10^9$ to $15\times10^9$, $15\times10^9$ to $20\times10^9$, $20\times10^9$ to $25\times10^9$, $25\times10^9$ to $30\times10^9$, $30\times10^9$ to $50\times10^9$ or $50\times10^9$ to $100\times10^9$ transducing units/mL. In some embodiments, the viral titer of the composition is about any of $5\times10^9$ to $10\times10^9$, $10\times10^9$ to $15\times10^9$, $15\times10^9$ to $25\times10^9$, or $25\times10^9$ to $50\times10^9$ transducing units/mL. In some embodiments, the viral titer of the composition is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL. In some embodiments, the viral titer of the composition is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL. In some embodiments, the viral titer of the composition is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL.

In some embodiments, the methods comprise administration to CNS of an individual (e.g., a human) an effective amount of recombinant viral particles comprising one or more amino acid substitutions at one or more positions that interacts with heparan sulfate proteoglycan. In some embodiments, the dose of viral particles administered to the individual is at least about any of $1\times10^{8}$ to about $1\times10^{13}$ genome copies/kg of body weight. In some embodiments, the dose of viral particles administered to the individual is about any of $1\times10^{8}$ to about $1\times10^{13}$ genome copies/kg of body weight.

In some embodiments, the methods comprise administration to the CNS of an individual (e.g., a human) an effective amount of recombinant viral particles comprising one or more amino acid substitutions at one or more positions that interacts with heparan sulfate proteoglycan to an individual. In some embodiments, the total amount of viral particles administered to the individual is at least about any of $1\times10^{9}$ to about $1\times10^{14}$ genome copies. In some embodiments, the total amount of viral particles administered to the individual is about any of $1\times10^{9}$ to about $1\times10^{14}$ genome copies.

V. Expression Constructs

In some aspects, the invention provides methods of delivery of heterologous nucleic acid to the eye by subretinal delivery of a rAAV vector comprising the heterologous nucleic acid and wherein the rAAV vector is encapsidated in a rAAV capsid (e.g., a rAAV2 capsid, an rAAVrh8R capsid, etc.) comprising one or more substitutions of amino acids that interact with HSPG. In some aspects, the invention provides methods of treating a disorder of the CNS of an individual comprising delivery of a composition comprising rAAV particles to the CNS of the individual, wherein the rAAV particles comprise (a) a rAAV capsid comprising a rAAV capsid protein comprising one or more amino acid substitutions at one or more positions that interacts with a heparan sulfate proteoglycan, and (b) a rAAV vector comprising the heterologous nucleic acid and at least one AAV terminal repeat. In some embodiments, the heterologous nucleic acid (e.g., a transgene) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene,* 1991, 108(2):193-9) and the elongation factor 1-alpha promoter (EF1-alpha) promoter (Kim et al., *Gene,* 1990, 91(2):217-23 and Guo et al., *Gene Ther.,* 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the promoter is capable of expressing the heterologous nucleic acid in a cell of the eye. In some embodiments, the promoter is capable of expressing the heterologous nucleic acid in photoreceptor cells or RPE. In embodiments, the promoter is a rhodopsin kinase (RK) promoter; e.g., a human RK promoter. In some embodiments, the promoter is an opsin promoter; e.g., a human opsin promoter or a mouse opsin promoter.

The present invention contemplates the use of a recombinant viral genome for introduction of one or more nucleic acid sequences encoding a therapeutic polypeptide and/or nucleic acid for packaging into a rAAV viral particle comprising one or more substitutions of amino acids that interact with HSPG. The recombinant viral genome may include any element to establish the expression of the therapeutic polypeptide and/or nucleic acid, for example, a promoter, an ITR, a ribosome binding element, terminator, enhancer, selection marker, intron, polyA signal, and/or origin of replication.

In some embodiments, the rAAV vector is a self-complementary rAAV vector, e.g., one that comprises a recombinant self-complementing (the term "self-complementary may be used interchangeably herein) genome. AAV viral particles with self-complementing genomes and methods of use of" self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the vector comprises first nucleic acid sequence encoding the heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence and a second heterologous nucleic acid sequence are linked by a mutated ITR (e.g., the right ITR). In some embodiments, the ITR comprises the polynucleotide sequence 5'-ACTCCCTCTCTGCGCGCTCGCTCGCT-CACTGAGGCCGGGCGACCAAAGGTCGCCCA CGCCCGGGCTTTGCCCGGGCG-3' (SEQ ID NO:8). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

VI. Viral Particles and Methods of Producing Viral Particles rAAV Viral Particles In some aspects, the invention provides methods of delivery of heterologous nucleic acid to the eye by subretinal delivery of a rAAV vector comprising the heterologous nucleic acid and wherein the rAAV vector is encapsidated in a rAAV capsid (e.g., rAAV2, rAAVrh8R, etc.) comprising one or more substitutions of amino acids that interact with HSPG. In some aspects, the invention provides methods and kits related to the delivery of rAAV particles to the CNS of an individual.

In some embodiments, the rAAV particle comprises a rAAV vector. In some embodiments, the viral particle is a recombinant AAV particle comprising a nucleic acid comprising a heterologous transgene flanked by one or two AAV inverted terminal repeats (ITRs). The nucleic acid is encapsidated in the AAV particle. The AAV particle also comprises capsid proteins. In some embodiments, the nucleic acid comprises the coding sequence(s) of interest (e.g., a heterologous transgene) operatively linked components in the direction of transcription, control sequences including transcription initiation and termination sequences, thereby forming an expression cassette.

The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12): 6799-810.

Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV ITRs or the like. In some embodiments, the nucleic acid in the AAV comprises an ITR of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like. In certain embodiments, the nucleic acid in the AAV comprises an AAV2 ITR. As described supra, the rAAV particles may further comprise a capsid comprising rAAV capsid proteins comprising one or more amino acid substitutions at one or more positions that interacts with a heparan sulfate proteoglycan.

In some embodiments, a vector may include a stuffer nucleic acid. In some embodiments, the stuffer nucleic acid may encode a green fluorescent protein. In some embodiments, the stuffer nucleic acid may be located between the promoter and the nucleic acid encoding the RNAi.

Different AAV serotypes are used to optimize transduction of particular target cells or to target specific cell types within a particular target tissue (e.g., a CNS tissue). A rAAV particle can comprise viral proteins and viral nucleic acids of the same serotype or a mixed serotype. For example, in some embodiments a rAAV particle can comprise AAV2 capsid proteins of the invention and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV2 capsid of the invention. In some embodiments, the invention provides rAAV particles comprising an AAVrh8R capsid of the invention.

Production of AAV Particles

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (such as a therapeutic transgene) flanked by at least one AAV ITR sequences; and 5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

The rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified.

In some embodiments, rAAV particles may be produced by a producer cell line method, such as the exemplary producer cell line method provided infra (see also (referenced in Martin et al., (2013) *Human Gene Therapy Methods* 24:253-269). Briefly, a cell line (e.g., a HeLa cell line) may be stably transfected with a plasmid containing a rep gene, a capsid gene, and a promoter-transgene sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) a rAAV pro-vector comprising a nucleic acid encoding a therapeutic polypeptide and/or nucleic acid as described herein flanked by at least one AAV ITR, and (iii) an AAV helper function; and (b) recovering the rAAV particles produced by the host cell. In some embodiments, said at least one AAV ITR is selected from the group consisting of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like. In some embodiments, said encapsidation protein comprises one or more amino acid substitutions at one or more positions that interacts with a heparan sulfate proteoglycan. In some embodiments, the encapsidation protein is an AAV2 encapsidation protein. In some embodiments, the encapsidation protein is an AAVrh8R encapsidation protein.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XL1O Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. In some embodiments, the method comprises all the steps in the order as described below. Methods to purify rAAV particles are found, for example, in Xiao et al., (1998) *Journal of Virology* 72:2224-2232; U.S. Pat. Nos. 6,989,264 and 8,137,948; and WO 2010/148143.

Also provided herein are pharmaceutical compositions comprising a rAAV particle comprising a heterologous nucleic acid encoding a therapeutic polypeptide and/or therapeutic nucleic acid, wherein the rAAV particle comprises a rAAV capsid comprising one or more substitutions or amino acids that interact with HSPG, and a pharmaceutically acceptable carrier. The pharmaceutical compositions may be suitable for any mode of administration described herein; for example, by subretinal administration.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Systems & Kits

The rAAV compositions as described herein may be contained within a system designed for use in one of the methods of the invention as described herein.
Subretinal Delivery In some embodiments, the invention provides a system for subretinal delivery of a vector to an eye of an individual, comprising a) a composition comprising an effective amount of rAAV particles, wherein i) a capsid protein of the rAAV particles comprises one or more amino acid substitutions at one or more positions that interacts with a heparan sulfate proteoglycan, and ii) the vector comprises a heterologous nucleic acid encoding a therapeutic polypeptide or therapeutic RNA and at least one AAV terminal repeat; and b) a device for retinal delivery of the rAAV.

Generally, the system comprises a fine-bore cannula, wherein the cannula is 27 to 45 gauge, one or more syringes (e.g., 1, 2, 3, 4 or more), and one or more fluids (e.g., 1, 2, 3, 4 or more) suitable for use in the methods of the invention.

The fine bore cannula is suitable for subretinal injection of the vector suspension and/or other fluids to be injected into the subretinal space. In some embodiments, the cannula is 27 to 45 gauge. In some embodiments, the fine-bore cannula is 35-41 gauge. In some embodiments, the fine-bore cannula is 40 or 41 gauge. In some embodiments, the fine-bore cannula is 41-gauge. The cannula may be any suitable type of cannula, for example, a de-Juan® cannula or an Eagle® cannula.

The syringe may be any suitable syringe, provided it is capable of being connected to the cannula for delivery of a fluid. In some embodiments, the syringe is an Accurus® system syringe. In some embodiments, the system has one syringe. In some embodiments, the system has two syringes. In some embodiments, the system has three syringes. In some embodiments, the system has four or more syringes.

The system may further comprise an automated injection pump, which may be activated by, e.g., a foot pedal.

The fluids suitable for use in the methods of the invention include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

The fluids suitable for use in the methods of the invention include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

In some embodiments, the volume of the fluid comprising an effective amount of the vector is greater than about 0.8 ml. In some embodiments, the volume of the fluid comprising an effective amount of the vector is at least about 0.9 ml. In some embodiments, the volume of the fluid comprising an effective amount of the vector is at least about 1.0 ml. In some embodiments, the volume of the fluid comprising an effective amount of the vector is at least about 1.5 ml. In some embodiments, the volume of the fluid comprising an effective amount of the vector is at least about 2.0 ml. In some embodiments, the volume of the fluid comprising an effective amount of the vector is greater than about 0.8 to about 3.0 ml. In some embodiments, the volume of the fluid comprising an effective amount of the vector is greater than about 0.8 to about 2.5 ml. In some embodiments, the volume of the fluid comprising an effective amount of the vector is greater than about 0.8 to about 2.0 ml. In some embodiments, the volume of the fluid comprising an effective amount of the vector is greater than about 0.8 to about 1.5 ml. In some embodiments, the volume of the fluid comprising an effective amount of the vector is greater than about 0.8 to about 1.0 ml. In some embodiments, the volume of the fluid comprising an effective amount of the vector is about 0.9 to about 3.0 ml. In some embodiments, the volume of the fluid comprising an effective amount of the vector is about 0.9 to about 2.5 ml. In some embodiments, the volume of the fluid comprising an effective amount of the vector is about 0.9 to about 2.0 ml. In some embodiments, the volume of the fluid comprising an effective amount of the vector is about 0.9 to about 1.5 ml. In some embodiments, the volume of the fluid comprising an effective amount of the vector is about 0.9 to about 1.0 ml. In some embodiments, the volume of the fluid comprising an effective amount of the vector is about 1.0 to about 3.0 ml. In some embodiments, the volume of the fluid comprising an effective amount of the vector is about 1.0 to about 2.0 ml.

The fluid for creating the initial bleb may be, for example, about 0.1 to about 0.5 ml. In some embodiments, the total volume of all fluids in the system is about 0.5 to about 3.0 ml.

In some embodiments, the system comprises a single fluid (e.g., a fluid comprising an effective amount of the vector). In some embodiments, the system comprises 2 fluids. In some embodiments, the system comprises 3 fluids. In some embodiments, the system comprises 4 or more fluids.

The systems of the invention may further be packaged into kits, wherein the kits may further comprise instructions for use. In some embodiments, the kits further comprise a device for subretinal delivery of compositions of rAAV particles. In some embodiments, the instructions for use include instructions according to one of the methods described herein. In some embodiments, the instructions for use include instructions for subretinal delivery of rAAV particles comprising a capsid with one or more amino acid substitutions which alter, reduce or ablate binding of the rAAV particle to HSPG.

CNS Delivery

The present invention provides kits for delivering a heterologous nucleic acid to the CNS of an individual comprising a composition comprising rAAV particles, where the rAAV particle comprises (a) a rAAV capsid comprising rAAV capsid proteins comprising one or more amino acid substitutions at one or more positions that interacts with a heparan sulfate proteoglycan, and (b) a rAAV vector comprising the heterologous nucleic acid and at least one AAV inverted terminal repeat. Further provided herein are kits for treating a CNS disorder in an individual comprising a composition comprising rAAV particles, where the rAAV particle comprises (a) a rAAV capsid comprising rAAV capsid proteins comprising one or more amino acid substitutions at one or more positions that interacts with a heparan sulfate proteoglycan, and (b) a rAAV vector comprising the heterologous nucleic acid for treating a CNS disorder and at least one AAV inverted terminal repeat.

The kits may comprise any of the rAAV particles or rAAV particle compositions of the invention. For example, the kits may include rAAV particles with a rAAV capsid comprising rAAV capsid proteins comprising one or more amino acid substitutions at one or more positions that interact with a heparan sulfate proteoglycan (e.g., one or more amino acid substitutions that reduce binding of the rAAV particle to heparan sulfate proteoglycan, such as substitutions at R484, R487, K527, K532, R585 and/or R588, numbering based on VP1 of AAV2) and a rAAV vector comprising the heterologous nucleic acid and at least one AAV inverted terminal repeat.

In some embodiments, the kits further comprise a device for CNS delivery of the composition of rAAV particles. Devices for CNS delivery (e.g., for delivery of a composition including rAAV particles) are known in the art and may employ a pump (e.g., an osmotic and/or infusion pump, as described below) and an injection device (e.g., a catheter, cannula, etc.). Optionally, an imaging technique may be used to guide the injection device and/or monitor delivery of the infusate (e.g., a composition including rAAV particles). CNS delivery may include delivery by stereotaxic injection, or by convection enhanced delivery (CED). The injection device may be inserted into the CNS tissue in the subject. One of skill in the art is able to determined suitable coordinates for positioning the injection device in the target CNS tissue. In some embodiments, positioning is accomplished through an anatomical map obtained for example by CT and/or MRI imaging of the subject's brain to guide the injection device to the target CNS tissue.

In some embodiments, intraoperative magnetic resonance imaging (iMRI) and/or real-time imaging of the delivery may be performed. In some embodiments, the device is used to administer rAAV particles to a mammal by the methods of the invention. iMRI is known in the art as a technique for MRI-based imaging of a patient during surgery, which helps confirm a successful surgical procedure (e.g., to deliver rAAV particles to the CNS) and reduces the risk of damaging other parts of the tissue (for further descriptions, see, e.g., Fiandaca et al., (2009) Neuroimage 47 Suppl. 2:T27-35). In some embodiments, a tracing agent (e.g., an MRI contrast enhancing agent) may be co-delivered with the infusate (e.g., a composition including rAAV particles) to provide for real-time monitoring of tissue distribution of infusate. See for example Fiandaca et al., (2009) Neuroimage 47 Suppl. 2:T27-35; U.S. PG Pub 2007/0259031; and U.S. Pat. No. 7,922,999. Use of a tracing agent may inform the cessation of delivery. Other tracing and imaging means known in the art may also be used to follow infusate distribution.

In some embodiments, rAAV particles may be administered by standard stereotaxic (the term "stereotactic" may be used interchangeably herein) injection using devices and methods known in the art for delivery of rAAV particles. Generally, these methods may use an injection device, a planning system for translating a region of the tissue targeted for delivery into a series of coordinates (e.g., parameters along the latero-lateral, dorso-ventral, and rostro-caudal axes), and a device for stereotaxic localization according to the planned coordinates (e.g., a stereotaxic device, optionally including the probe and a structure for fixing the head in place in alignment with the coordinate system). A non-limiting example of a system that may be useful for MRI-guided surgery and/or stereotaxic injection is the ClearPoint® system (MM Interventions, Memphis, TN).

Another exemplary and non-limiting method for delivering a rAAV particle to the CNS is convection enhanced delivery (CED). As used herein, the term "convection enhanced delivery (CED)" may refer to delivery of a therapeutic agent to the CNS by infusion at a rate in which hydrostatic pressure leads to convective distribution. In some embodiments, the infusion is done at a rate greater than 0.5 µL/min. However, any suitable flow rate can be used such that the intracranial pressure is maintained at suitable levels so as not to injure the brain tissue. CED may be accomplished, for example, by using a suitable catheter or cannula (e.g., a step-design reflux-free cannula) through positioning the tip of the cannula at least in close proximity to the target CNS tissue (for example, the tip is inserted into the CNS tissue). After the cannula is positioned, it is connected to a pump which delivers the therapeutic agent through the cannula tip to the target CNS tissue. A pressure gradient from the tip of the cannula may be maintained during infusion. In some embodiments, infusion may be monitored by a tracing agent detectable by an imaging method such as intraoperative MRI (iMRI) or another real-time Mill technique.

CED is based on pumping an infusate (e.g., a composition containing a rAAV particle) into the CNS under pressure in which the hydrostatic pressure of the interstitial fluid is overcome. This brings the infusate into contact with the CNS perivasculature, which is utilized like a pump to distribute the infusate through convection and enhance the extent of its delivery (see, e.g., Hadaczek et al., (2006) Hum. Gene Ther. 17:291-302; Bankiewicz et al., (2000) Exp.

Neurol. 164:2-14; Sanftner, L M et al., (2005) *Exp. Neurol.* 194(2):476-483; Forsayeth, J R et al., (2006) *Mol. Ther.* 14(4):571-577; U.S. Pat. No. 6,953,575; U.S. Pat. App. Pub. No. 2002/0141980; U.S. Pat. App. Pub. No. 2007/0259031; and WO 2010/088560).

In some embodiments, a device for convection enhanced delivery comprises an osmotic pump and/or an infusion pump. Osmotic and/or infusion pumps are commercially available (e.g., from ALZET® Corp., Hamilton Corp., ALZA Inc. in Palo Alto, CA). Pump systems may be implantable. Exemplary pump systems may be found, e.g., in U.S. Pat. Nos. 7,351,239; 7,341,577; 6,042,579; 5,735,815; and 4,692,147. Exemplary devices for CED, including reflux-resistant and stepped cannulae, may be found in WO 99/61066 and WO 2006/042090, which are hereby incorporated by reference in their entirety.

In some embodiments, the device for convection enhanced delivery comprises a reflux-resistant cannula (e.g., a reflux-free step design cannula). Further descriptions and exemplary reflux-resistant cannulae may be found, for example, in Krauze et al., (2009) *Methods Enzymol.* 465: 349-362; U.S. PG Pub 2006/0135945; C, S. PG Pub 2007/0088295; and PCT/US08/64011. In some embodiments, only one cannula is used. In other embodiments, more than one cannula is used. In some embodiments, the device for convection enhanced delivery comprises a reflux-resistant cannula joined with a pump that produces enough pressure to cause the infusate to flow through the cannula to the target tissue at controlled rates. Any suitable flow rate can be used such that the intracranial pressure is maintained at suitable levels so as not to injure the brain tissue.

In some embodiments, penetration of the infusate is further augmented by the use of a facilitating agent. A facilitating agent is capable of further facilitating the delivery of infusate to target tissue (e.g., CNS target tissue). A non-limiting example of a facilitating agent is low molecular weight heparin (see, e.g., U.S. Pat. No. 7,922,999).

In some embodiments, the kits further include instructions for CNS delivery of the composition of rAAV particles. The kits described herein may further include other materials desirable from a commercial and user standpoint, including other buffers, diluents, filters, needles, syringes, and package inserts with instructions for performing any methods described herein. Suitable packaging materials may also be included and may be any packaging materials known in the art, including, for example, vials (such as sealed vials), vessels, ampules, bottles, jars, flexible packaging (e.g., sealed Mylar or plastic bags), and the like. These articles of manufacture may further be sterilized and/or sealed. In some embodiments, the kits comprise instructions for treating a disorder of the CNS described herein using any of the methods and/or rAAV particles described herein. The kits may include a pharmaceutically acceptable carrier suitable for injection into the CNS of an individual, and one or more of: a buffer, a diluent, a filter, a needle, a syringe, and a package insert with instructions for performing injections into the CNS of an individual.

Excipients

In some embodiments related to subretinal and/or CNS delivery, the kits further contain buffers and/or pharmaceutically acceptable excipients. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

In some embodiments related to subretinal and/or CNS delivery, pharmaceutically acceptable excipients may include pharmaceutically acceptable carriers. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Additional ingredients may also be used, for example preservatives, buffers, tonicity agents, antioxidants and stabilizers, nonionic wetting or clarifying agents, viscosity-increasing agents, and the like. The kits described herein can be packaged in single unit dosages or in multidosage forms. The contents of the kits are generally formulated as sterile and substantially isotonic solution.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Mutations in Arginine Residues Required for HSPG Binding Decrease AAV2-Mediated Transduction in Cultured Cell Lines AAV2 gene therapy vectors are currently being used in clinical trials for ocular indications. These vectors can be delivered via an intravitreal route of administration, which in mice and non-human primates results in transduction of retinal ganglion cells and Müller cells, or by a subretinal route of administration, which targets the retinal pigmented epithelial cells and photoreceptor cells. Different serotypes of AAV use different cell surface receptors and co-receptors for infection. It is known that the primary cell surface receptor for AAV2 is heparan sulfate proteoglycan (HSPG) (Summerford, C. and Samulski, R. J. (1998) *J. Virol.* 72(2): 1438-45). Understanding the mechanism whereby AAV2 transduces the retina is important for further development of AAV gene therapy vectors.

To investigate the role of HSPG binding in AAV2 transduction of the retina, AAV2 vectors were generated with capsid proteins bearing mutations in arginine residues known to be required for HSPG binding (AAV2 HBKO). These vectors resulted in significantly reduced transduction of 293 and HeLa cells in culture, compared to wild-type AAV2. Surprisingly, AAV2HBKO vector delivered subretinally to the mouse eye resulted in a 2-log increase in transduction compared to wild-type AAV2. However, when the AAV2HBKO vector was delivered intravitreally, no transduction was evident. These results indicate that mutations in amino acids required for HSPG binding have opposite effects on transduction efficiency following subretinal versus intravitreal injection of AAV2 particles.

Methods

Construction of AAV2 Arginine Mutant Plasmid

The AAV2 rep/cap plasmid, pIM45BD, was mutated using the Quikchange Lightning Multi Site Directed Mutagenesis Kit (Agilent Technologies). A PCR mutagenesis primer was designed to introduce changes of arginines 585 and 588 to alanines. Positive mutants were confirmed by sequencing.

Generation of rAAV Vectors

Recombinant AAV vectors expressing either enhanced green fluorescent protein (EGFP) or soluble VEGF receptor hybrid (sFLT02) were produced by triple transfection of 293 cells using the pIM45BD or pIM45BDR585A/R588A rep/cap plasmid and pAdHelper. Transgenes were under the control of either the chicken β-actin (CBA) or human rhodopsin kinase promoters (RK).

In vitro Transduction Assays 293 or HeLa cells were plated into 24 well plates ($1-2\times10^5$ cells per well). 24 hours after plating, the cells were infected with $1\times10^3$ vg/cell (+) Ad5ts149. Transduction efficiency was measured 48 hours post infection either by EGFP fluorescence or by ELISA to quantify sFLT02 in the media (human soluble VEGF R1 ELISA by R&D Systems).

Animals

Adult C57BL/6 mice obtained from Jackson Laboratories (Bar Harbor, ME) were purchased and maintained at Genzyme's vivarium. The animals were given free access to food and water for the duration of the study. All procedures were performed under a protocol approved by the Institutional Animal Care and Use Committee.

Intravitreal Injection

Torpor was induced and maintained using 3.5 isoflurane carried in 800 mL/minute of oxygen delivered to the animal via a nose cone. One microliter of test article was injected into the vitreous humor using a Hamilton syringe fitted with a 33 gauge beveled needle (Hamilton Co., Reno, NV). The needle was directed through the sclera approximately 2 mm below the limbus and carefully advanced into the vitreal chamber to avoid contact with the lens. The test article was delivered over a 1-2 second period. Following the injection, the needle was held in position for approximately five seconds before withdrawal. The animal was allowed to recover from anesthesia prior to returning to its cage.

Subretinal Injection

Mydriasis and cycloplegia was induced with a topical application of Tropicamide (Alcon, Fort Worth, TX). Torpor was induced and maintained using 3.5% isoflurane carried in 800 mL/minute of oxygen delivered to the animal via a nose cone. The eye was immobilized using ring tipped forceps (World Precision Instruments, Sarasota, FL) and a pilot incision was placed approximately 2 mm below the limbus on in the sclera using a 30 gauge needle. A 33 gauge blunt tipped needle was directed through the incision and advanced posteriorly until the tip penetrated the posterior neurosensory retina. One microliter of test article was delivered over one second. The needle was held in position for approximately five seconds before withdrawal. The animal was allowed to recover from anesthesia prior to returning to its cage.

Histology for EGFP

Raw EGFP signal was observed using an epifluorescence microscope on formalin fixed eyes processed for paraffin embedding.

Results

As depicted in FIG. 1, five capsid residues have been shown to be critical for AAV2 binding to HSPG. An AAV2 mutant was constructed bearing two amino acid substitutions in these residues: R585A and R588A (numbering is based on VP1 amino acid sequence). This mutant, referred to as HBKO, was tested for its ability to transduce cells in culture.

Human cell lines were grown in culture and transduced with wild-type or HBKO mutant AAV2 particles. To measure transduction efficiency, the viral genomes of both types of AAV2 particles were modified to include transgenes using the ubiquitous CBA promoter to drive expression of soluble Flt (human VEGF receptor 1). 48 hours after transduction, transduction efficiency was measured using an ELISA-based immunoassay to quantify the amount of Flt produced. FIG. 2 demonstrates that the HBKO mutant showed a greatly reduced ability to transduce human 293 cells in culture. Using equal numbers of AAV2 particles and 293 cells, the HBKO mutant showed a 99.6% reduction in transduction efficiency compared to wild-type.

Figure 3:
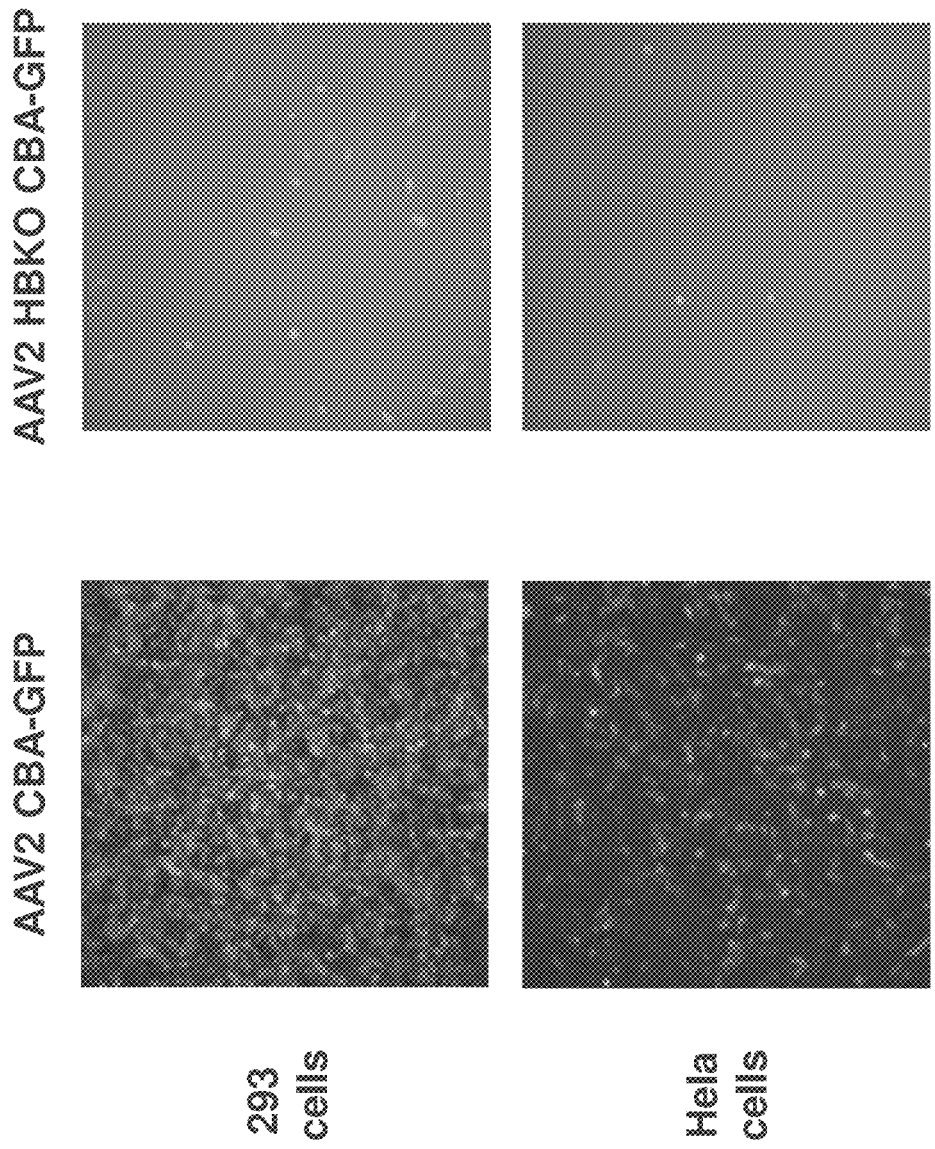
FIG. 3 shows the decrease in transduction of 293 and Hela cells in culture observed with HBKO mutant AAV2 particles (AAV2 HBKO CBA-GFP), as compared to wild-type AAV2 particles (AAV2 CBA-GFP). Transduction was assayed by fluorescence imaging of cells taken 48 hours after injection with wild-type or HBKO mutant AAV2 particles bearing vectors that use the CBA promoter to drive expression of EGFP.

To measure this effect in multiple human cell lines, 293 and Hela cells were transduced as described above. For these assays, the vectors were modified to express EGFP, rather than Flt, from the CBA promoter. FIG. 3 shows that wild-type AAV2 was able to transduce both cell lines, as measured by EGFP fluorescence. In contrast, the HBKO mutant had a dramatic decrease in transduction of both cell lines. These results confirm that the HBKO mutant has a dramatically reduced ability to transduce human embryonic kidney and cervical cancer cell lines in culture.

Figure 4:
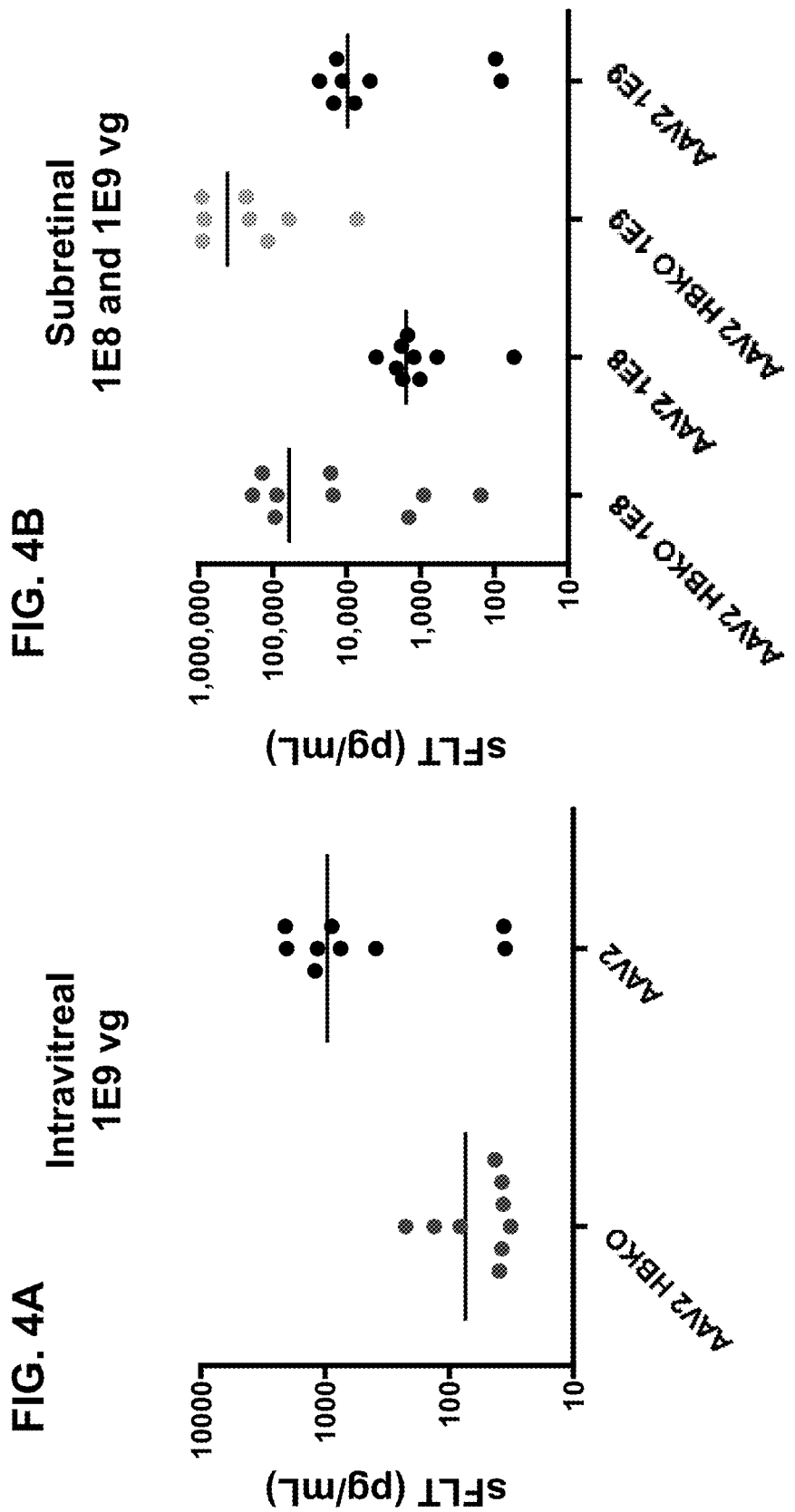
FIGS. 4A & 4B show the transduction observed upon intravitreal (FIG. 4A) or subretinal (FIG. 4B) injection of wild-type AAV2 or HBKO mutant AAV2 particles. Transduction was assayed by expression of soluble Flt (sFLT) after transduction with vectors encoding Flt. The number of vector genomes injected is indicated for each experiment ($10^8$ or $10^9$ vg).

Example 2: Mutations in Arginine Residues Required for HSPG Binding have Opposite Effects on AAV2-Mediated Transduction Following Intravitreal Versus Subretinal Injection The ability of HBKO mutant AAV2 particles to transduce ocular cells upon intravitreal and subretinal injection was tested in the mouse. FIGS. 4A & 4B compare the transduction efficiency of wild-type and HBKO AAV2 particles upon intravitreal or subretinal injection. For these experiments, transduction efficiency was assayed by measuring soluble Flt (sFLT) expression upon transduction with AAV2 particles bearing a transgene that uses the ubiquitous CBA promoter to drive expression of Flt. Using intravitreal injection, the HBKO mutant showed a greatly reduced ability to transduce cells (FIG. 4A).

Surprisingly, the HBKO mutant showed enhanced transduction after subretinal injection (FIG. 4B). This increase was consistently observed when the amount of AAV2 vector genomes injected was varied 10-fold ($10^8$ and $10^9$ vg, as labeled). These results contrast with those observed in cultured cell lines and upon intravitreal injection. These data point to the importance of HSPG binding ability in mediating transduction of different ocular cell types and retinal layers by different types of intraocular injections.

To visualize the transduction of retinal cells, wild-type or HBKO mutant AAV2 particles bearing a transgene expressing EGFP from the ubiquitous CBA promoter were used. As shown in FIG. 5, wild-type AAV2 particles were able to transduce the retina following intravitreal injection, as demonstrated by GFP fluorescence. However, AAV2 HBKO mutant particles showed no detectable GFP fluorescence upon intravitreal injection. These results are in agreement with those presented in FIG. 4A.

Figure 6:
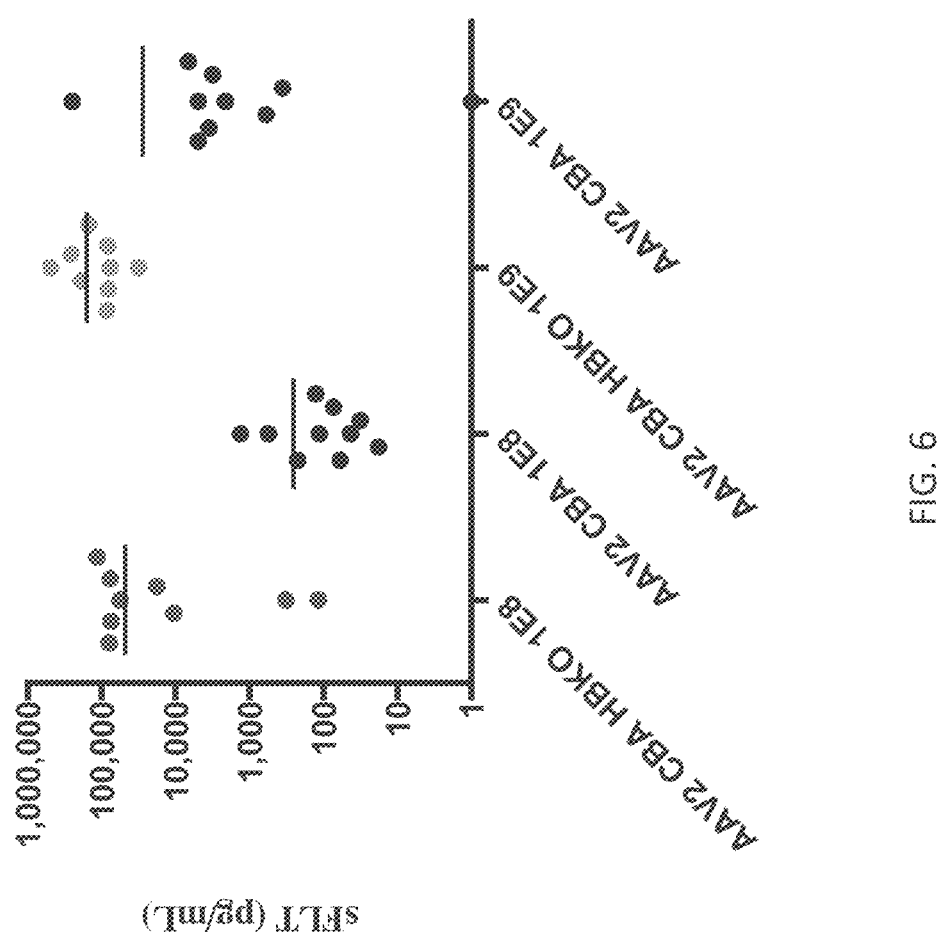
FIG. 6 shows that HBKO mutant AAV2 particles (AAV2 CBA HBKO) cause a significant increase in transduction following subretinal injection, as compared to wild-type particles (AAV2 CBA). Transduction was assayed by expression of soluble Flt (sFLT) after injection with AAV2 particles bearing vectors that use the CBA promoter to drive expression of Flt. The number of vector genomes injected is indicated ($10^8$ or $10^9$ vg).

FIG. 6 quantified the transduction efficiency of wild-type (AAV2 CBA) and HBKO mutant (AAV2 CBA HBKO) AAV2 particles upon subretinal injection. To measure transduction, both AAV2 particles had vector genomes including a transgene expressing Flt using the ubiquitous CBA promoter. Two amounts of vector genomes were used for the injections, as indicated in FIG. 6. These results confirm the observation shown in FIG. 4B and demonstrate the surprising finding that mutating residues required for HSPG binding increases the ability of AAV2 to transduce cells after subretinal injection.

Figure 7:
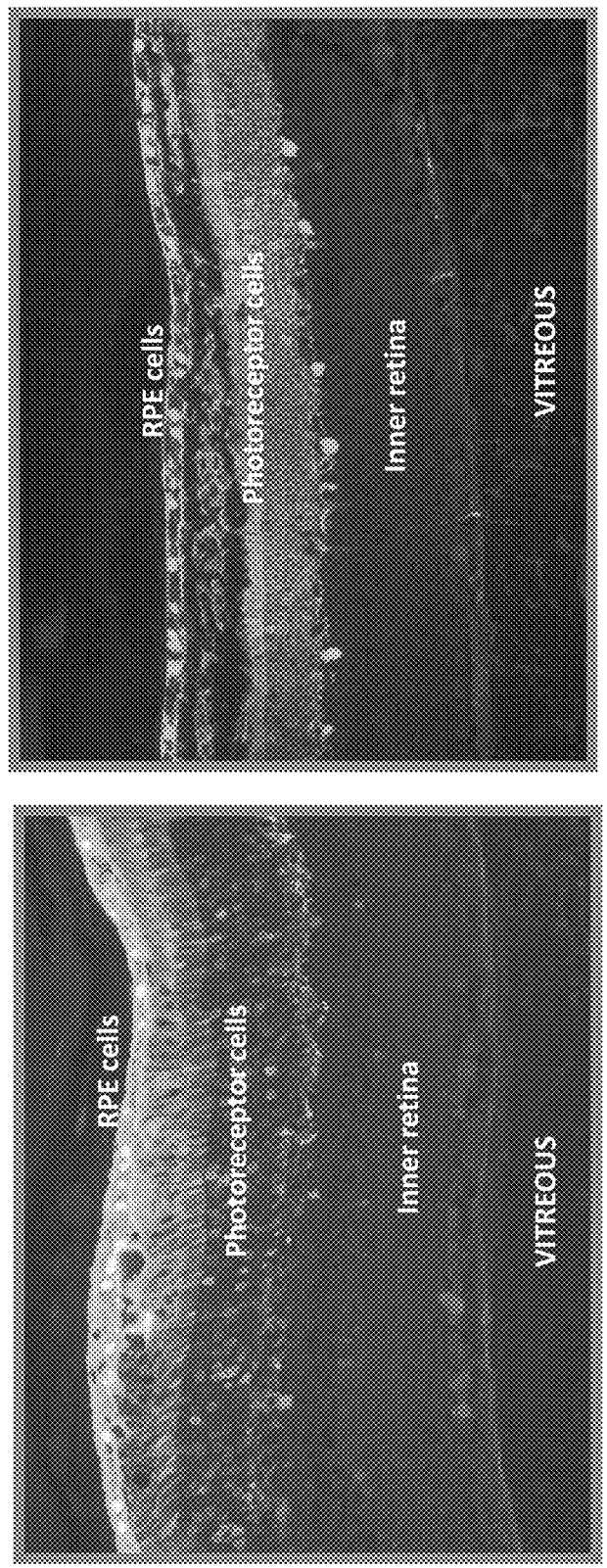
FIG. 7 shows that HBKO mutant AAV2 particles (AAV2 HBKO CBA-GFP) cause a significant increase in transduction of photoreceptor cells (as labeled) following subretinal injection, as compared to wild-type particles (AAV2 CBA-GFP). Transduction was measured by fluorescence imaging of GFP expression following transduction with AAV2 particles bearing vectors that use the CBA promoter to drive expression of EGFP.

To visualize transduction, wild-type or HBKO mutant AAV2 particles bearing a transgene expressing EGFP from the ubiquitous CBA promoter were used. As shown in FIG. 7, GFP fluorescence in the retina is enhanced upon transduction with HBKO mutant AAV2 particles, as compared to wild-type.

Figure 8:
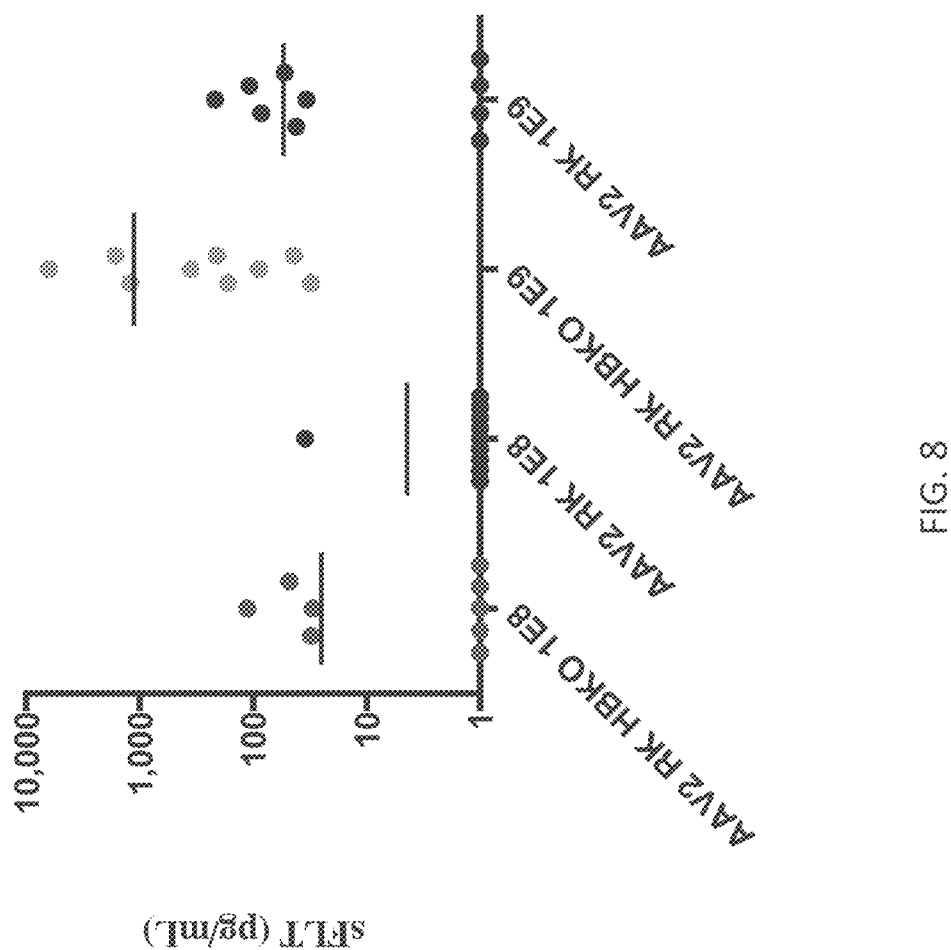
FIG. 8 shows that HBKO mutant AAV2 particles (AAV2 RK HBKO) cause a significant increase in transduction of photoreceptors following subretinal injection, as compared to wild-type particles (AAV2 RK). Transduction was assayed by expression of soluble Flt (sFLT) after injection with AAV2 particles bearing vectors that use the rhodopsin kinase (RK) promoter to drive expression of Flt. Number of vector genomes injected is indicated ($10^8$ or $10^9$ vg).

Because subretinal injection is known to target cell layers with photoreceptor cells, the ability of HBKO mutant AAV2 particles to transduce photoreceptors was studied. In the eye, the rhodopsin kinase (RK) promoter is known to drive expression specifically in photoreceptor cells, such as the rod and cone cells (Khani, S. C., et al. (2007) *Invest. Ophthalmol. Vis. Sci.* 48(9):3954-61). Therefore, wild-type and HBKO mutant AAV2 particles were generated with vector genomes bearing a transgene using the RK promoter to drive expression of Flt. As shown in FIG. 8, HBKO mutant AAV2 particles showed enhanced transduction of photoreceptor cells following subretinal injection, as compared to wild-type. This observation was consistently observed upon injection with 10-fold different amounts of vector genomes ($10^8$ and $10^9$ vg, as labeled). These results demonstrate the surprising result that mutating the residues required for HSPG binding enhances the ability of AAV2 particles to transduce retinal photoreceptor cells following subretinal injection. Mutation of these residues represents a potential way to enhance transduction of photoreceptor cells for AAV2-mediated gene therapy.

AAV is a single-stranded, non-enveloped DNA virus that is a member of the parvovirus family. Different serotypes of AAV including AAV1, AAV2, AAV4, AAV5, AAV6, etc demonstrate different profiles of tissue distribution. The diverse tissue tropisms of these AAV capsids have enabled AAV based vectors to be used for widespread gene transfer applications both in vitro and in vivo for liver, skeletal muscle, brain, retina, heart and spinal cord (Wu, Z., et al., (2006) *Molecular Therapy*, 14: 316-327). Attachment of a virus to a host cell requires specific interactions of the virus capsid with cellular receptor molecules. AAV2 capsid has been previously shown to use heparan sulfate proteoglycan (HSPG), V 5 integrin and human fibroblast growth factor receptor 1 as primary and secondary receptors to mediate cell entry of AAV2 based gene therapy vectors (Summerford, C. and R. J. Samulski (1998) *J. Virology*, 72: 1438-1445; Summerford, C. et al., (1999) *Nat. Medicine*, 5: 78-82; Qing, K., et al., (1999) *Nat. Medicine*, 5: 71-77). Mutational analysis of AAV2 capsid proteins has shown that a group of basic amino acids namely arginines R484, R487, R585, R588 and lysine K532 contribute to heparan binding and in vitro transduction of cells and in vivo liver transduction of AAV2 vectors. Mutations in these amino acid residues led to greatly decreased liver transduction of AAV2 based vectors by the intravenous route of administration and increased cardiac and skeletal muscle gene transfer (Kern, A. et al., (2003) *J. Virology*, 77: 11072-11081; Müller, O. J. et al., (2006) *Cardiovascular Research*, 70: 70-78).

The role of these basic amino acids was investigated on transduction of AAV2 vectors in the retina both by the intravitreal route and the subretinal route of vector administration. Mutation of R585 and R588 significantly eliminated in vitro transduction of HEK293 cells and Hela cells (FIGS. 2 and 3). Dalkara D et al., ((2009) *Molecular Therapy*, 17: 2096-2102) suggest that intravitreally delivered AAV2 vectors fail to penetrate into the outer retina because of binding to heparan sulfate proteoglycans which are abundant in the inner limiting membrane of the retina. As shown by the present examples, upon intravitreal delivery the R585/R588 mutated vectors are less capable of transduction of the inner retina compared to the wild type AAV2 vectors (FIGS. 4A and 5) suggesting that the binding to HSPG is important for intravitreal transduction of the retina. Subretinal delivery of AAV2 based vectors leads to predominantly retinal pigmented epithelium (RPE) transduction and some photoreceptor cell transduction. Surprisingly, it was found that the R585/R588 mutated vectors transduce the outer retina at least 10 times better than wild type AAV2 vectors (FIGS. 4B, 6, and 7). Using the photoreceptor-specific rhodopsin kinase promoter (RK), transgene expression in photoreceptors is significantly increased with the AAV2 R585/R588 mutant vector (FIG. 8). These vectors based on mutations in the basic amino acid residues on the AAV2 capsid will be highly beneficial for transduction of the outer retina especially the photoreceptor cells for the treatment of a variety of retinal disorders.

Example 3: Widespread GFP Expression after Intrastriatal AAV2HBKO Vector Delivery Through site-directed mutations introduced to the AAV2 capsid, an AAV2 HBKO mutant vector was generated that is unable to bind heparin. The transduction profile of this HBKO vector was evaluated in both wild-type mice and a HD mouse model (YAC128) using single intrastriatal injections.

Methods

Construction of AAV2 Arginine Mutant Plasmid

The AAV2 rep/cap plasmid, pIM45BD, was mutated using the Quikchange Lightning Multi Site Directed Mutagenesis Kit (Agilent Technologies). A PCR mutagenesis primer was designed to introduce changes of arginine to alanine at residues 585 and 588. Positive mutants were confirmed by sequencing.

Production of AAV Vectors

Recombinant AAV vectors were produced by triple transfection (using calcium phosphate) of human embryonic kidney carcinoma 293 cells (HEK-293) as previously described (Xiao et al. (1998) *J. Virol.* 72:2224-2232). Briefly, a plasmid containing the rep gene from serotype 2 and a capsid gene from either serotype 1, or 2 along with a helper adenoviral plasmid (Stratagene, Palo Alto, CA) was used. Transgenes were under the control of the chicken beta-actin (CBA) promoter. Virus was collected 72 hours post-transfection and column purified as previously described (Xiao et al. (1998) *J. Virol.* 72:2224-2232).

Animals

All procedures were performed using a protocol approved by the Institutional Animal Care and Use Committee at Genzyme, a Sanofi Company (Department of Health and Human Services, NIH Publication 86-23). Mice used included YAC128 mice (a yeast artificial chromosome harboring the full-length human mutant HTT transgene with 128 CAG repeats on a pure FVB/NJ background) and wild type FVB/NJ littermate mice (Slow et al. (2003) *Hum. Mol. Genet.* 12:1555-1567; Van Raamsdonk et al. (2005) *Hum. Mol. Genet.* 14:3823-3835). Both the YAC128 mice and FVB/NJ littermates were obtained from a Genzyme colony that was housed at the Charles River Laboratories. The mice were maintained on a 12 h light/dark cycle with food and water available ad libitum. All behavioral testing was performed during the animals' light cycle (between the hours of 8 am and 4 pm). N-values for all experiments are shown in Tables 2 and 3 below.

TABLE 2

Wild-type mice treated with AAV particles expressing GFP (Experiment 1).

| Treatment | n-value (WT mice) | Dose (DRPs) |
| --- | --- | --- |
| AAV2HBKO-CBA-GFP | 6 | $6 \times 10^9$ |
| AAV2-CBA-GFP | 6 | $6 \times 10^9$ |

TABLE 3

YAC128 mice treated with AAV particles expressing Htt miRNA and GFP (Experiment 2).

| Treatment | n-value (YAC128 mice) | Dose (DRPs) |
| --- | --- | --- |
| AAV2HBKO-CBA-miRNA-Htt-GFP | 8 | $6 \times 10^9$ |
| AAV1-CBA-miRNA-Htt-GFP | 8 | $1.5 \times 10^{10}$ |
| Untreated | 8 | N/A |

Surgical Procedures

Animals were anesthetized using 3% isofluorane and placed into a stereotaxic frame. Intracranial injections were performed as previously described (Stanek et al. (2014) *Hum. Gene Ther.* 25:461-474). Briefly, 3 µl of the recombinant viral vectors were injected into the striatum (AP, +0.50; ML, ±2.00; DV, −2.5 from bregma and dura; incisor bar, 0.0) using a 10 µl Hamilton syringe at the rate of 0.5 µl/min. The needle was left in place for 1 min following the completion of infusion. One hour before surgery and for 24 h following surgery, the mice were administered ketoprofen (5 mg/kg) subcutaneously for analgesia.

Animal Perfusion and Tissue Collection

The mice were perfused through the heart with phosphate-buffered saline (PBS) to remove all blood. For experiment 1, the brains were cut along the coronal plane, post-fixed in 4% paraformaldehyde followed by 30% sucrose. 20-µm coronal sections were cut using a cryostat. For experiment 2, brains were cut sagittally along the midline, and the left hemisphere was post-fixed in 4% paraformaldehyde followed by 30% sucrose and then sectioned into 20-µm sections using a cryostat. The right hemisphere (used for biochemical assays) was cut along the coronal axis using a mouse brain matrix (Harvard Apparatus, Holliston, MA), and striatal and cortical regions were dissected using a 3 mm biopsy punch. Brain tissue was then flash-frozen in liquid nitrogen and stored at −80° C. until use.

Quantitative Real-Time PCR (TaqMan)

RNA levels were measured by quantitative real-time RT-PCR. Striatal punches were used for all RT-PCR analysis. Total RNA was extracted using the QIAGEN RNEasy mini kit and then reverse transcribed and amplified using the TaqMan® One-Step RT-PCR Master Mix Kit (Applied Biosystems) according to the manufacturer's instructions. TaqMan quantitative RT-PCR reactions were conducted and analyzed on an ABI PRISM® 7500 Real Time PCR System (Applied Biosystems). The expression levels of HTT mRNA were normalized to hypoxanthine guanine phosphoribosyl transferase 1 (HPRT1) mRNA levels. Standard curves were generated using 5-fold serial dilutions of mouse brain cDNA. Each sample was run in duplicate. The relative gene expression was determined by using the standard curve or AACT method and normalizing to HPRT1 mRNA levels. For detection of human HTT, the following primers were used: 5' CTCCGTCCGGTAGACATGCT 3' and 5' CCATTTTGAGGGTTCTGATTTCC 3'. For detection of mouse HTT, the following primers were used: 5' TGCTACACCTGACAGCGAGTCT 3' and 5' ATCCCTTGCGGATCCTATCA 3'.

Western Blotting

Protein levels were measured by western blot analysis. Cortical punches were used for all western blot analysis. Tissues, at a final concentration of 50 mg/ml in T-Per lysis buffer (Pierce) and containing the complete protease inhibitor cocktail (Roche), were homogenized. The homogenates were cleared by centrifugation at 10,000×g for 6 min at 4° C. The protein concentration was measured by using BSA assay (Pierce). Twenty to thirty micrograms of the homogenates was resolved on a 3-8% Novex tris-acetate gel and then transferred to a nitrocellulose membrane. The membranes were probed with a mouse anti-huntingtin monoclonal antibody (Mab2166; 1:2,000 dilution, Millipore) and rabbit polyclonal anti-β-tubulin antibody (1:750 dilution, Santa Cruz Biotechnology). The membranes were then incubated with infrared secondary antibodies (1:20,000 dilution, Rockland), and the proteins were visualized by quantitative fluorescence using Odyssey (LI-COR Biosciences). To control for loading variances, Htt protein was normalized to β-tubulin and expressed as a percentage of untreated or saline-treated animals. Molecular weight markers were used to verify the identity of the proteins.

Immunohistochemistry

Frozen brain sections were stained with either rabbit anti-GFAP antibody to stain astrocytes (1:2,500; DAKO, Glostrup, Germany) or anti-Iba1 antibody to visualize microglia (1:500; WAKO Chemicals USA, Richmond, VA). Secondary antibodies used were donkey anti-species—specific antibodies conjugated with FITC or Cy3. Sections were visualized using a Nikon Eclipse E800 fluorescent microscope (Nikon, Melville, NY).

Statistics

Mean values were used for statistical analyses. Data are expressed as the mean±SEM. For studies that used two groups, Student's t-test was used for statistical comparison. For comparisons of more than two groups, one-way ANOVA was used followed by Tukey's multiple comparison post-hoc test (Prism GraphPad). $p<0.05$ was considered as a statistically significant difference.

Results

As described above, AAV2-eGFP and AAV2HBKO-GFP vectors were injected into wild-type mice in Experiment 1

Figure 9A:
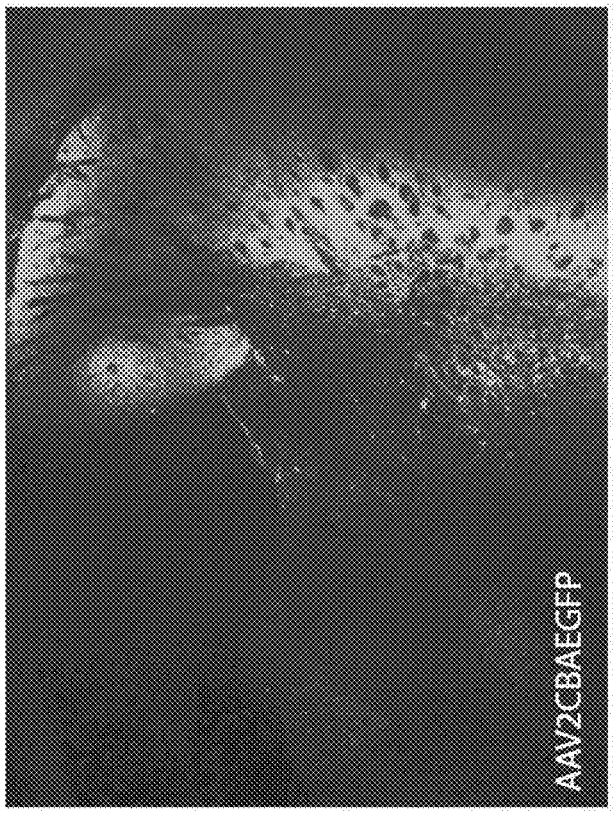
FIGS. 9A&9B show expression of EGFP in the mouse brain 30 days following intrastriatal injection of AAV2HBKO-EGFP (FIG. 9A), compared to AAV2-EGFP (FIG. 9B) in wild-type mice. In each panel, expression of EGFP was driven by the CBA promoter and visualized using fluorescence microscopy.
Figure 9B:
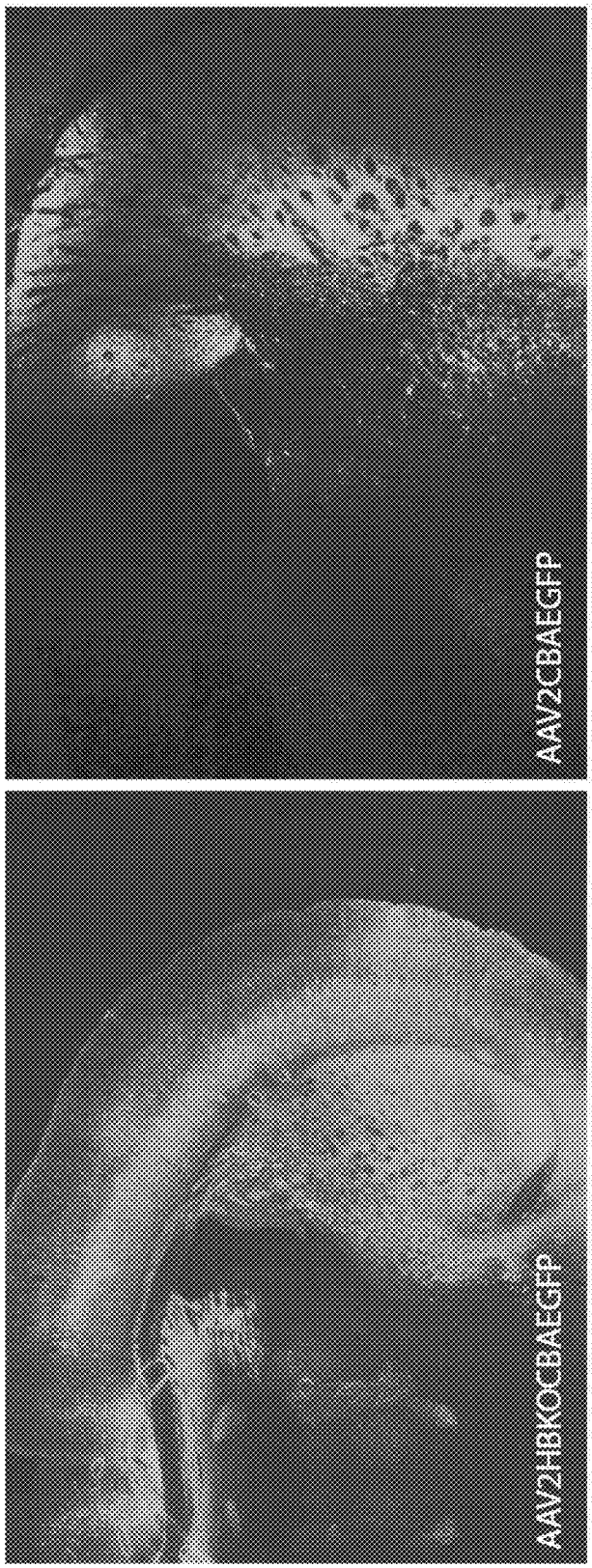

(Table 2). All animals were sacrificed 30 days following injection. Fluorescence microscopy revealed that both AAV2 and AAV2HBKO vectors drove expression of the GFP transgene in transduced neurons (FIGS. 9A&9B). GFP expression was limited to the injection track for AAV2, with minimal spread beyond the injection site (FIG. 9B). However, when compared with traditional AAV2, AAV2HBKO drove more robust and extensive GFP expression, with expression observed well beyond the injection site (FIG. 9A). These results demonstrate the robust and widespread expression of transgenes delivered to the CNS using an AAV2HBKO vector.

Example 4: Comparing AAV2HBKO- and AAV1-Mediated GFP Expression after Intrastriatal Injection into YAC128 Mouse Brains As described above, AAV2HBKO and AAV1 serotype vectors were injected into YAC128 mice in Experiment 2 (Table 3). These vectors drove expression of an artificial miRNA targeting human HTT and a GFP reporter. Both AAV1 and AAV2HBKO vectors showed robust GFP distribution 30 days following injection into the striatum (FIGS. 10A&10B). However, the pattern of GFP expression appeared markedly different between the two vector serotypes. AAV1 expression of GFP (FIG. 10A) was more patchy and less uniform than AAV2HBKO GFP expression (FIG. 10B). Vector transduction appeared to be exclusively neuronal in AAV2HBKO brains compared to the AAV1 serotypes which transduced both neurons and glial cells, primarily astrocytes. These results demonstrate that AAV2HBKO showed a very different expression and transduction profile when compared to traditional AAV1.

Figure 11A:
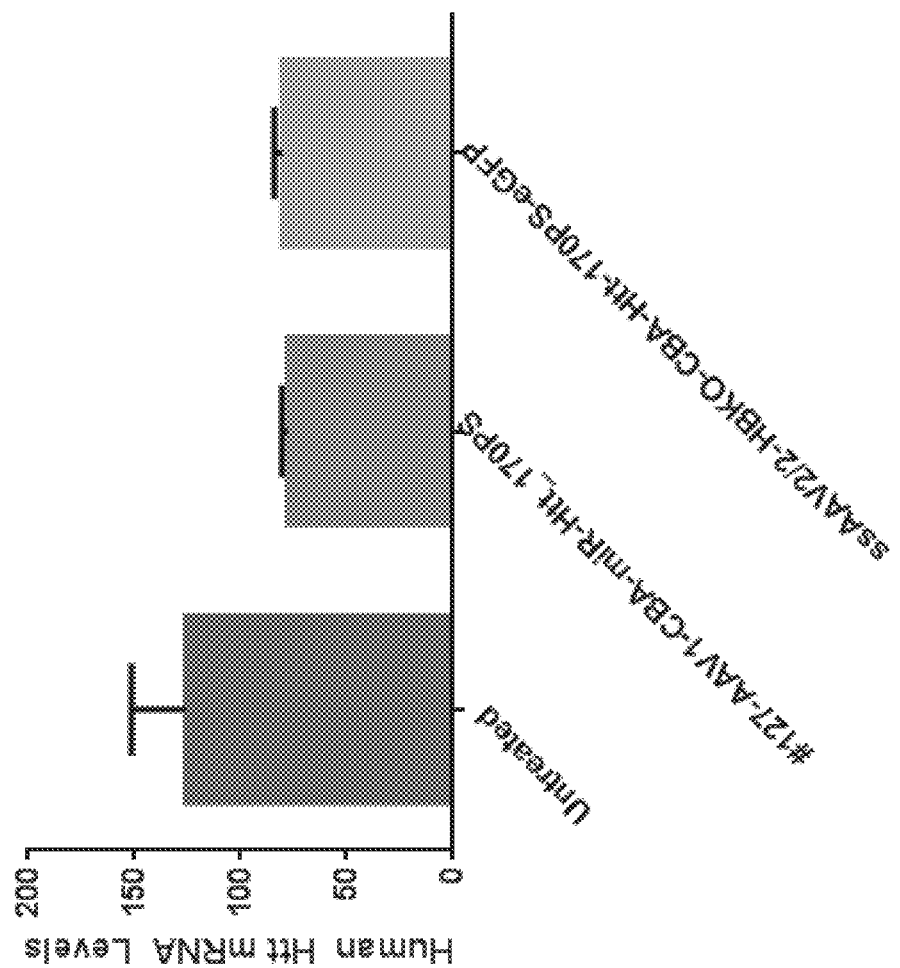
FIG. 11A shows qPCR analysis of human HTT mRNA levels in striatal mouse brain punches 30 days post injection of AAV1-miRNA-Htt and AAV2HBKO-miRNA-Htt, as compared to untreated controls.
Figure 11B:
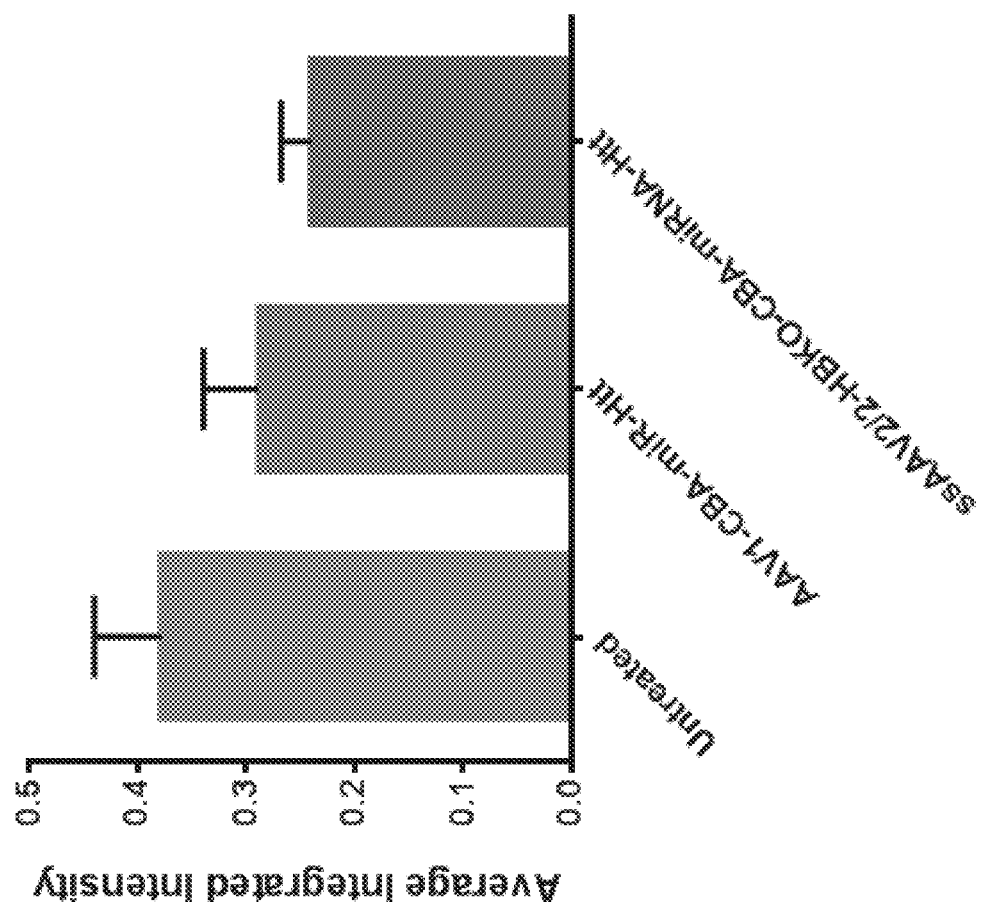
FIG. 11B shows Western blot analysis of human Htt protein levels in cortical mouse brain punches 30 days post injection of AAV1-miRNA-Htt and AAV2HBKO-miRNA-Htt, as compared to untreated controls.

Example 5: AAV2HBKO-miRNA-Htt Injection into YAC128 Mice Results in Reduction of HTT mRNA Next, the ability of AAV1 and AAV2HBKO vector serotypes to express a miRNA silencing HTT expression in the striatum of YAC128 mice was evaluated. Adult YAC128 mice received bilateral intrastriatal injections of AAV2/1-miRNA-Htt or the AAV2HBKO-miRNA-Htt, and brains were analyzed 30 days post-treatment. The striatal levels of mutant human HTT mRNA was significantly reduced in mice injected with AAV2/1-miRNA-Htt and AAV2HBKO-miRNA-Htt when compared untreated controls (FIG. 11A). Western blot analysis of cortical brain punches showed a trend toward Htt reduction in both treatment groups; however, variability in the untreated control samples prevented the data from reaching statistical significance (FIG. 11B). These results demonstrate the efficacy of gene knockdown by RNAi using AAV1 and AAV2HBKO vectors.

Example 6: AAV2HBKO-miRNAHtt Injection into YAC128 Mice does not Cause Neuroinflammation To determine whether injections of AAV conferred neuroinflammation, levels of the neuroinflammatory markers glial fibrillary acidic protein (GFAP, a marker of astrocytes) and Iba1 (a marker of microglia) were examined at 30 days post-treatment. No notable increases in Iba1 levels were observed following AAV2HKO treatment, compared to untreated brains (cf. FIGS. 12A and 12B). AAV2/1 treatment however did cause an increase in Iba1 levels at the injection site (FIG. 12C) that has been previously observed. No notable increases in GFAP levels were observed in any of the treated brains 30 days post injection compared to untreated controls (FIGS. 13A-13C). These results indicate that AAV2HBKO was able to drive the expression of a miRNA directed towards human HTT and generate HTT reduction in the absence of microglial activation, when compared with the AAV1 serotype.

CONCLUSIONS

Current AAV vector serotypes show limited distribution in the brain following single site administration (e.g., Christine, C. W. et al. (2009) *Neurology* 73:1662-1669; Mandel, R. J. (2010) *Curr. Opin. Mol. Ther.* 12:240-247). As discussed in detail herein, the inventors have discovered that administration AAV vectors having reduced binding to heparan-sulfate proteoglycans (HSPG) on cell surfaces enhances AAV transduction in the CNS. These results demonstrate the utility of AAV having modified HSPG binding for CNS gene therapy where widespread vector distribution is desired. Moreover, the inventors have also discovered that AAV2 vectors having reduced HSPG binding exhibit an ideal safety profile (as they exclusively target neurons), while achieving a widespread and robust transduction efficiency. Such vectors are therefore useful for CNS indications that require widespread neuronal transduction from an intraparenchymal delivery.

Example 7: In Vitro and Subretinal Transduction by AAVrh8R and AAVrh8R Mutant Vectors Methods Construction of AAVrh8R Arginine Modified Plasmids
The AAVrh8R rep/cap plasmid was mutated using the Quikchange Lightning Multi Site Directed Mutagenesis Kit (Agilent Technologies). A PCR mutagenesis primer was designed to introduce changes of alanine 586 to an arginine (AAVrh8R-A586R) or arginine 533 to an alanine (AAVrh8R-R533A). Positive mutants were confirmed by sequencing.
Generation of rAAV Vectors
Recombinant AAV vectors expressing either enhanced green fluorescent protein (EGFP) or soluble VEGF receptor hybrid (sFLT02) were produced by triple transfection of 293 cells using the pAAVrh8R, pAAVrh8R-A586R or pAAVrh8R-R533A rep/cap plasmids and pAdHelper. Transgenes were under the control of the chicken β-actin (CBA) promoter.
In Vitro Transduction Assays
HeLa, HeLaRC32 or NS1 cells were plated into 24 well plates ($1-2 \times 10^5$ cells per well). 24 hours after plating, the cells were infected with $1 \times 10^4$ vg/cell-$1 \times 10^5$ vg/cell (+) Ad5ts149. Transduction efficiency was measured 48 hours post-infection either by EGFP fluorescence or by ELISA to quantify sFLT02 in the media (human soluble VEGF R1 ELISA by R&D Systems).
Animals.
Adult C57BL/6 mice obtained from Jackson Laboratories (Bar Harbor, ME) were purchased and maintained in a vivarium. The animals were given free access to food and water for the duration of the study. All procedures were performed under a protocol approved by the Institutional Animal Care and Use Committee.
Subretinal Injection.
Mydriasis and cycloplegia was induced with a topical application of Tropicamide (Alcon, Fort Worth, TX). Torpor was induced and maintained using 3.5% isoflurane carried in 800 mL/minute of oxygen delivered to the animal via a nose cone. The eye was immobilized using ring tipped forceps (World Precision Instruments, Sarasota, FL) and a pilot incision was placed approximately 2 mm below the limbus on in the sclera using a 30 gauge needle. A 33 gauge blunt tipped needle was directed through the incision and advanced posteriorly until the tip penetrated the posterior neurosensory retina. One microliter of test article was delivered over one second. The needle was held in position for approximately five seconds before withdrawal. The animal was allowed to recover from anesthesia prior to returning to its cage.

Quantification of sFLT02 in Retinal Lysates.

sFLT02 in mouse retinal lysates was measured using the human soluble VEGF R1 ELISA kit by R&D Systems.

Results

To investigate the role of capsid surface arginine residues in AAVrh8 transduction of the retina, AAVrh8 vectors were generated with capsid proteins bearing mutations in residues that correspond to AAV2 arginines involved in HSPG binding. FIG. 14 compares five capsid residues critical for AAV2 binding to HSPG to the corresponding residues in AAVrh8R. As shown in FIG. 15, two AAVrh8R mutants were constructed, each bearing an amino acid substitution in these residues: A586R and R533A (numbering is based on VP1 amino acid sequence).

Figure 16A:
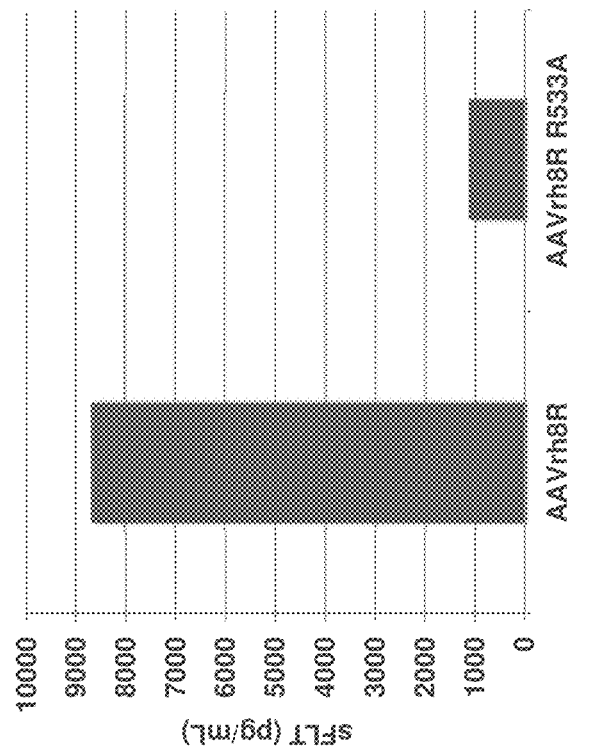
FIG. 16A shows the improved in vitro transduction of HeLa cells exhibited by the AAVrh8R A586R mutant, as compared to wild-type AAVrh8R. Transduction was monitored by sFLT02 in culture media 48 hour after infection with AAVrh8R or the AAVrh8R arginine modified vectors.

To evaluate the effect of adding arginine residues to the AAVrh8R capsid on in vitro transduction, HeLa cells were infected with either AAVrh8R-sFLT02 or a modified AAVrh8R-A586R-sFLT02 vector that has an arginine added at position A586 (AAVrh8R A586R), both at $1\times10^4$ DRP/cell. 48 hours post-infection, transduction efficiency was assessed by measuring sFLT02 in the cell culture media. AAVrh8R-A586R exhibited several fold higher transduction compared to the unmodified AAVrh8R (FIG. 16A).

Figure 16B:
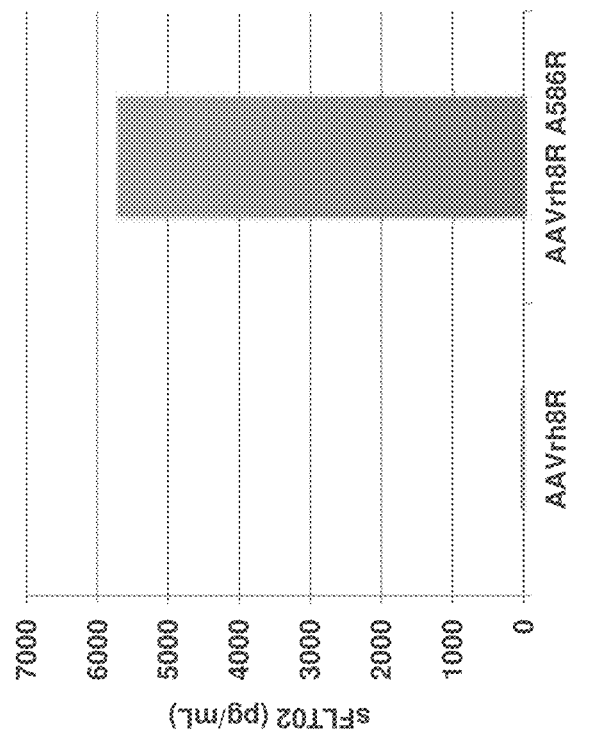
FIG. 16B shows the diminished in vitro transduction of HeLaRC32 cells exhibited by the AAVrh8R R533A mutant, as compared to wild-type AAVrh8R. Transduction was monitored by sFLT02 in culture media 48 hour after infection with AAVrh8R or the AAVrh8R arginine modified vectors.

To evaluate the effect of removing capsid arginines on in vitro transduction, HeLaRC32 cells were infected with either the AAVrh8R or the AAVrh8R-R533A vector (both at $1\times10^4$ DRP/cell). AAVrh8R-R533A had significantly reduced transduction when compared to the AAVrh8R (FIG. 16B).

Figure 17B:
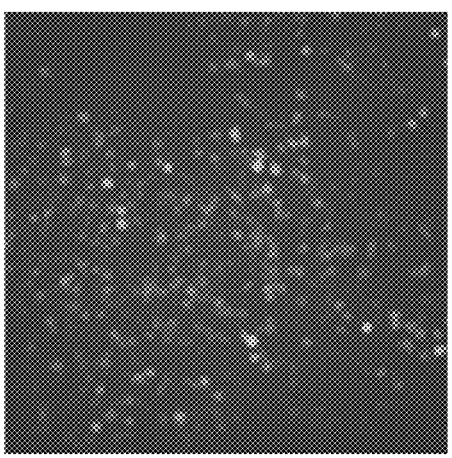
FIGS. 17A-17D show the levels in vitro transduction exhibited by AAVrh8R A586R and R533A mutants, as compared to wild-type AAVrh8R. AAVrh8R A586R mutant (FIG. 17B) shows increased in vitro transduction of NS1 cells, as compared to wild-type AAVrh8R (FIG. 17A). AAVrh8R R533A mutant (FIG. 17D) shows decreased in vitro transduction of HeLa cells, as compared to wild-type AAVrh8R (FIG. 17C). Transduction was monitored by EGFP expression in cells 48 hour after infection with AAVrh8R or the AAVrh8R arginine modified vectors.
Figure 17D:
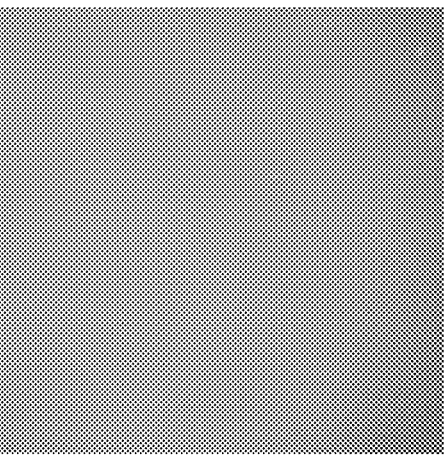
Figure 17A:
Figure 17C:
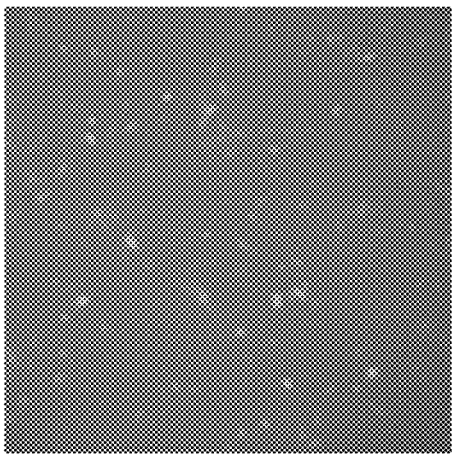

Similar experiments were undertaken using EGFP expression as a measure of transduction efficiency. AAVrh8R-A586R-EGFP exhibited substantially improved transduction of NS1 cells compared to AAVrh8R (compare FIG. 17B to FIG. 17A). Conversely, AAVrh8R-R533A-EGFP vector had reduced transduction on HeLa cells compared to AAVrh8R (compare FIG. 17D to FIG. 17C).

Collectively these experiments suggest that the addition of arginines to the AAVrh8R capsid improves AAVrh8R in vitro transduction while removing arginines from the AAVrh8R capsid impairs in vitro transduction. These results demonstrate that in vitro transduction by AAVrh8R is strongly influenced by arginine residues on the capsid.

To determine the effect of arginines on AAVrh8R subretinal transduction, C57B16 mice were injected with $1\times10^8$ DRP of AAVrh8R, AAVrh8R-A586R, or AAVrh8R-R533A expressing sFLT02 from the CBA promoter. Mice were sacrificed 30 days post-vector administration, and sFLT02 was measured in the retinal lysates.

Figure 18A:
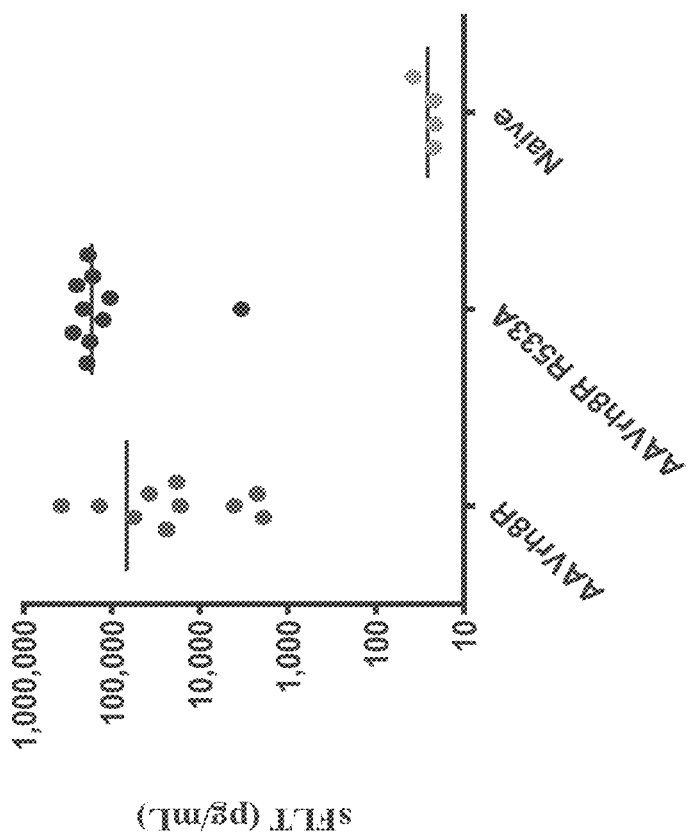
FIGS. 18A & 18B show the levels of subretinal transduction in C57B16 mice exhibited by AAVrh8R A586R and R533A mutants.
Figure 18B:
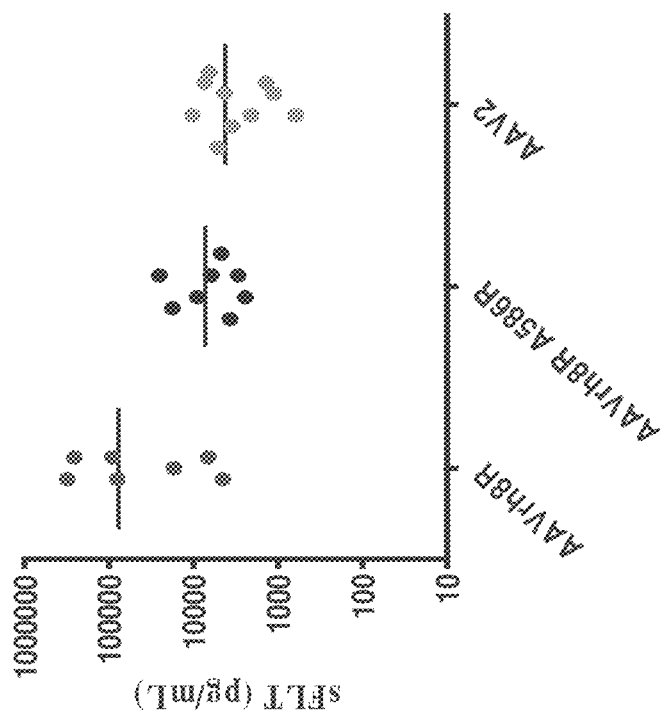

AAVrh8R-A586R transduction of the mouse retina was substantially reduced compared to AAVrh8R and in fact was comparable to AAV2, which also has an arginine in this same position, R585 (FIG. 18A). AAVrh8R-R533A transduction of the mouse retina was improved compared to AAVrh8R (FIG. 18B).

These data highlight the influence of capsid arginines on subretinal transduction of AAVrh8R and suggest that subretinal transduction is improved by the removal of arginines from the AAVrh8R capsid. These results demonstrate that subretinal transduction by AAVrh8R is strongly influenced by arginine residues on the capsid.

Example 8: Intravitreal Transduction of AAVrh8R is Improved by the Addition of Arginine at Position 586

Methods

Intravitreal Injection

Torpor was induced and maintained using 3.5 isoflurane carried in 800 mL/minute of oxygen delivered to the animal via a nose cone. One microliter of test article was injected into the vitreous humor using a Hamilton syringe fitted with a 33 gauge beveled needle (Hamilton Co., Reno, NV). The needle was directed through the sclera approximately 2 mm below the limbus and carefully advanced into the vitreal chamber to avoid contact with the lens. The test article was delivered over a 1-2 second period. Following the injection, the needle was held in position for approximately five seconds before withdrawal. The animal was allowed to recover from anesthesia prior to returning to its cage.

Quantification of sFLT02 in Retinal Lysates sFLT02 in mouse retinal lysates was measured using the human soluble VEGF R1 ELISA kit by R&D Systems.

Results

Figure 19:
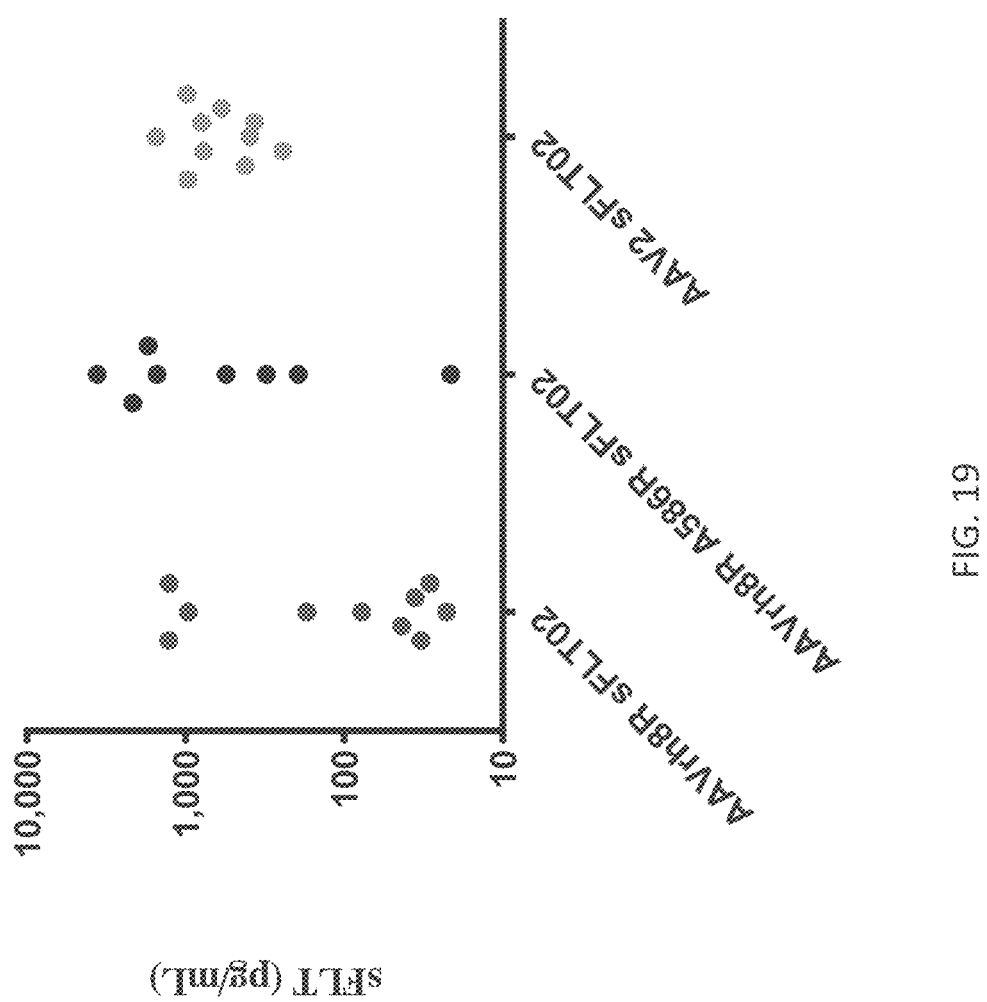
FIG. 19 shows the levels of sFLT02 in retinal lysates of C57B16 mice 30 days post-intravitreal administration of AAV2, AAVrh8R or AAVrh8R-A586R vectors.

To evaluate the effect of adding arginines to the AAV capsid on intravitreal transduction, C57B16 mice were injected with $1\times10^9$ DRP of AAV2, AAVrh8R, or AAVrh8R-A586R, each bearing a construct expressing sFLT02 from the CBA promoter. Mice were sacrificed 30 days post-vector administration and sFLT02 was measured in the retinal lysates. AAVrh8R-A586R transduction of the mouse retina was improved compared to AAVrh8R and in fact was comparable to AAV2 which also has an arginine in this same position, R585 (FIG. 19). This data indicates that intravitreal transduction of the retina can be improved by the addition of arginines to the AAV capsid. Based on these results and sequence homology among AAV capsids (FIG. 20), intravitreal transduction of the retina by AAV particles bearing AAV1, AAV6, AAV8, AAV9, and AAVrh10 capsids may similarly improve retinal transduction.

```
SEQUENCES
All polypeptide sequences are presented N-terminal to C-terminal
unless otherwise noted.
All nucleic sequences are presented 5' to 3' unless otherwise
noted.
AAV2 VP1 amino acid sequence
                                                        (SEQ ID NO: 1)
MAADGYLPDWLEDTLSEGIRQWWKLKPGPPPPKPAERHKDDSRGLVLPGYKYLGPFNGLDKGEPVNEAD

AAALEHDKAYDRQLDSGDNPYLKYNHADAEFQERLKEDTSFGGNLGRAVFQAKKRVLEPLGLVEEPVKT

APGKKRPVEHSPVEPDSSSGTGKAGQQPARKRLNFGQTGDADSVPDPQPLGQPPAAPSGLGTNTMATGSG

APMADNNEGADGVGNSSGNWHCDSTWMGDRVITTSTRTWALPTYNNHLYKQISSQSGASNDNHYFGYST
```

-continued

PWGYFDFNRFHCHFSPRDWQRLINNNWGFRPKRLNFKLFNIQVKEVTQNDGTTTIANNLTSTVQVFTDSEY

QLPYVLGSAHQGCLPPFPADVFMVPQYGYLTLNNGSQAVGRSSFYCLEYFPSQMLRTGNNFTFSYTFEDVP

FHSSYAHSQSLDRLMNPLIDQYLYYLSRTNTPSGTTTQSRLQFSQAGASDIRDQSRNWLPGPCYRQQRVSK

TSADNNNSEYSWTGATKYHLNGRDSLVNPGPAMASHKDDEEKFFPQSGVLIFGKQGSEKTNVDIEKVMIT

DEEEIRTTNPVATEQYGSVSTNLQRGNRQAATADVNTQGVLPGMVWQDRDVYLQGPIWAKIPHTDGHFH

PSPLMGGFGLKHPPPQILIKNTPVPANPSTTFSAAKFASFITQYSTGQVSVEIEWELQKENSKRWNPEIQYTS

NYNKSVNVDFTVDTNGVYSEPRPIGTRYLTRNL

AAV2 VP1 HBKO amino acid sequence (SEQ ID NO: 2)

MAADGYLPDWLEDTLSEGIRQWWKLKPGPPPPKPAERHKDDSRGLVLPGYKYLGPFNGLDKGEPVNEAD

AAALEHDKAYDRQLDSGDNPYLKYNHADAEFQERLKEDTSFGGNLGRAVFQAKKRVLEPLGLVEEPVKT

APGKKRPVEHSPVEPDSSSGTGKAGQQPARKRLNFGQTGDADSVPDPQPLGQPPAAPSGLGTNTMATGSG

APMADNNEGADGVGNSSGNWHCDSTWMGDRVITTSTRTWALPTYNNHLYKQISSQSGASNDNHYFGYST

PWGYFDFNRFHCHFSPRDWQRLINNNWGFRPKRLNFKLFNIQVKEVTQNDGTTTIANNLTSTVQVFTDSEY

QLPYVLGSAHQGCLPPFPADVFMVPQYGYLTLNNGSQAVGRSSFYCLEYFPSQMLRTGNNFTFSYTFEDVP

FHSSYAHSQSLDRLMNPLIDQYLYYLSRTNTPSGTTTQSRLQFSQAGASDIRDQSRNWLPGPCYRQQRVSK

TSADNNNSEYSWTGATKYHLNGRDSLVNPGPAMASHKDDEEKFFPQSGVLIFGKQGSEKTNVDIEKVMIT

DEEEIRTTNPVATEQYGSVSTNLQAGNAQAATADVNTQGVLPGMVWQDRDVYLQGPIWAKIPHTDGHFH

PSPLMGGFGLKHPPPQILIKNTPVPANPSTTFSAAKFASFITQYSTGQVSVEIEWELQKENSKRWNPEIQYTS

NYNKSVNVDFTVDTNGVYSEPRPIGTRYLTRNL

AAV2 VP2 amino acid sequence (SEQ ID NO: 3)

MAPGKKRPVEHSPVEPDSSSGTGKAGQQPARKRLNFGQTGDADSVPDPQPLGQPPAAPSGLGTNTMATGS

GAPMADNNEGADGVGNSSGNWHCDSTWMGDRVITTSTRTWALPTYNNHLYKQISSQSGASNDNHYFGY

STPWGYFDFNRFHCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLRTGNNFTFSYTFED

VPFHSSYAHSQSLDRLMNPLIDQYLYYLSRTNTPSGTTTQSRLQFSQAGASDIRDQSRNWLPGPCYRQQRV

SKTSADNNNSEYSWTGATKYHLNGRDSLVNPGPAMASHKDDEEKFFPQSGVLIFGKQGSEKTNVDIEKVM

ITDEEEIRTTNPVATEQYGSVSTNLQRGNRQAATADVNTQGVLPGMVWQDRDVYLQGPIWAKIPHTDGHF

HPSPLMGGFGLKHPPPQILIKNTPVPANPSTTFSAAKFASFITQYSTGQVSVEIEWELQKENSKRWNPEIQYT

SNYNKSVNVDFTVDTNGVYSEPRPIGTRYLTRNL

AAV2 VP2 HBKO amino acid sequence (SEQ ID NO: 4)

MAPGKKRPVEHSPVEPDSSSGTGKAGQQPARKRLNFGQTGDADSVPDPQPLGQPPAAPSGLGTNTMATGS

GAPMADNNEGADGVGNSSGNWHCDSTWMGDRVITTSTRTWALPTYNNHLYKQISSQSGASNDNHYFGY

STPWGYFDFNRFHCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLRTGNNFTFSYTFED

VPFHSSYAHSQSLDRLMNPLIDQYLYYLSRTNTPSGTTTQSRLQFSQAGASDIRDQSRNWLPGPCYRQQRV

SKTSADNNNSEYSWTGATKYHLNGRDSLVNPGPAMASHKDDEEKFFPQSGVLIFGKQGSEKTNVDIEKVM

ITDEEEIRTTNPVATEQYGSVSTNLQAGNAQAATADVNTQGVLPGMVWQDRDVYLQGPIWAKIPHTDGHF

HPSPLMGGFGLKHPPPQILIKNTPVPANPSTTFSAAKFASFITQYSTGQVSVEIEWELQKENSKRWNPEIQYT

SNYNKSVNVDFTVDTNGVYSEPRPIGTRYLTRNL

```
AAV2 VP3 amino acid sequence
                                                      (SEQ ID NO: 5)
MATGSGAPMADNNEGADGVGNSSGNWHCDSTWMGDRVITTSTRTWALPTYNNHLYKQISSQSGASNDN

HYFGYSTPWGYFDFNRFHCHFSPRDWQRLINNNWGFRPKRLNFKLFNIQVKEVTQNDGTTTIANNLTSTVQ

VFTDSEYQLPYVLGSAHQGCLPPFPADVFMVPQYGYLTLNNGSQAVGRSSFYCLEYFPSQMLRTGNNFTFS

YTFEDVPFHSSYAHSQSLDRLMNPLIDQYLYYLSRTNTPSGTTTQSRLQFSQAGASDIRDQSRNWLPGPCYR

QQRVSKTSADNNNSEYSWTGATKYHLNGRDSLVNPGPAMASHKDDEEKFFPQSGVLIFGKQGSEKTNVDI

EKVMITDEEEIRTTNPVATEQYGSVSTNLQRGNRQAATADVNTQGVLPGMVWQDRDVYLQGPIWAKIPHT

DGHFHPSPLMGGFGLKHPPPQILIKNTPVPANPSTTFSAAKFASFITQYSTGQVSVEIEWELQKENSKRWNPE

IQYTSNYNKSVNVDFTVDTNGVYSEPRPIGTRYLTRNL

AAV2 VP3 HBKO amino acid sequence
                                                      (SEQ ID NO: 6)
MATGSGAPMADNNEGADGVGNSSGNWHCDSTWMGDRVITTSTRTWALPTYNNHLYKQISSQSGASNDN

HYFGYSTPWGYFDFNRFHCHFSPRDWQRLINNNWGFRPKRLNFKLFNIQVKEVTQNDGTTTIANNLTSTVQ

VFTDSEYQLPYVLGSAHQGCLPPFPADVFMVPQYGYLTLNNGSQAVGRSSFYCLEYFPSQMLRTGNNFTFS

YTFEDVPFHSSYAHSQSLDRLMNPLIDQYLYYLSRTNTPSGTTTQSRLQFSQAGASDIRDQSRNWLPGPCYR

QQRVSKTSADNNNSEYSWTGATKYHLNGRDSLVNPGPAMASHKDDEEKFFPQSGVLIFGKQGSEKTNVDI

EKVMITDEEEIRTTNPVATEQYGSVSTNLQAGNAQAATADVNTQGVLPGMVWQDRDVYLQGPIWAKIPH

TDGHFHPSPLMGGFGLKHPPPQILIKNTPVPANPSTTFSAAKFASFITQYSTGQVSVEIEWELQKENSKRWNP

EIQYTSNYNKSVNVDFTVDTNGVYSEPRPIGTRYLTRNL

AAV3 VP1 amino acid sequence
                                                      (SEQ ID NO: 7)
MAADGYLPDWLEDNLSEGIREWWALKPGVPQPKANQQHQDNRRGLVLPGYKYLGPGNGLDKGEPVNE

ADAAALEHDKAYDQQLKAGDNPYLKYNHADAEFQERLQEDTSFGGNLGRAVFQAKKRILEPLGLVEEA

AKTAPGKKRPVDQSPQEPDSSSGVGKSGKQPARKRLNFGQTGDSESVPDPQPLGEPPAAPTSLGSNTMAS

GGGAPMADNNEGADGVGNSSGNWHCDSQWLGDRVITTSTRTWALPTYNNHLYKQISSQSGASNDNHY

FGYSTPWGYFDFNRFHCHFSPRDWQRLINNNWGFRPKKLSFKLFNIQVKEVTQNDGTTTIANNLTSTVQ

VFTDSEYQLPYVLGSAHQGCLPPFPADVFMVPQYGYLTLNNGSQAVGRSSFYCLEYFPSQMLRTGNNFQ

FSYTFEDVPFHSSYAHSQSLDRLMNPLIDQYLYYLNRTQGTTSGTTNQSRLLFSQAGPQSMSLQARNWLP

GPCYRQQRLSKTANDNNNSNFPWTAASKYHLNGRDSLVNPGPAMASHKDDEEKFFPMHGNLIFGKEGT

TASNAELDNVMITDEEEIRTTNPVATEQYGTVANNLQSSNTAPTTRTVNDQGALPGMVWQDRDVYLQG

PIWAKIPHTDGHFHPSPLMGGFGLKHPPPQIMIKNTPVPANPPTTFSPAKFASFITQYSTGQVSVEIEWELQ

KENSKRWNPEIQYTSNYNKSVNVDFTVDTNGVYSEPRPIGTRYLTRNL

Mutated ITR for scAAV vectors
                                                      (SEQ ID NO: 8)
CACTCCCTCTCTGCGCGCTCGCTCGCTCACTGAGGCCGGGCGACCAAAGGTCGCCCACGCCCGGGCT

TTGCCCGGGCG

AAVrh8R VP1 amino acid sequence
                                                      (SEQ ID NO: 9)
MAADGYLPDWLEDNLSEGIREWWDLKPGAPKPKANQQKQDDGRGLVLPGYKYLGPFNGLDKGEPVNA

ADAAALEHDKAYDQQLKAGDNPYLRYNHADAEFQERLQEDTSFGGNLGRAVFQAKKRVLEPLGLVEE

GAKTAPGKKRPVEQSPQEPDSSSGIGKTGQQPAKKRLNFGQTGDSESVPDPQPLGEPPAAPSGLGPNTMA

SGGGAPMADNNEGADGVGNSSGNWHCDSTWLGDRVITTSTRTWALPTYNNHLYKQISNGTSGGSTND

NTYFGYSTPWGYFDFNRFHCHFSPRDWQRLINNNWGFRPKRLNFKLFNIQVKEVTTNEGTKTIANNLTST

VQVFTDSEYQLPYVLGSAHQGCLPPFPADVFMVPQYGYLTLNNGSQALGRSSFYCLEYFPSQMLRTGNN
```

-continued

FQFSYTFEDVPFHSSYAHSQSLDRLMNPLIDQYLYYLVRTQTTGTGGTQTLAFSQAGPSSMANQARNWV

PGPCYRQQRVSTTTNQNNNSNFAWTGAAKFKLNGRDSLMNPGVAMASHKDDEDRFFPSSGVLIFGKQG

AGNDGVDYSQVLITDEEEIKATNPVATEEYGAVAINNQAANTQAQTGLVHNQGVIPGMVWQNRDVYL

QGPIWAKIPHTDGNFHPSPLMGGFGLKHPPPQILIKNTPVPADPPLTFNQAKLNSFITQYSTGQVSVEIEWE

LQKENSKRWNPEIQYTSNYYKSTNVDFAVNTEGVYSEPRPIGTRYLTRNL

AAVrh8R A586R mutant VP1 amino acid sequence (SEQ ID NO: 10)

MAADGYLPDWLEDNLSEGIREWWDLKPGAPKPKANQQKQDDGRGLVLPGYKYLGPFNGLDKGEPVNA

ADAAALEHDKAYDQQLKAGDNPYLRYNHADAEFQERLQEDTSFGGNLGRAVFQAKKRVLEPLGLVEE

GAKTAPGKKRPVEQSPQEPDSSSGIGKTGQQPAKKRLNFGQTGDSESVPDPQPLGEPPAAPSGLGPNTMA

SGGGAPMADNNEGADGVGNSSGNWHCDSTWLGDRVITTSTRTWALPTYNNHLYKQISNGTSGGSTND

NTYFGYSTPWGYFDFNRFHCHFSPRDWQRLINNNWGFRPKRLNFKLFNIQVKEVTTNEGTKTIANNLTST

VQVFTDSEYQLPYVLGSAHQGCLPPFPADVFMVPQYGYLTLNNGSQALGRSSFYCLEYFPSQMLRTGNN

FQFSYTFEDVPFHSSYAHSQSLDRLMNPLIDQYLYYLVRTQTTGTGGTQTLAFSQAGPSSMANQARNWV

PGPCYRQQRVSTTTNQNNNSNFAWTGAAKFKLNGRDSLMNPGVAMASHKDDEDRFFPSSGVLIFGKQG

AGNDGVDYSQVLITDEEEIKATNPVATEEYGAVAINNQRANTQAQTGLVHNQGVIPGMVWQNRDVYLQ

GPIWAKIPHTDGNFHPSPLMGGFGLKHPPPQILIKNTPVPADPPLTFNQAKLNSFITQYSTGQVSVEIEWEL

QKENSKRWNPEIQYTSNYYKSTNVDFAVNTEGVYSEPRPIGTRYLTRNL

AAVrh8R R533A mutant VP1 amino acid sequence (SEQ ID NO: 11)

MAADGYLPDWLEDNLSEGIREWWDLKPGAPKPKANQQKQDDGRGLVLPGYKYLGPFNGLDKGEPVNA

ADAAALEHDKAYDQQLKAGDNPYLRYNHADAEFQERLQEDTSFGGNLGRAVFQAKKRVLEPLGLVEE

GAKTAPGKKRPVEQSPQEPDSSSGIGKTGQQPAKKRLNFGQTGDSESVPDPQPLGEPPAAPSGLGPNTMA

SGGGAPMADNNEGADGVGNSSGNWHCDSTWLGDRVITTSTRTWALPTYNNHLYKQISNGTSGGSTND

NTYFGYSTPWGYFDFNRFHCHFSPRDWQRLINNNWGFRPKRLNFKLFNIQVKEVTTNEGTKTIANNLTST

VQVFTDSEYQLPYVLGSAHQGCLPPFPADVFMVPQYGYLTLNNGSQALGRSSFYCLEYFPSQMLRTGNN

FQFSYTFEDVPFHSSYAHSQSLDRLMNPLIDQYLYYLVRTQTTGTGGTQTLAFSQAGPSSMANQARNWV

PGPCYRQQRVSTTINQNNNSNFAWTGAAKFKLNGRDSLMNPGVAMASHKDDEDAFFPSSGVLIFGKQG

AGNDGVDYSQVLITDEEEIKATNPVATEEYGAVAINNQAANTQAQTGLVHNQGVIPGMVWQNRDVYL

QGPIWAKIPHTDGNFHPSPLMGGFGLKHPPPQILIKNTPVPADPPLTFNQAKLNSFITQYSTGQVSVEIEWE

LQKENSKRWNPEIQYTSNYYKSTNVDFAVNTEGVYSEPRPIGTRYLTRNL

AAV1 VP1 amino acid sequence (SEQ ID NO: 12)

MAADGYLPDWLEDNLSEGIREWWDLKPGAPKPKANQQKQDDGRGLVLPGYKYLGPFNGLD

KGEPVNAADAAALEHDKAYDQQLKAGDNPYLRYNHADAEFQERLQEDTSFGGNLGRAVFQ

AKKRVLEPLGLVEEGAKTAPGKKRPVEQSPQEPDSSSGIGKTGQQPAKKRLNFGQTGDSE

SVPDPQPLGEPPATPAAVGPTTMASGGGAPMADNNEGADGVGNASGNWHCDSTWLGDRVI

TTSTRTWALPTYNNHLYKQISSASTGASNDNHYFGYSTPWGYFDFNRFHCHFSPRDWQRL

INNNWGFRPKRLNFKLFNIQVKEVTTNDGVTTIANNLTSTVQVFSDSEYQLPYVLGSAHQ

GCLPPFPADVFMIPQYGYLTLNNGSQAVGRSSFYCLEYFPSQMLRTGNNFTFSYTFEEVP

FHSSYAHSQSLDRLMNPLIDQYLYYLNRTQNQSGSAQNKDLLFSRGSPAGMSVQPKNWLP

GPCYRQQRVSKTKTDNNNSNFTWTGASKYNLNGRESIINPGTAMASHKDDEDKFFPMSGV

MIFGKESAGASNTALDNVMITDEEEIKATNPVATERFGTVAVNFQSSSTDPATGDVHAMG

ALPGMVWQDRDVYLQGPIWAKIPHTDGHFHPSPLMGGFGLKNPPPQILIKNTPVPANPPA

EFSATKFASFITQYSTGQVSVEIEWELQKENSKRWNPEVQYTSNYAKSANVDFTVDNNGL

YTEPRPIGTRYLTRPL

AAV6 VP1 amino acid sequence
(SEQ ID NO: 13)

MAADGYLPDWLEDNLSEGIREWWDLKPGAPKPKANQQKQDDGRGLVLPGYKYLGPFNGLD

KGEPVNAADAAALEHDKAYDQQLKAGDNPYLRYNHADAEFQERLQEDTSFGGNLGRAVFQ

AKKRVLEPFGLVEEGAKTAPGKKRPVEQSPQEPDSSSGIGKTGQQPAKKRLNFGQTGDSE

SVPDPQPLGEPPATPAAVGPTTMASGGGAPMADNNEGADGVGNASGNWHCDSTWLGDRVI

TTSTRTWALPTYNNHLYKQISSASTGASNDNHYFGYSTPWGYFDFNRFHCHFSPRDWQRL

INNNWGFRPKRLNFKLFNIQVKEVTTNDGVTTIANNLTSTVQVFSDSEYQLPYVLGSAHQ

GCLPPFPADVFMIPQYGYLTLNNGSQAVGRSSFYCLEYFPSQMLRTGNNFTFSYTFEDVP

FHSSYAHSQSLDRLMNPLIDQYLYYLNRTQNQSGSAQNKDLLFSRGSPAGMSVQPKNWLP

GPCYRQQRVSKTKTDNNNSNFTWTGASKYNLNGRESIINPGTAMASHKDDKDKFFPMSGV

MIFGKESAGASNTALDNVMITDEEEIKATNPVATERFGTVAVNLQSSSTDPATGDVHVMG

ALPGMVWQDRDVYLQGPIWAKIPHTDGHFHPSPLMGGFGLKHPPPQILIKNTPVPANPPA

EFSATKFASFITQYSTGQVSVEIEWELQKENSKRWNPEVQYTSNYAKSANVDFTVDNNGL

YTEPRPIGTRYLTRPL

AAV8 VP1 amino acid sequence
(SEQ ID NO: 14)

MAADGYLPDWLEDNLSEGIREWWALKPGAPKPKANQQKQDDGRGLVLPGYKYLGPFNGLD

KGEPVNAADAAALEHDKAYDQQLQAGDNPYLRYNHADAEFQERLQEDTSFGGNLGRAVFQ

AKKRVLEPLGLVEEGAKTAPGKKRPVEPSPQRSPDSSTGIGKKGQQPARKRLNFGQTGDS

ESVPDPQPLGEPPAAPSGVGPNTMAAGGGAPMADNNEGADGVGSSSGNWHCDSTWLGDRV

ITTSTRTWALPTYNNHLYKQISNGTSGGATNDNTYFGYSTPWGYFDFNRFHCHFSPRDWQ

RLINNNWGFRPKRLSFKLFNIQVKEVTQNEGTKTIANNLTSTIQVFTDSEYQLPYVLGSA

HQGCLPPFPADVFMIPQYGYLTLNNGSQAVGRSSFYCLEYFPSQMLRTGNNFQFTYTFED

VPFHSSYAHSQSLDRLMNPLIDQYLYYLSRTQTTGGTANTQTLGFSQGGPNTMANQAKNW

LPGPCYRQQRVSTTTGQNNNSNFAWTAGTKYHLNGRNSLANPGIAMATHKDDEERFFPSN

GILIFGKQNAARDNADYSDVMLTSEEEIKTTNPVATEEYGIVADNLQQQNTAPQIGTVNS

QGALPGMVWQNRDVYLQGPIWAKIPHTDGNFHPSPLMGGFGLKHPPPQILIKNTPVPADP

PTTFNQSKLNSFITQYSTGQVSVEIEWELQKENSKRWNPEIQYTSNYYKSTSVDFAVNTE

GVYSEPRPIGTRYLTRNL

AAV9 VP1 amino acid sequence
(SEQ ID NO: 15)

MAADGYLPDWLEDNLSEGIREWWALKPGAPQPKANQQHQDNARGLVLPGYKYLGPGNGLD

KGEPVNAADAAALEHDKAYDQQLKAGDNPYLKYNHADAEFQERLKEDTSFGGNLGRAVFQ

AKKRLLEPLGLVEEAAKTAPGKKRPVEQSPQEPDSSAGIGKSGAQPAKKRLNFGQTGDTE

SVPDPQPIGEPPAAPSGVGSLTMASGGGAPVADNNEGADGVGSSSGNWHCDSQWLGDRVI

TTSTRTWALPTYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDYQLPYVLGSAH

EGCLPPFPADVFMIPQYGYLTLNDGSQAVGRSSFYCLEYFPSQMLRTGNNFQFSYEFENV

PFHSSYAHSQSLDRLMNPLIDQYLYYLSKTINGSGQNQQTLKFSVAGPSNMAVQGRNYIP

GPSYRQQRVSTTVTQNNNSEFAWPGASSWALNGRNSLMNPGPAMASHKEGEDRFFPLSGS

-continued

LIFGKQGTGRDNVDADKVMITNEEEIKTTNPVATESYGQVATNHQSAQAQAQTGWVQNQG

ILPGMVWQDRDVYLQGPIWAKIPHTDGNFHPSPLMGGFGMKHPPPQILIKNTPVPADPPT

AFNKDKLNSFITQYSTGQVSVEIEWELQKENSKRWNPEIQYTSNYYKSNNVEFAVNTEGV

YSEPRPIGTRYLTRNL

AAVrh10 VP1 amino acid sequence
(SEQ ID NO: 16)
MAADGYLPDWLEDNLSEGIREWWDLKPGAPKPKANQQKQDDGRGLVLPGYKYLGPFNGLD

KGEPVNAADAAALEHDKAYDQQLKAGDNPYLRYNHADAEFQERLQEDTSFGGNLGRAVFQ

AKKRVLEPLGLVEEGAKTAPGKKRPVEPSPQRSPDSSTGIGKKGQQPAKKRLNFGQTGDS

ESVPDPQPIGEPPAGPSGLGSGTMAAGGGAPMADNNEGADGVGSSSGNWHCDSTWLGDRV

ITTSTRTWALPTYNNHLYKQISNGTSGGSTNDNTYFGYSTPWGYFDFNRFHCHFSPRDWQ

RLINNNWGFRPKRLNFKLFNIQVKEVTQNEGTKTIANNLTSTIQVFTDSEYQLPYVLGSA

HQGCLPPFPADVFMIPQYGYLTLNNGSQAVGRSSFYCLEYFPSQMLRTGNNFEFSYQFED

VPFHSSYAHSQSLDRLMNPLIDQYLYYLSRTQSTGGTAGTQQLLFSQAGPNNMSAQAKNW

LPGPCYRQQRVSTTLSQNNNSNFAWTGATKYHLNGRDSLVNPGVAMATHKDDEERFFPSS

GVLMFGKQGAGKDNVDYSSVMLTSEEEIKTTNPVATEQYGVVADNLQQQNAAPIVGAVNS

QGALPGMVWQNRDVYLQGPIWAKIPHTDGNFHPSPLMGGFGLKHPPPQILIKNTPVADP

PTTFSQAKLASFITQYSTGQVSVEIEWELQKENSKRWNPEIQYTSNYYKSTNVDFAVNTD

GTYSEPRPIGTRYLTRNL

---

What is claimed is:

1. A method for delivering a heterologous nucleic acid to the central nervous system (CNS) of an individual comprising administering a recombinant adeno-associated virus (rAAV) particle to the CNS of the individual, wherein:
   (i) the rAAV particle is an AAV serotype 2 (AAV2) particle comprising:
      a) an AAV2 capsid comprising an AAV2 capsid protein comprising a R585A substitution, a R588A substitution, or R585A and R588A substitutions, numbering based on VP1 numbering of AAV2, and
      b) a rAAV vector comprising the heterologous nucleic acid and at least one AAV inverted terminal repeat; or
   (ii) the rAAV particle is an AAV serotype rh8R (AAVrh8R) particle comprising:
      (a) an AAVrh8R capsid comprising an AAVrh8R capsid protein comprising a R533A substitution, numbering based on VP1 numbering of AAVrh8R, and
      (b) a rAAV vector comprising the heterologous nucleic acid and at least one AAV inverted terminal repeat.

2. The method of claim 1, wherein the administration comprises direct spinal cord injection, intracranial, and/or intracerebral administration.

3. The method of claim 1, wherein the heterologous nucleic acid is expressed in one or more cells of the CNS.

4. The method of claim 3, wherein the one or more cells of the CNS is an oligodendrocyte, astrocyte, neuron, brain parenchyma cell, microglial cell, ependymal cell, and/or a Purkinje cell.

5. The method of claim 1, wherein the heterologous nucleic acid is expressed in a neuron.

6. The method of claim 1, wherein the heterologous nucleic acid encodes a therapeutic polypeptide or therapeutic nucleic acid.

7. The method of claim 1, wherein the heterologous nucleic acid encodes a CNS-associated gene.

8. The method of claim 1, wherein the heterologous nucleic acid encodes a polypeptide selected from the group consisting of an enzyme, a neurotrophic factor, a polypeptide that is deficient or mutated in an individual with a CNS-related disorder, an antioxidant, an anti-apoptotic factor, an anti-angiogenic factor, and an anti-inflammatory factor, alpha-synuclein, acid beta-glucosidase (GBA), beta-galactosidase-1 (GLB1), iduronate 2-sulfatase (IDS), galactosylceramidase (GALC), a mannosidase, alpha-D-mannosidase (MAN2B1), beta-mannosidase (MANBA), pseudoarylsulfatase A (ARSA), N-acetylglucosamine-1-phosphotransferase (GNPTAB), acid sphingomyelinase (ASM), Niemann-Pick C protein (NPC1), acid alpha-1,4-glucosidase (GAA), hexosaminidase beta subunit, HEXB, N-sulfoglucosamine sulfohydrolase (MPS3A), N-alpha-acetylglucosaminidase (NAGLU), heparin acetyl-CoA, alpha-glucosaminidase N-acetyltransferase (MPS3C), N-acetylglucosamine-6-sulfatase (GNS), alpha-N-acetylgalactosaminidase (NAGA), beta-glucuronidase (GUSB), hexosaminidase alpha subunit (HEXA), huntingtin (HTT), lysosomal acid lipase (LIPA), Aspartylglucosaminidase, Alpha-galactosidase A, Palmitoyl protein thioesterase, Tripeptidyl peptidase, Lysosomal transmembrane protein, Cysteine transporter, Acid ceramidase, Acid alpha-L-fucosidase, cathepsin A, alpha-L-iduronidase, Arylsulfatase B, Arylsulfatase A, N-acetylgalactosamine-6-sulfate, Acid beta-galactosidase, or alpha-neuraminidase.

9. The method of claim 8, wherein the heterologous nucleic acid encodes a polypeptide selected from the group consisting of neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), amino acid decarboxylase (AADC), an anti-oxidant, an anti-angiogenic polypeptide, an anti-inflammatory polypeptide, and aspartoacylase (ASPA).

10. The method of claim 1, wherein the heterologous nucleic acid encodes a therapeutic nucleic acid.

11. The method of claim 10, wherein the therapeutic nucleic acid is an siRNA, an shRNA, an RNAi, an miRNA, an antisense RNA, a ribozyme or a DNAzyme.

12. The method of claim 1, wherein the heterologous nucleic acid is under the control of a promoter sequence that is expressed in one or more cells of the CNS.

13. The method of claim 12, wherein the heterologous nucleic acid is operably linked to a promoter.

14. The method of claim 13, wherein the one or more cells of the CNS is an oligodendrocyte, astrocyte, neuron, brain parenchyma cell, microglial cell, ependymal cell, and/or a Purkinje cell.

15. The method of claim 13, wherein the cell of the CNS is a neuron.

16. The method of claim 1, wherein the heterologous nucleic acid is under the control of a promoter sequence selected from the group consisting of a cytomegalovirus (CMV) immediate early promoter, an RSV LTR, a MoML V LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a β-actin promoter.

17. The method of claim 1, wherein the rAAV vector is a self-complementary rAAV vector.

18. The method of claim 17, wherein the vector comprises first nucleic acid sequence encoding the heterologous nucleic acid and a second nucleic acid sequence encoding a complement of the nucleic acid, wherein the first nucleic acid sequence can form intrastrand base pairs with the second nucleic acid sequence along most or all of its length.

19. The method of claim 18, wherein the first nucleic acid sequence and the second nucleic acid sequence are linked by a mutated AAV ITR, wherein the mutated AAV ITR comprises a deletion of the D region and comprises a mutation of the terminal resolution sequence.

20. The method of claim 1, wherein the individual is a human.

21. The method of claim 1, wherein the heterologous nucleic acid encodes a therapeutic polypeptide or a therapeutic nucleic acid used to treat a disorder of the CNS.

22. The method of claim 21, wherein the disorder of the CNS is a lysosomal storage disease (LSD), Huntington's disease, epilepsy, Parkinson's disease, Alzheimer's disease, stroke, corticobasal degeneration (CBD), corticogasal ganglionic degeneration (CBGD), frontotemporal dementia (FTD), multiple system atrophy (MSA), progressive supranuclear palsy (PSP) or cancer of the brain.

23. The method of claim 22, wherein the disorder is a lysosomal storage disease selected from the group consisting of Aspartylglusoaminuria, Fabry, Infantile Batten Disease (CNL1), Classic Late Infantile Batten Disease (CNL2), Juvenile Batten Disease (CNL3), Batten form CNL4, Batten form CNL5, Batten form CNL6, Batten form CNL7, Batten form CNL8, Cystinosis, Farber, Fucosidosis, Galactosidosialidosis, Gaucher disease type 1, Gaucher disease type 2, Gaucher disease type 3, GM1 gangliosidosis, Hunter disease, Krabbe disease, a mannosidosis disease, β mannosidosis disease, Maroteaux-Lamy, metachromatic leukodystrophy disease, Morquio A, Morquio B, mucolipidosisII/III disease, Niemann-Pick A disease, Niemann-Pick B disease, Niemann-Pick C disease, Pompe disease, Sandhoff disease, Sanfillipo A disease, Sanfillipo B disease, Sanfillipo C disease, Sanfillipo D disease, Schindler disease, Schindler-Kanzaki, sialidosis, Sly disease, Tay-Sachs disease, and Wolman disease.

24. The method of claim 1, wherein the rAAV particle is an AAV2 particle comprising an AAV2 capsid comprising an AAV2 capsid protein comprising a R585A substitution.

25. The method of claim 1, wherein the rAAV particle is an AAV2 particle comprising an AAV2 capsid comprising an AAV2 capsid protein comprising a R588A substitution.

26. The method of claim 1, wherein the rAAV particle is an AAV2 particle comprising an AAV2 capsid comprising an AAV2 capsid protein comprising R585A and R588A substitutions.

27. The method of claim 1, wherein the rAAV particle is an AAVrh8R particle comprising an AAVrh8R capsid comprising an AAVrh8R capsid protein comprising a R533A substitution.

28. A method for improving rAAV transduction of cells in the central nervous system (CNS) of an individual compared to transduction of cells with a rAAV comprising a wild-type capsid, the method comprising administering a recombinant adeno-associated virus (rAAV) particle to the CNS of the individual, wherein:
(i) the rAAV particle is an AAV serotype 2 (AAV2) particle comprising:
a) an AAV2 capsid comprising an AAV2 capsid protein comprising a R585A substitution, a R588A substitution, or R585A and R588A substitutions, numbering based on VP1 numbering of AAV2, and
b) a rAAV vector comprising a heterologous nucleic acid and at least one AAV inverted terminal repeat; or
(ii) the rAAV particle is an AAV serotype rh8R (AAVrh8R) particle comprising:
(a) an AAVrh8R capsid comprising an AAVrh8R capsid protein comprising a R533A substitution, numbering based on VP1 numbering of AAVrh8R, and
(b) a rAAV vector comprising a heterologous nucleic acid and at least one AAV inverted terminal repeat.

29. The method of claim 28, wherein the rAAV particle is an AAV2 particle comprising an AAV2 capsid comprising an AAV2 capsid protein comprising a R585A substitution.

30. The method of claim 28, wherein the rAAV particle is an AAV2 particle comprising an AAV2 capsid comprising an AAV2 capsid protein comprising a R588A substitution.

31. The method of claim 28, wherein the rAAV particle is an AAV2 particle comprising an AAV2 capsid comprising an AAV2 capsid protein comprising R585A and R588A substitutions.

32. The method of claim 28, wherein the rAAV particle is an AAVrh8R particle comprising an AAVrh8R capsid comprising an AAVrh8R capsid protein comprising a R533A substitution.

33. A method for improving expression of a heterologous nucleic acid in the central nervous system (CNS) of an individual, the method comprising administering a recombinant adeno-associated virus (rAAV) particle to the CNS of the individual, wherein:
(i) the rAAV particle is an AAV serotype 2 (AAV2) particle comprising:
a) an AAV2 capsid comprising an AAV2 capsid protein comprising a R585A substitution, a R588A substitution, or R585A and R588A substitutions, numbering based on VP1 numbering of AAV2, and
b) a rAAV vector comprising a heterologous nucleic acid and at least one AAV inverted terminal repeat;

or
(ii) the rAAV particle is an AAV serotype rh8R (AAVrh8R) particle comprising:
   (a) an AAVrh8R capsid comprising an AAVrh8R capsid protein comprising a R533A substitution, numbering based on VP1 numbering of AAVrh8R, and
   (b) a rAAV vector comprising a heterologous nucleic acid and at least one AAV inverted terminal repeat.

34. The method of claim 33, wherein the rAAV particle is an AAV2 particle comprising an AAV2 capsid comprising an AAV2 capsid protein comprising a R585A substitution.

35. The method of claim 33, wherein the rAAV particle is an AAV2 particle comprising an AAV2 capsid comprising an AAV2 capsid protein comprising a R588A substitution.

36. The method of claim 33, wherein the rAAV particle is an AAV2 particle comprising an AAV2 capsid comprising an AAV2 capsid protein comprising R585A and R588A substitutions.

37. The method of claim 33, wherein the rAAV particle is an AAVrh8R particle comprising an AAVrh8R capsid comprising an AAVrh8R capsid protein comprising a R533A substitution.

* * * * *

SEQUENCE LISTING

<160> NUMBER OF SEQ ID NOS: 16

<210> SEQ ID NO 1
<211> LENGTH: 735
<212> TYPE: PRT
<213> ORGANISM: Adeno-associated virus

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

```
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
```

```
Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 2
<211> LENGTH: 735
<212> TYPE: PRT
<213> ORGANISM: Artificial Sequence
<220> FEATURE:
<223> OTHER INFORMATION: Synthetic Construct

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205
```

```
Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Ala Gly Asn Ala Gln Ala Ala Thr
            580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620
```

-continued

```
Asp Gly His Phe His Pro Ser Pro Leu Met Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 598
<212> TYPE: PRT
<213> ORGANISM: Adeno-associated virus

<400> SEQUENCE: 3

Met Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270
```

-continued

```
Thr Phe Ser Tyr Thr Phe Glu Asp Val Pro Phe His Ser Tyr Ala
            275                 280                 285

His Ser Gln Ser Leu Asp Arg Leu Met Asn Pro Leu Ile Asp Gln Tyr
        290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
            500                 505                 510

Asn Thr Pro Val Pro Ala Asn Pro Ser Thr Thr Phe Ser Ala Ala Lys
    515                 520                 525

Phe Ala Ser Phe Ile Thr Gln Tyr Ser Thr Gly Gln Val Ser Val Glu
530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 4
<211> LENGTH: 598
<212> TYPE: PRT
<213> ORGANISM: Artificial Sequence
<220> FEATURE:
<223> OTHER INFORMATION: Synthetic Construct

<400> SEQUENCE: 4

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30
```

-continued

```
Arg Leu Asn Phe Gly Gln Thr Gly Asp Ala Asp Ser Val Pro Asp Pro
            35                  40                  45

Gln Pro Leu Gly Gln Pro Pro Ala Ala Pro Ser Gly Leu Gly Thr Asn
 50                  55                  60

Thr Met Ala Thr Gly Ser Gly Ala Pro Met Ala Asp Asn Asn Glu Gly
 65                  70                  75                  80

Ala Asp Gly Val Gly Asn Ser Ser Gly Asn Trp His Cys Asp Ser Thr
                 85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
            115                 120                 125

Ala Ser Asn Asp Asn His Tyr Phe Gly Tyr Ser Thr Pro Trp Gly Tyr
            130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
                180                 185                 190

Thr Thr Ile Ala Asn Asn Leu Thr Ser Thr Val Gln Val Phe Thr Asp
            195                 200                 205

Ser Glu Tyr Gln Leu Pro Tyr Val Leu Gly Ser Ala His Gln Gly Cys
210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
                260                 265                 270

Thr Phe Ser Tyr Thr Phe Glu Asp Val Pro Phe His Ser Ser Tyr Ala
            275                 280                 285

His Ser Gln Ser Leu Asp Arg Leu Met Asn Pro Leu Ile Asp Gln Tyr
            290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
                340                 345                 350

Lys Thr Ser Ala Asp Asn Asn Ser Glu Tyr Ser Trp Thr Gly Ala
            355                 360                 365

Thr Lys Tyr His Leu Asn Gly Arg Asp Ser Leu Val Asn Pro Gly Pro
 370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
                420                 425                 430

Pro Val Ala Thr Glu Gln Tyr Gly Ser Val Ser Thr Asn Leu Gln Ala
            435                 440                 445
```

Gly Asn Ala Gln Ala Ala Thr Ala Asp Val Asn Thr Gln Gly Val Leu
        450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
            500                 505                 510      Lys

Asn Thr Pro Val Pro Ala Asn Pro Ser Thr Thr Phe Ser Ala Ala Lys
            515                 520                 525

Phe Ala Ser Phe Ile Thr Gln Tyr Ser Thr Gly Gln Val Ser Val Glu
530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 5
<211> LENGTH: 533
<212> TYPE: PRT
<213> ORGANISM: Adeno-associated virus

<400> SEQUENCE: 5

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
210                 215                 220

```
Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Gln Ser
            245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
            275                 280                 285

Thr Ser Ala Asp Asn Asn Ser Glu Tyr Ser Trp Thr Gly Ala Thr
290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
            325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
            355                 360                 365

Val Ala Thr Glu Gln Tyr Gly Ser Val Ser Thr Asn Leu Gln Arg Gly
370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
            405                 410                 415

Ala Lys Ile Pro His Thr Asp Gly His Phe His Pro Ser Pro Leu Met
            420                 425                 430

Gly Gly Phe Gly Leu Lys His Pro Pro Gln Ile Leu Ile Lys Asn
            435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
            485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
            515                 520                 525

Leu Thr Arg Asn Leu
            530

<210> SEQ ID NO 6
<211> LENGTH: 533
<212> TYPE: PRT
<213> ORGANISM: Artificial Sequence
<220> FEATURE:
<223> OTHER INFORMATION: Synthetic Construct

<400> SEQUENCE: 6

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45
```

```
Thr Tyr Asn Asn His Leu Tyr Lys Gln Ile Ser Ser Gln Ser Gly Ala
 50                  55                  60

Ser Asn Asp Asn His Tyr Phe Gly Tyr Ser Thr Pro Trp Gly Tyr Phe
 65                  70                  75                  80

Asp Phe Asn Arg Phe His Cys His Phe Ser Pro Arg Asp Trp Gln Arg
                 85                  90                  95

Leu Ile Asn Asn Asn Trp Gly Phe Arg Pro Lys Arg Leu Asn Phe Lys
                100                 105                 110

Leu Phe Asn Ile Gln Val Lys Glu Val Thr Gln Asn Asp Gly Thr Thr
             115                 120                 125

Thr Ile Ala Asn Asn Leu Thr Ser Thr Val Gln Val Phe Thr Asp Ser
 130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
                260                 265                 270

Arg Asn Trp Leu Pro Gly Pro Cys Tyr Arg Gln Gln Arg Val Ser Lys
            275                 280                 285

Thr Ser Ala Asp Asn Asn Asn Ser Glu Tyr Ser Trp Thr Gly Ala Thr
290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
        355                 360                 365

Val Ala Thr Glu Gln Tyr Gly Ser Val Ser Thr Asn Leu Gln Ala Gly
    370                 375                 380

Asn Ala Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asn Pro Ser Thr Thr Phe Ser Ala Ala Lys Phe
    450                 455                 460
```

-continued

```
Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
            485                 490                 495

Gln Tyr Thr Ser Asn Tyr Asn Lys Ser Val Asn Val Asp Phe Thr Val
        500                 505                 510

Asp Thr Asn Gly Val Tyr Ser Glu Pro Arg Pro Ile Gly Thr Arg Tyr
    515                 520                 525

Leu Thr Arg Asn Leu
    530

<210> SEQ ID NO 7
<211> LENGTH: 736
<212> TYPE: PRT
<213> ORGANISM: Adeno-associated virus

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720
```

```
Tyr Ser Glu Pro Arg Pro Ile Gly Thr Arg Tyr Leu Thr Arg Asn Leu
                725                 730                 735
```

<210> SEQ ID NO 8
<211> LENGTH: 78
<212> TYPE: DNA
<213> ORGANISM: Artificial Sequence
<220> FEATURE:
<223> OTHER INFORMATION: Synthetic Construct

<400> SEQUENCE: 8

```
cactccctct ctgcgcgctc gctcgctcac tgaggccggg cgaccaaagg tcgcccacgc    60
ccgggctttg cccgggcg                                                  78
```

<210> SEQ ID NO 9
<211> LENGTH: 736
<212> TYPE: PRT
<213> ORGANISM: Artificial Sequence
<220> FEATURE:
<223> OTHER INFORMATION: Synthetic Construct

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270
```

```
Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Glu Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685
```

```
Lys Glu Asn Ser Lys Arg Trp Asn Pro Glu Ile Gln Tyr Thr Ser Asn
    690                 695                 700
Tyr Tyr Lys Ser Thr Asn Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 10
<211> LENGTH: 736
<212> TYPE: PRT
<213> ORGANISM: Artificial Sequence
<220> FEATURE:
<223> OTHER INFORMATION: Synthetic Construct

<400> SEQUENCE: 10

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Ser Gly Leu Gly Pro Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
```

-continued

```
Gln Val Lys Glu Val Thr Thr Asn Glu Gly Thr Lys Thr Ile Ala Asn
            325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
            485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Glu Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
            565                 570                 575

Tyr Gly Ala Val Ala Ile Asn Asn Gln Arg Ala Asn Thr Gln Ala Gln
            580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

```
<210> SEQ ID NO 11
<211> LENGTH: 736
<212> TYPE: PRT
<213> ORGANISM: Artificial Sequence
<220> FEATURE:
<223> OTHER INFORMATION: Synthetic Construct

<400> SEQUENCE: 11
```

| Met | Ala | Ala | Asp | Gly | Tyr | Leu | Pro | Asp | Trp | Leu | Glu | Asp | Asn | Leu | Ser |
|---|---|---|---|---|---|---|---|---|---|---|---|---|---|---|---|
| 1 | | | | 5 | | | | | 10 | | | | | 15 | |

| Glu | Gly | Ile | Arg | Glu | Trp | Trp | Asp | Leu | Lys | Pro | Gly | Ala | Pro | Lys | Pro |
|---|---|---|---|---|---|---|---|---|---|---|---|---|---|---|---|
| | | | 20 | | | | | 25 | | | | | 30 | | |

| Lys | Ala | Asn | Gln | Gln | Lys | Gln | Asp | Asp | Gly | Arg | Gly | Leu | Val | Leu | Pro |
|---|---|---|---|---|---|---|---|---|---|---|---|---|---|---|---|
| | | 35 | | | | | 40 | | | | | 45 | | | |

| Gly | Tyr | Lys | Tyr | Leu | Gly | Pro | Phe | Asn | Gly | Leu | Asp | Lys | Gly | Glu | Pro |
|---|---|---|---|---|---|---|---|---|---|---|---|---|---|---|---|
| | 50 | | | | | 55 | | | | | 60 | | | | |

| Val | Asn | Ala | Ala | Asp | Ala | Ala | Leu | Glu | His | Asp | Lys | Ala | Tyr | Asp |
|---|---|---|---|---|---|---|---|---|---|---|---|---|---|---|
| 65 | | | | 70 | | | | | 75 | | | | | 80 |

| Gln | Gln | Leu | Lys | Ala | Gly | Asp | Asn | Pro | Tyr | Leu | Arg | Tyr | Asn | His | Ala |
|---|---|---|---|---|---|---|---|---|---|---|---|---|---|---|---|
| | | | | 85 | | | | | 90 | | | | | 95 | |

| Asp | Ala | Glu | Phe | Gln | Glu | Arg | Leu | Gln | Glu | Asp | Thr | Ser | Phe | Gly | Gly |
|---|---|---|---|---|---|---|---|---|---|---|---|---|---|---|---|
| | | | 100 | | | | | 105 | | | | | 110 | | |

| Asn | Leu | Gly | Arg | Ala | Val | Phe | Gln | Ala | Lys | Lys | Arg | Val | Leu | Glu | Pro |
|---|---|---|---|---|---|---|---|---|---|---|---|---|---|---|---|
| | | 115 | | | | | 120 | | | | | 125 | | | |

| Leu | Gly | Leu | Val | Glu | Glu | Gly | Ala | Lys | Thr | Ala | Pro | Gly | Lys | Lys | Arg |
|---|---|---|---|---|---|---|---|---|---|---|---|---|---|---|---|
| | 130 | | | | | 135 | | | | | 140 | | | | |

| Pro | Val | Glu | Gln | Ser | Pro | Gln | Glu | Pro | Asp | Ser | Ser | Gly | Ile | Gly |
|---|---|---|---|---|---|---|---|---|---|---|---|---|---|---|
| 145 | | | | | 150 | | | | | 155 | | | | | 160 |

| Lys | Thr | Gly | Gln | Gln | Pro | Ala | Lys | Lys | Arg | Leu | Asn | Phe | Gly | Gln | Thr |
|---|---|---|---|---|---|---|---|---|---|---|---|---|---|---|---|
| | | | | 165 | | | | | 170 | | | | | 175 | |

| Gly | Asp | Ser | Glu | Ser | Val | Pro | Asp | Pro | Gln | Pro | Leu | Gly | Glu | Pro | Pro |
|---|---|---|---|---|---|---|---|---|---|---|---|---|---|---|---|
| | | | 180 | | | | | 185 | | | | | 190 | | |

| Ala | Ala | Pro | Ser | Gly | Leu | Gly | Pro | Asn | Thr | Met | Ala | Ser | Gly | Gly | Gly |
|---|---|---|---|---|---|---|---|---|---|---|---|---|---|---|---|
| | | 195 | | | | | 200 | | | | | 205 | | | |

| Ala | Pro | Met | Ala | Asp | Asn | Asn | Glu | Gly | Ala | Asp | Gly | Val | Gly | Asn | Ser |
|---|---|---|---|---|---|---|---|---|---|---|---|---|---|---|---|
| | 210 | | | | | 215 | | | | | 220 | | | | |

| Ser | Gly | Asn | Trp | His | Cys | Asp | Ser | Thr | Trp | Leu | Gly | Asp | Arg | Val | Ile |
|---|---|---|---|---|---|---|---|---|---|---|---|---|---|---|---|
| 225 | | | | | 230 | | | | | 235 | | | | | 240 |

| Thr | Thr | Ser | Thr | Arg | Thr | Trp | Ala | Leu | Pro | Thr | Tyr | Asn | Asn | His | Leu |
|---|---|---|---|---|---|---|---|---|---|---|---|---|---|---|---|
| | | | | 245 | | | | | 250 | | | | | 255 | |

| Tyr | Lys | Gln | Ile | Ser | Asn | Gly | Thr | Ser | Gly | Gly | Ser | Thr | Asn | Asp | Asn |
|---|---|---|---|---|---|---|---|---|---|---|---|---|---|---|---|
| | | | 260 | | | | | 265 | | | | | 270 | | |

| Thr | Tyr | Phe | Gly | Tyr | Ser | Thr | Pro | Trp | Gly | Tyr | Phe | Asp | Phe | Asn | Arg |
|---|---|---|---|---|---|---|---|---|---|---|---|---|---|---|---|
| | | 275 | | | | | 280 | | | | | 285 | | | |

| Phe | His | Cys | His | Phe | Ser | Pro | Arg | Asp | Trp | Gln | Arg | Leu | Ile | Asn | Asn |
|---|---|---|---|---|---|---|---|---|---|---|---|---|---|---|---|
| | 290 | | | | | 295 | | | | | 300 | | | | |

| Asn | Trp | Gly | Phe | Arg | Pro | Lys | Arg | Leu | Asn | Phe | Lys | Leu | Phe | Asn | Ile |
|---|---|---|---|---|---|---|---|---|---|---|---|---|---|---|---|
| 305 | | | | | 310 | | | | | 315 | | | | | 320 |

| Gln | Val | Lys | Glu | Val | Thr | Thr | Asn | Glu | Gly | Thr | Lys | Thr | Ile | Ala | Asn |
|---|---|---|---|---|---|---|---|---|---|---|---|---|---|---|---|
| | | | | 325 | | | | | 330 | | | | | 335 | |

| Asn | Leu | Thr | Ser | Thr | Val | Gln | Val | Phe | Thr | Asp | Ser | Glu | Tyr | Gln | Leu |
|---|---|---|---|---|---|---|---|---|---|---|---|---|---|---|---|
| | | | 340 | | | | | 345 | | | | | 350 | | |

| Pro | Tyr | Val | Leu | Gly | Ser | Ala | His | Gln | Gly | Cys | Leu | Pro | Pro | Phe | Pro |
|---|---|---|---|---|---|---|---|---|---|---|---|---|---|---|---|
| | | 355 | | | | | 360 | | | | | 365 | | | |

```
Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Thr Gln Thr Leu Ala Phe Ser
        450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Glu Asp Ala Phe Phe Pro Ser Ser Gly Val Leu Ile Phe Gly
            530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 12
<211> LENGTH: 736
<212> TYPE: PRT
<213> ORGANISM: Adeno-associated virus

<400> SEQUENCE: 12

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400
```

```
Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 13
<211> LENGTH: 736
<212> TYPE: PRT
<213> ORGANISM: Adeno-associated virus

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70              75                  80

Gln Gln Leu Lys Ala Gly Asp Asn Pro Tyr Leu Arg Tyr Asn His Ala
                85              90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445
```

```
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Lys Asp Lys Phe Phe Pro Met Ser Gly Val Met Ile Phe Gly
530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Leu Gln Ser Ser Ser Thr Asp Pro Ala
                580                 585                 590
Thr Gly Asp Val His Val Met Gly Ala Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Val Gln Tyr Thr Ser Asn
690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 14
<211> LENGTH: 738
<212> TYPE: PRT
<213> ORGANISM: Adeno-associated virus

<400> SEQUENCE: 14

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
```

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

```
Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 15
<211> LENGTH: 736
<212> TYPE: PRT
<213> ORGANISM: Adeno-associated virus

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560
```

```
Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 738
<212> TYPE: PRT
<213> ORGANISM: Adeno-associated virus

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190
```

```
Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Ser Thr Asn Asp
            260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
        290                 295                 300

Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605
```

-continued

```
Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```